US011000385B2

(12) United States Patent
Kalhorn et al.

(10) Patent No.: US 11,000,385 B2
(45) Date of Patent: May 11, 2021

(54) EXPANDABLE DEVICE

(71) Applicant: MUSC Foundation for Research Development, Charleston, SC (US)

(72) Inventors: Stephen Kalhorn, Mt Pleasant, SC (US); Mark E. Semler, Mt Pleasant, SC (US); Joseph Ruscito, Southport, CT (US); Christopher Hapstack, Charleston, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 0 days.

(21) Appl. No.: 16/339,024

(22) PCT Filed: Oct. 1, 2018

(86) PCT No.: PCT/US2018/053716
§ 371 (c)(1),
(2) Date: Apr. 3, 2019

(87) PCT Pub. No.: WO2019/068074
PCT Pub. Date: Apr. 4, 2019

(65) Prior Publication Data
US 2020/0214851 A1    Jul. 9, 2020

Related U.S. Application Data

(60) Provisional application No. 62/565,374, filed on Sep. 29, 2017.

(51) Int. Cl.
| A61F 2/44 | (2006.01) |
| A61F 2/46 | (2006.01) |
| A61F 2/30 | (2006.01) |

(52) U.S. Cl.
CPC .......... *A61F 2/4455* (2013.01); *A61F 2/4611* (2013.01); *A61F 2002/3055* (2013.01); *A61F 2002/30471* (2013.01); *A61F 2002/30556* (2013.01); *A61F 2002/30884* (2013.01); *A61F 2002/30891* (2013.01); *A61F 2002/4415* (2013.01); *A61F 2002/4445* (2013.01); *A61F 2002/4698* (2013.01)

(58) Field of Classification Search
None
See application file for complete search history.

(56) References Cited

U.S. PATENT DOCUMENTS

| 8,512,408 | B2 | 8/2013 | Miller et al. |
| 8,685,095 | B2 | 4/2014 | Miller et al. |
| 2007/0191951 | A1 | 8/2007 | Branch |
| 2014/0012383 | A1 | 1/2014 | Triplett et al. |
| 2015/0313719 | A1 | 11/2015 | Perloff et al. |
| 2017/0056200 | A1* | 3/2017 | Koch ........................ A61F 2/44 |

* cited by examiner

*Primary Examiner* — Sameh R Boles
(74) *Attorney, Agent, or Firm* — Riverside Law LLP

(57) ABSTRACT

The present invention provides expandable devices and insertion tools for deploying the expandable devices. The expandable devices are capable of increasing in height and width when expanded from a closed configuration to an open configuration to occupy a larger volume and to present a larger surface area. The expandable devices are lockable and are capable of rigidly occupying a space after expansion. In some embodiments, the expandable devices are useful as interbody devices for spinal fusions.

20 Claims, 40 Drawing Sheets

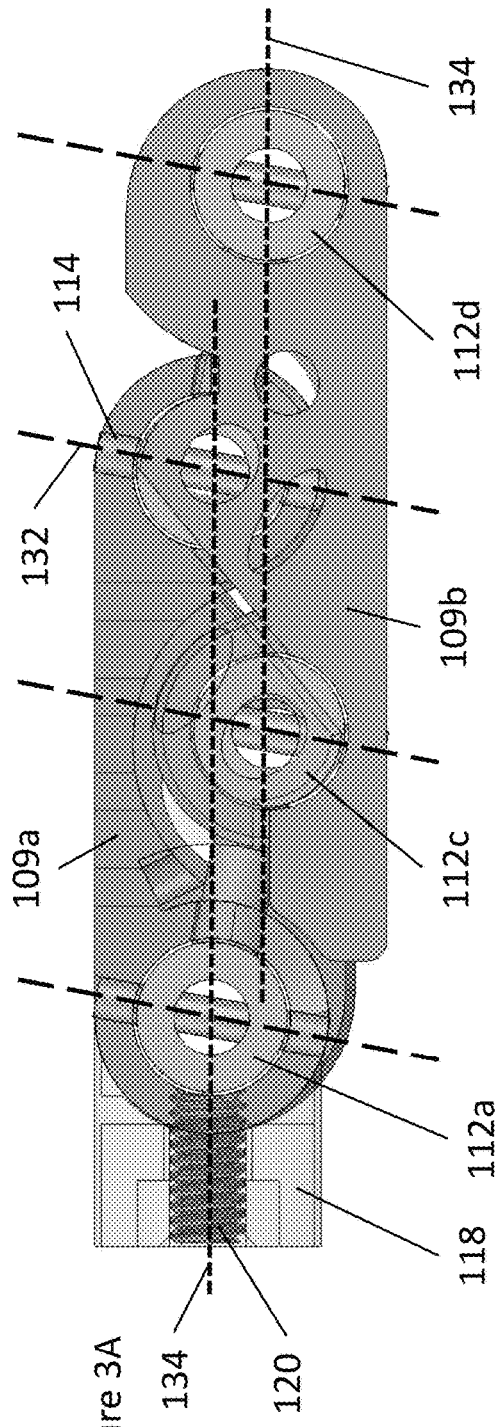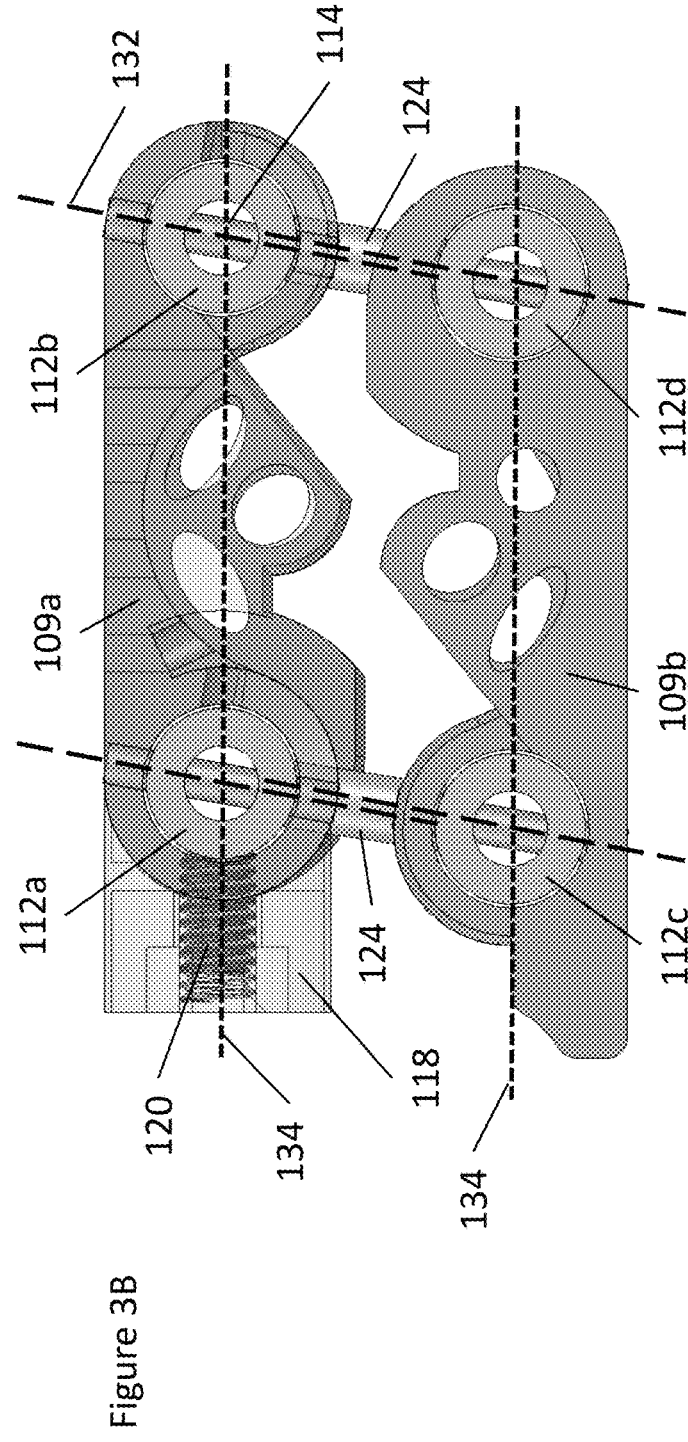
Figure 3A
Figure 3B

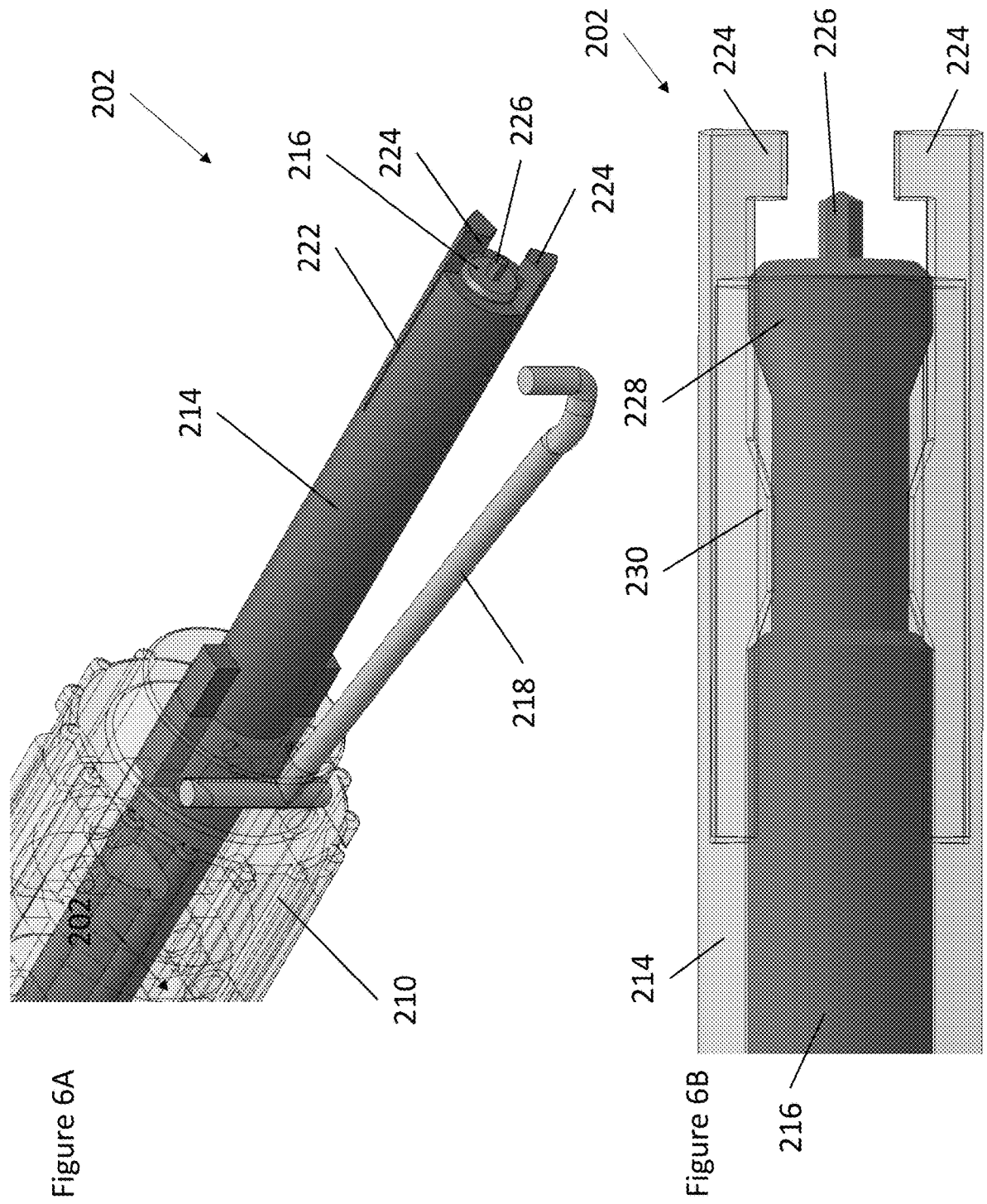

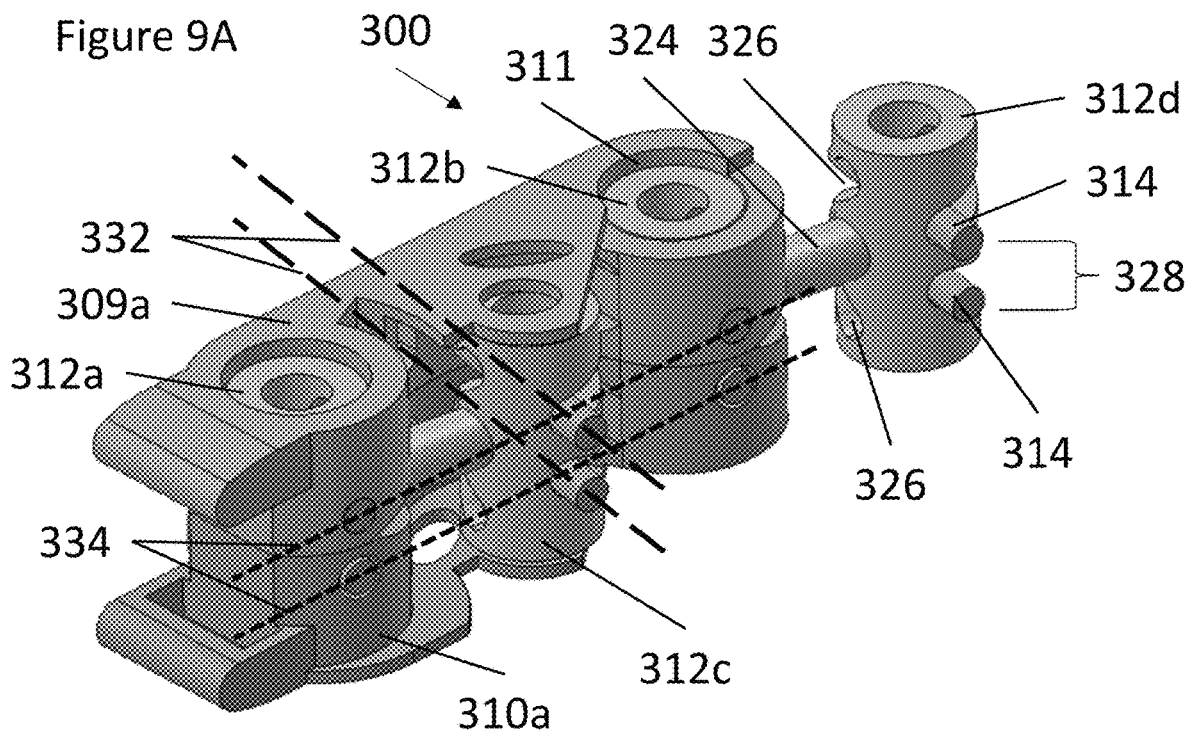
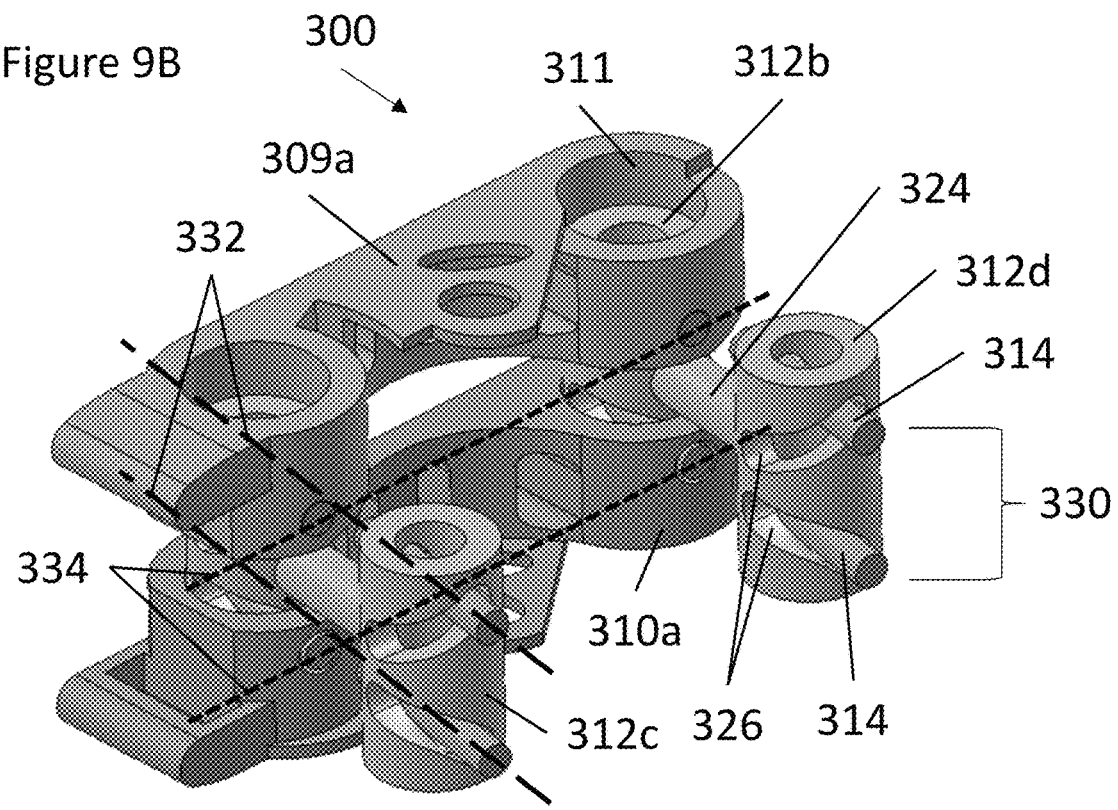

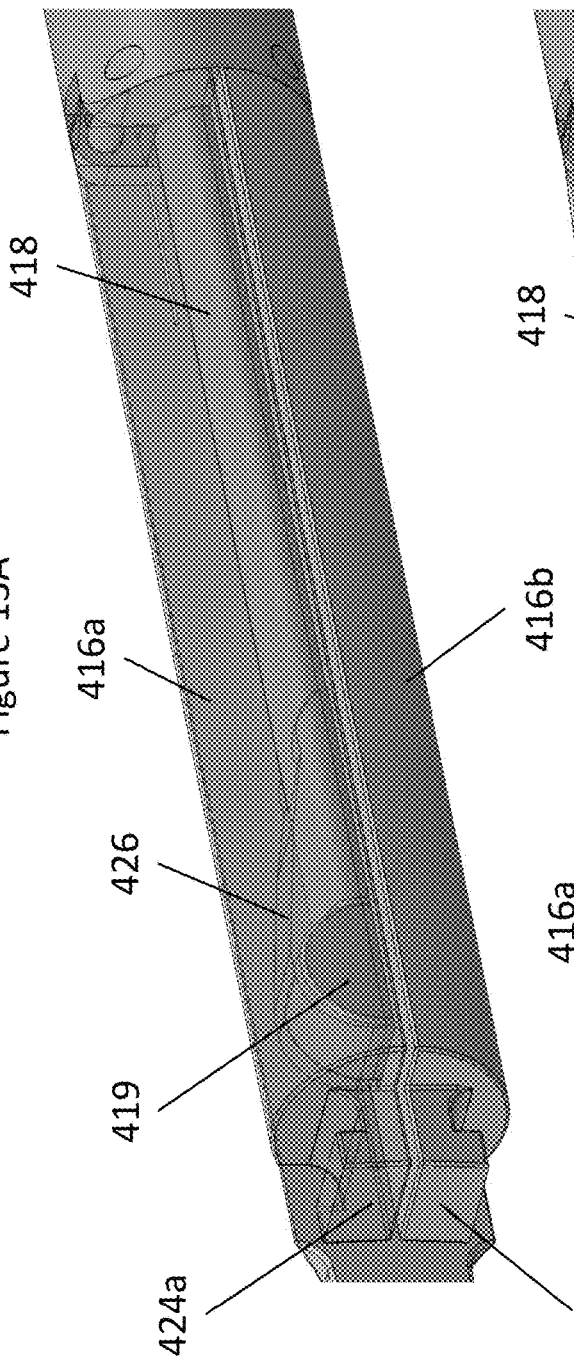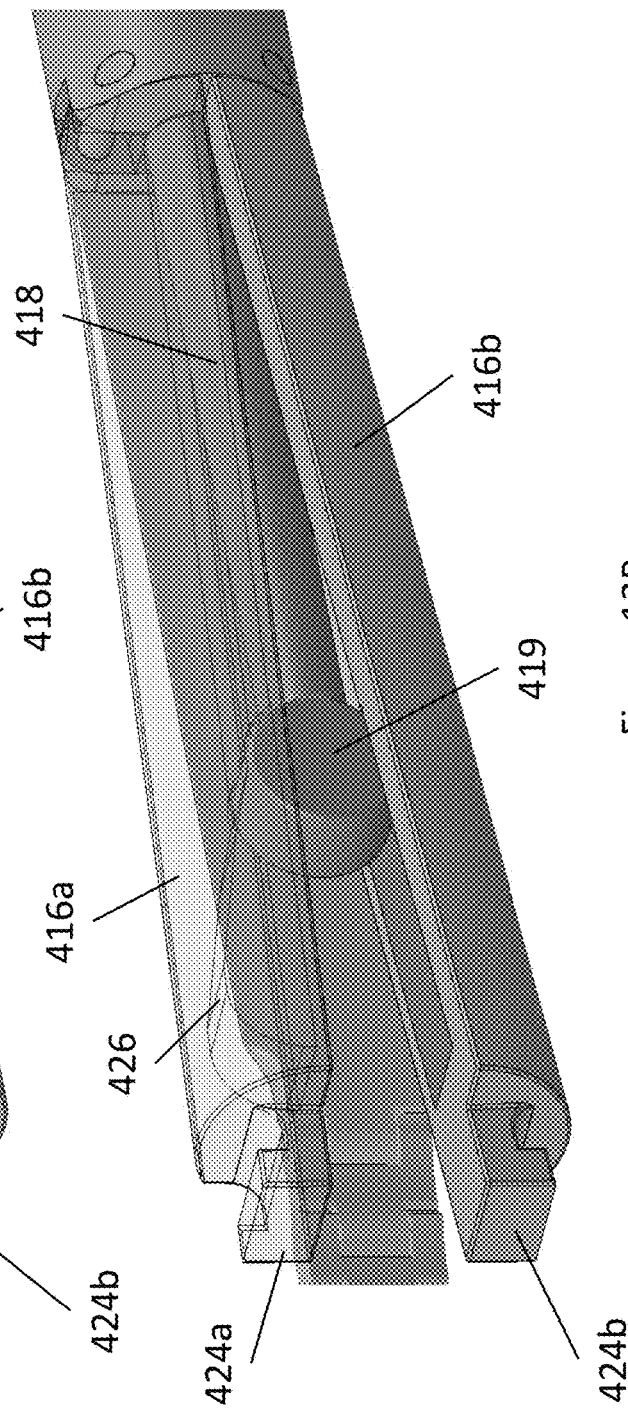

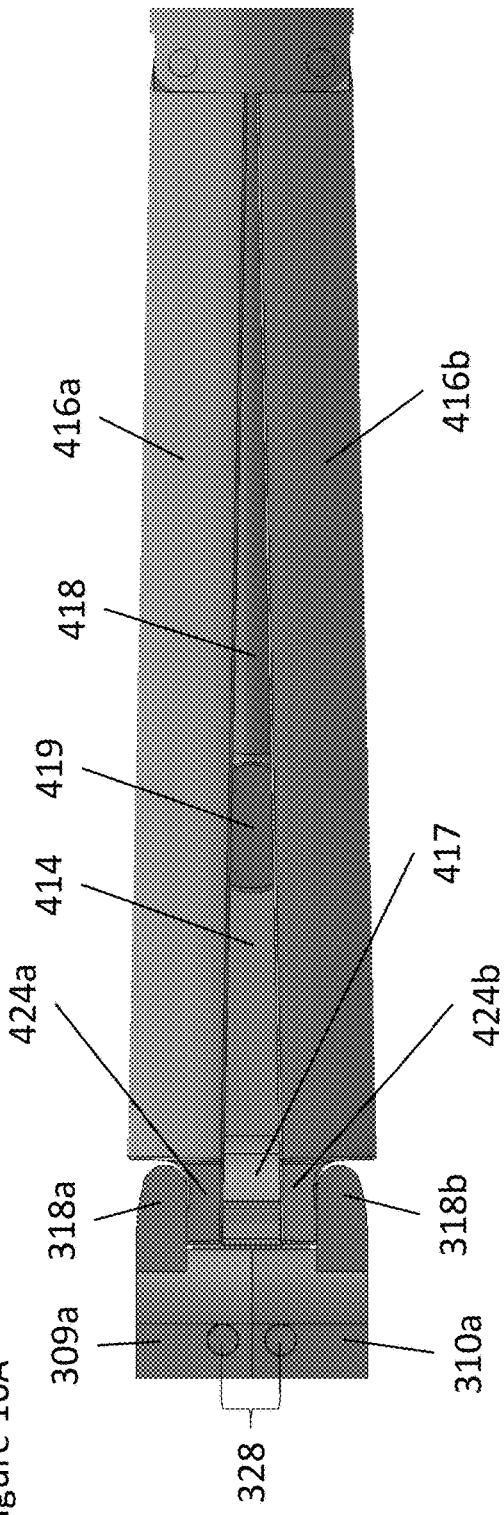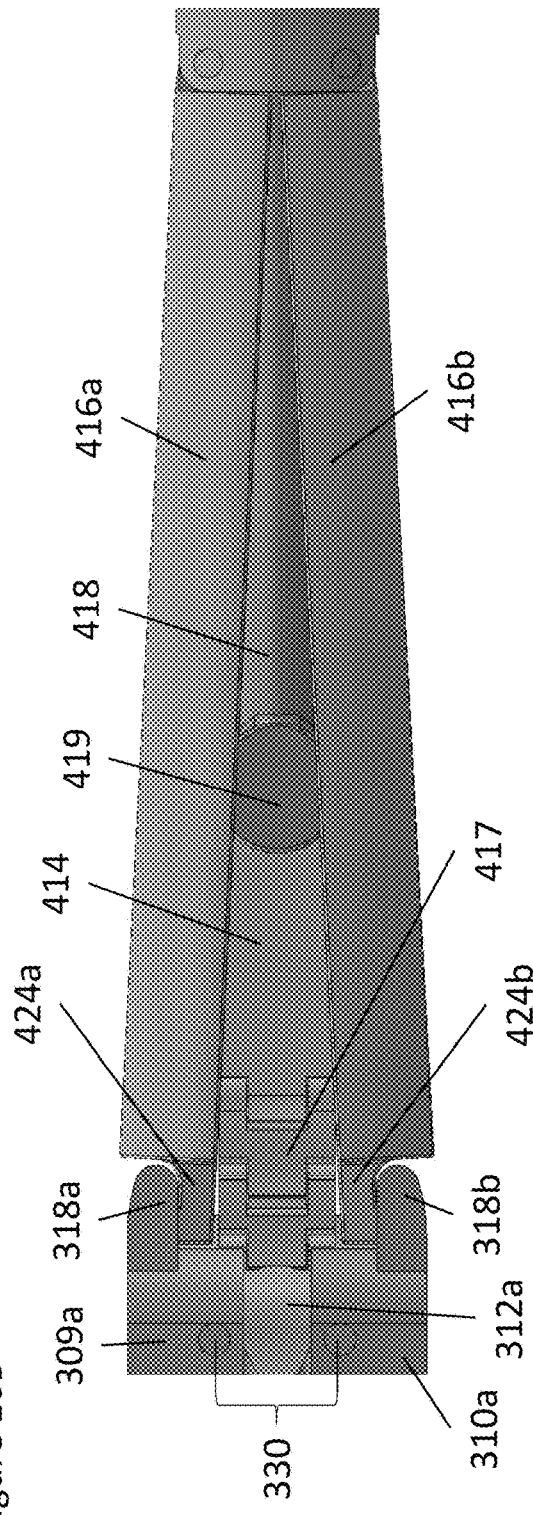

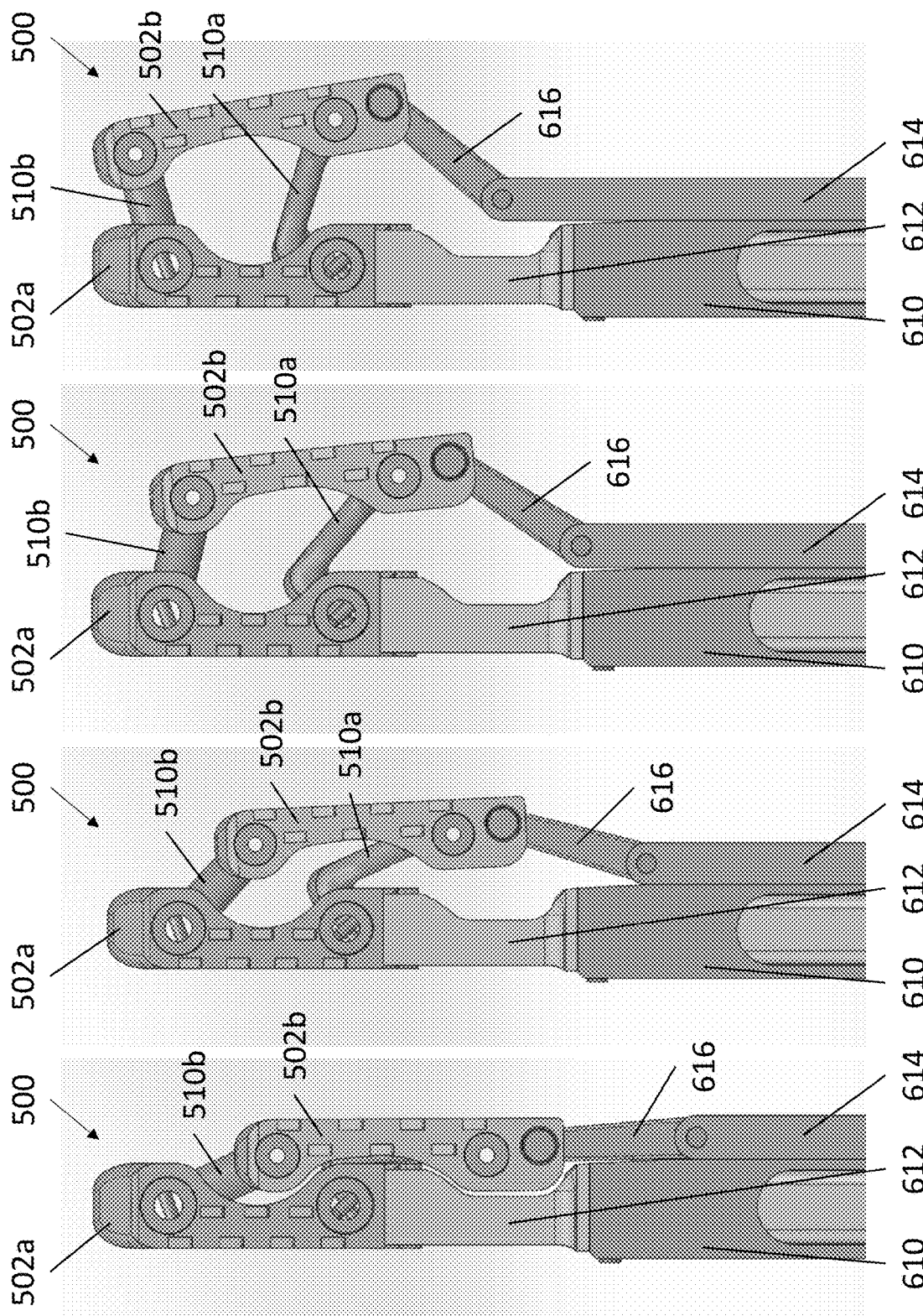

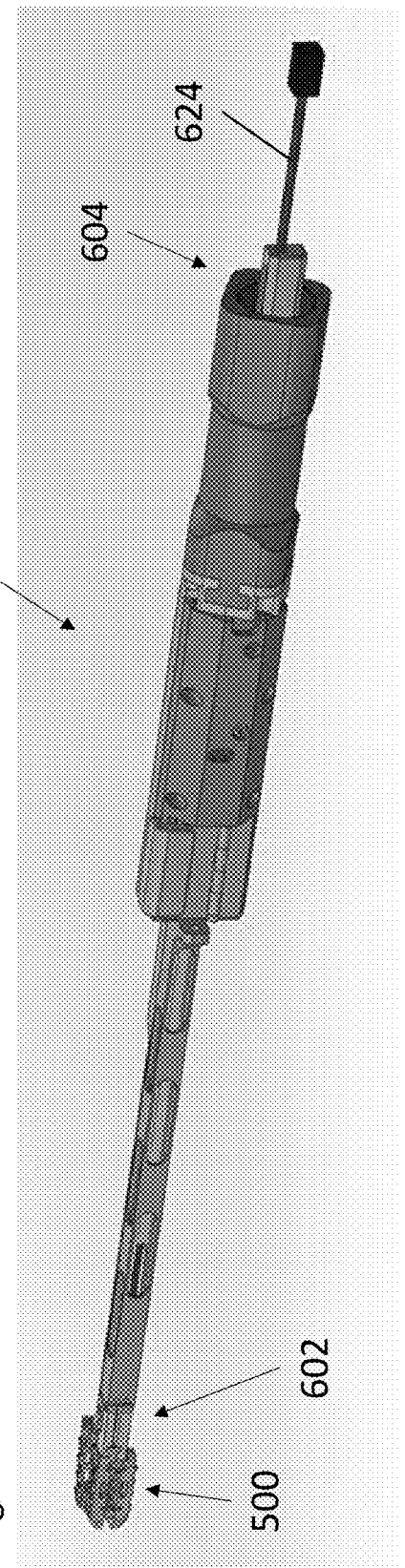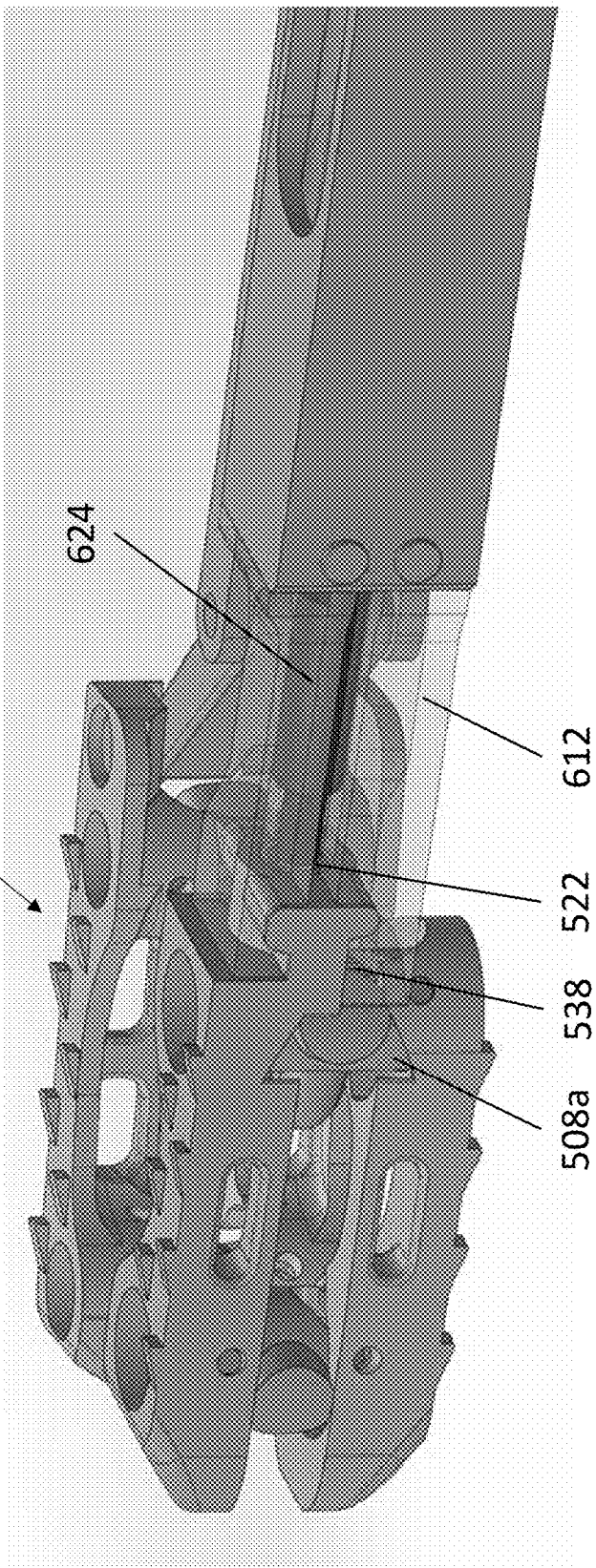

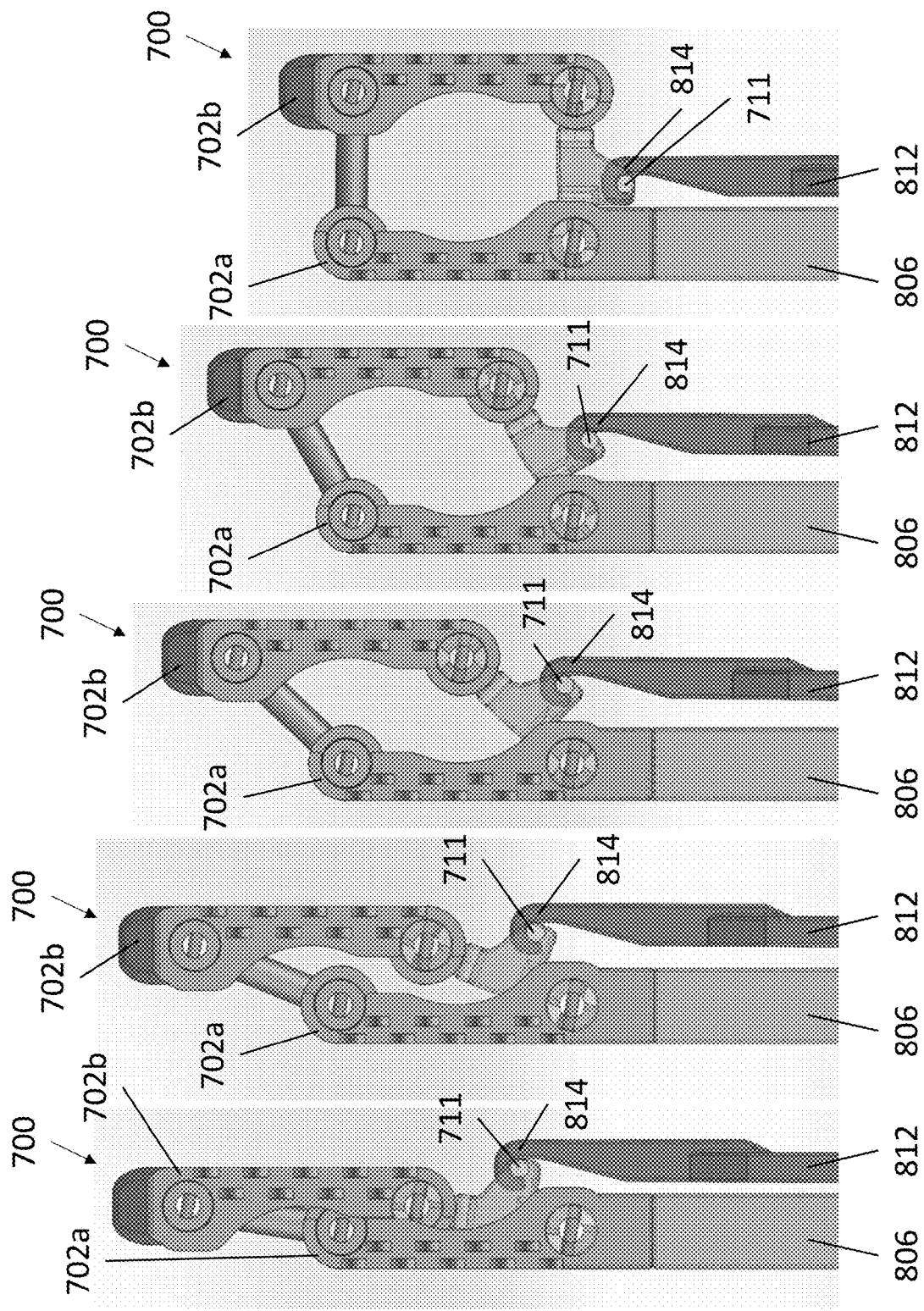

EXPANDABLE DEVICE

CROSS-REFERENCE TO RELATED APPLICATIONS

This application is a U.S. national phase application filed under 35 U.S.C. § 371 claiming benefit to International Patent Application No. PCT/US18/53716, filed Oct. 1, 2018, which is entitled to priority under 35 U.S.C. § 119(e) to U.S. Provisional Patent Application No. 62/565,374, filed Sep. 29, 2017, the contents of which are each incorporated by reference herein in their entirety.

BACKGROUND OF THE INVENTION

Certain spinal fusion procedures remove degenerated intervertebral disc material and pack the intervertebral space to maintain the separation between adjacent vertebrae. While some procedures pack the intervertebral space with bone-forming tissue, other procedures insert rigid devices for more reliable separation of the vertebrae. In the interest of reducing recovery time and surgical tissue damage, it is advantageous for a rigid device insert to possess a small profile to fit through a minimally invasive incision, while also possessing a large footprint to maximize stability in the intervertebral disc space.

Thus, there is a need in the art for small profile rigid devices that are able to expand to occupy a larger footprint. The present invention satisfies this need.

SUMMARY OF THE INVENTION

In one aspect, the present invention relates to an expandable device, comprising: a first and a second superior arm and a first and a second inferior arm, each arm having an anterior and a posterior end and a top and a bottom surface, and each arm having an anterior and posterior opening through the top and bottom surface, wherein the first superior arm is positioned over the first inferior arm with anterior and posterior openings in alignment, and the second superior arm is positioned over the second inferior arm with anterior and posterior openings in alignment; four cylindrical bolts positioned within each of the openings of the arms, each bolt having a top end, a bottom end, an outer surface, and a first, a second, a third, and a fourth slot within the outer surface; wherein the first and second slot of each bolt are positioned opposite from each other and each extend from near the middle of each bolt towards the top end of each bolt, and the third and fourth slots of each bolt are positioned opposite from each other and extend from near the middle of each bolt towards the bottom end of each bolt; a first rod connecting each of the bolts positioned within the anterior openings of the arms, and a second rod connecting each of the bolts positioned within the posterior openings of the arms; and a plurality of pins, each pin connected to an inner surface of each of the openings of the arms and slidably engaged to a slot of the bolt positioned within the respective opening.

In one embodiment, each of the four arms are substantially parallel to each other in a closed configuration. In one embodiment, the four arms are movable about the four bolts while maintaining substantially parallel alignment to each other.

In one embodiment, the first and second slots of each bolt extend in a curve from near the middle of each bolt for about 90 degrees around the outer surface towards the top end of each bolt, and wherein the third and fourth slots of each bolt extend in a curve from near the middle of each bolt for about 90 degrees around the outer surface towards the bottom end of each bolt In one embodiment, the device comprises a closed configuration that positions the four arms adjacent to each other and positions the plurality of pins near the middle of each bolt. In one embodiment, the device comprises an open configuration that positions the four arms away from each other and positions the plurality of pins near the top and bottom ends of each bolt.

In one embodiment, at least one arm comprises a locking bit drivable into a bolt. In one embodiment, each arm comprises one or more cavities. In one embodiment, the cavities are prefilled with bone tissue. In one embodiment, the cavities are prefilled with a therapeutic selected from the group consisting of: a population of stem cells, an anti-inflammatory, an antibiotic, and an antiviral. In one embodiment, the cavities are sized to fit a sensor selected from the list consisting of: a temperature sensor, a pressure sensor, a corrosion sensor, and a gyroscope. In one embodiment, the device is sized to fit within an intervertebral disc space.

In one embodiment, the first superior arm comprises a connector extending from its posterior end, and the second superior arm comprises a socket extending from its posterior end. In one embodiment, the first superior arm and the first inferior arm each comprises a connector extending from its posterior end. In one embodiment, the first superior arm comprises a connector extending from its posterior end, and the second rod comprises a rung.

In another aspect, the present invention relates to an insertion tool for expanding the expandable device of the present invention, comprising: a tubular housing comprising a rotating section, a nonrotating section, and a lumen running throughout; an elongate clamp positioned within the lumen extending from the tubular housing in an anterior direction, the clamp engageable to the connector of the first superior arm; and an anchor rod secured to the nonrotating section in an anterior direction, the anchor rod engageable to the socket of the second superior arm.

In one embodiment, the anchor rod holds the second superior arm in a static position while the clamp is movable in a posterior and an anterior direction to move the first superior arm. In one embodiment, the clamp is movable by actuating the rotating section of the housing. In one embodiment, the insertion tool further comprises a bit driver engageable to a locking bit positioned in the connector of the first superior arm.

In another aspect, the present invention relates to an insertion tool for expanding the expandable device of the present invention, comprising: a tubular housing comprising a posterior rotating section, an anterior hinged section splitting the housing into an upper half connectable to the connector of the first superior arm and a lower half connectable to the connector of the first inferior arm, and a lumen running throughout the tubular housing; a wedge rod positioned within the lumen, the wedge rod comprising an anterior wedge head positioned within the lumen of the hinged section; and an elongate hooked member slidable along the exterior of the tubular housing, the elongate hooked member comprising an anterior hook engageable to the second rod of the expandable device.

In one embodiment, the wedge rod is movable in a posterior direction to open the hinged section using the wedge head and spread apart a connected first superior arm and first inferior arm of the expandable device. In one embodiment, the wedge rod is movable by actuating the rotating section of the housing. In one embodiment, the elongate hooked member is movable in a posterior direction to pull on an engaged second rod of the expandable device. In one embodiment, the movement of the elongate hooked member is coupled to the movement of the wedge rod. In one embodiment, the coupled movement of the elongate hooked member and the wedge rod simultaneously spreads apart a connected first superior arm and first inferior arm and pulls on an engaged second rod of the expandable device.

In another aspect, the present invention relates to an insertion tool for expanding the expandable device of the present invention, comprising: a tubular housing having a rotating section, a nonrotating section, and a lumen running throughout; an expandable pair of tongs extending from the nonrotating section in an anterior direction, the tongs engageable to the connector of the first superior arm; a locking sleeve slidable over the pair of tongs; and an elongate deployment driver positioned within the lumen of the housing, the deployment driver having an anterior pin engageable to the socket of the second superior arm.

In one embodiment, positioning the locking sleeve in an anterior-most position secures the pair of tongs to the connector of the first superior arm, holding it in a static position while the deployment driver is movable in a posterior and an anterior direction to move the second superior arm. In one embodiment, the deployment driver is movable by actuating the rotating section of the housing. In one embodiment, the pair of tongs comprises a lumen sized to fit a bit driver engageable to a locking bit positioned in the connector of the first superior arm.

In another aspect, the present invention relates to an insertion tool for expanding the expandable device of the present invention, comprising: an elongate shaft having an engagement member positioned at an anterior end; and an elongate pull rod adjacent to the elongate shaft, the pull rod having an anterior hook engageable to the rung of the second rod of the expandable device.

In one embodiment, the shaft holds the first superior arm in a static position while the pull rod is movable in a posterior direction to pull on the second rod of the expandable device. In one embodiment, the engagement member comprises a screw. In one embodiment, the pull rod is replaceable with an elongate push rod having an anterior stirrup engageable to the rung of the second rod of the expandable device.

BRIEF DESCRIPTION OF THE DRAWINGS

The following detailed description of exemplary embodiments of the invention will be better understood when read in conjunction with the appended drawings. It should be understood, however, that the invention is not limited to the precise arrangements and instrumentalities of the embodiments shown in the drawings.

FIG. 1A and FIG. 1C depict the device in a closed configuration. FIG. 1B and FIG. 1D depict the device in an open configuration.

In FIG. 2A, the top image depicts two bolts connected by a rod, the bottom left image depicts one bolt and the closed position of each pin guide, and the bottom right image depicts the same bolt rotated by about 90 degrees to show the open position of each pin guide. In FIG. 2B and FIG. 2C, external components of the device have been removed to show the movement of internal components.

FIG. 3A and FIG. 3B depict top down views of an exemplary expandable device and a locking mechanism.

FIG. 6A and FIG. 6B depict various views of the anterior tip of an exemplary insertion tool.

FIG. 9A and FIG. 9B depict perspective views of an exemplary expandable device in a closed configuration (FIG. 9A) and in an open configuration (FIG. 9B) with external components removed to show the movement of internal components.

FIG. 13A and FIG. 13B depict partially wireframe views of an exemplary insertion tool wedge system in a closed (FIG. 13A) and an open (FIG. 13B) configuration.

FIG. 16A and FIG. 16B depict an exemplary insertion tool engaged to an exemplary expandable device (FIG. 16A) and the insertion tool having opened the expandable device (FIG. 16B).

FIG. 25A through FIG. 25D depict a sequence of using an exemplary insertion tool to shift an exemplary expandable device from a closed configuration to an open configuration.

FIG. 26A and FIG. 26B depict the use of a locking driver with an exemplary insertion tool to lock an exemplary expandable device in an open configuration.

FIG. 31A through FIG. 31E depict a sequence of using an exemplary insertion tool to shift an exemplary expandable device from a closed configuration to an open configuration.

DETAILED DESCRIPTION

Figure 1A:
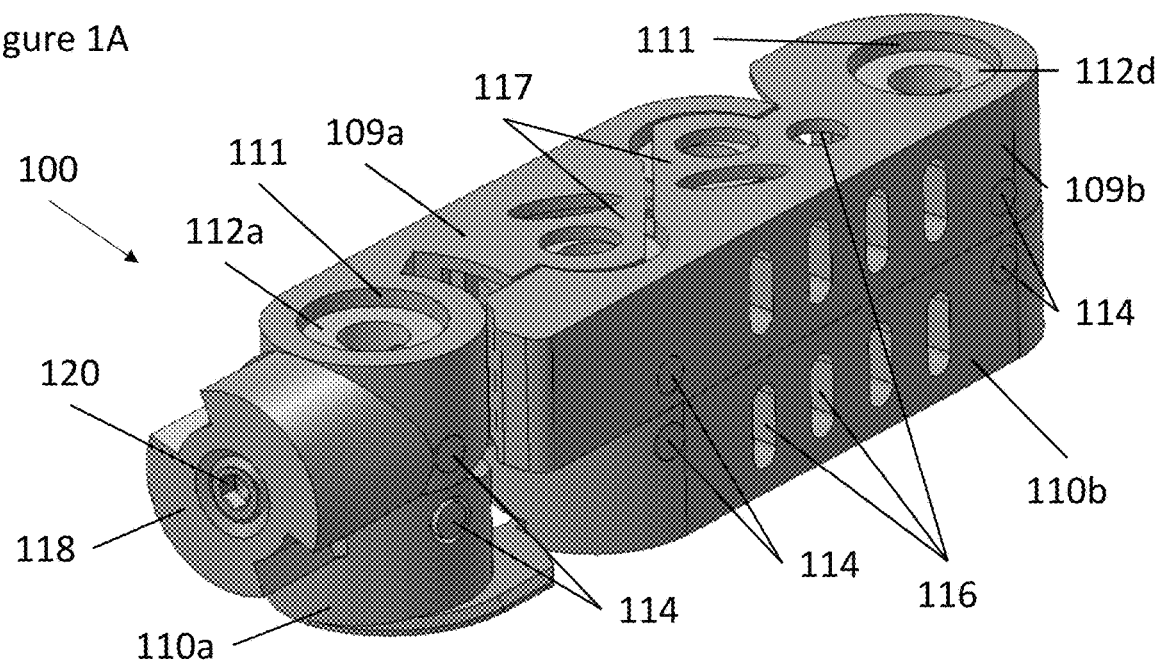
FIG. 1A through FIG. 1D depict perspective views of an exemplary expandable device.

The present invention provides expandable devices and insertion tools for deploying the expandable devices. The expandable devices are capable of increasing in height and width when expanded from a closed configuration to an open configuration to occupy a larger volume and to present a larger surface area. The expandable devices are lockable and are capable of rigidly occupying a space after expansion. In some embodiments, the expandable devices are useful as interbody devices for spinal fusions.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

First Expandable Device

Referring now to FIG. 1A through FIG. 1D, an exemplary expandable device 100 is depicted. Expandable device 100 comprises four arms (superior first arm 109a, superior second arm 109b, inferior third arm 110a, and inferior fourth arm 110b) and four movable bolts 112 (referred to herein as posterior first bolt 112a, anterior second bolt 112b, posterior third bolt 112c, and anterior fourth bolt 112d). Each arm comprises two slots 111 sized to fit a movable bolt 112. Each bolt 112 is secured within a slot 111 by a pin 114 fixed to each arm, and bolts 112a-112d are secured in pairs by a connecting rod 124 (112a connected to 112c, 112b connected to 112d), described elsewhere herein.

Arms 109a, 109b, 110a, 110b, bolts 112a-112d, and pins 114 are preferably constructed from a rigid material, such as a metal or a hard polymer. In various embodiments, the rigid material is a biocompatible material. In certain embodiments, each arm can comprise a surface that is textured or at least partially covered with barbs or spikes to improve the attachment of expandable device 100 within a space.

In various embodiments, each arm can comprise a plurality of cavities 116. Cavities 116 may be placed throughout each arm without compromising the rigidity of expandable device 100. Cavities 116 can be filled with any component that is synergistic with the function of expandable device 100. For example, in some embodiments, cavities 116 can be packed with a biological material to promote the ingrowth of tissue, such as bone. In some embodiments, cavities 116 can be packed with a therapeutic to treat surrounding tissue. In some embodiments, one or more sensors can be inserted into cavities 116 to monitor the device and its environs, such as a temperature sensor, pressure sensor, corrosion sensor, and the like. In some embodiments, cavities 116 can be used to secure expandable device 100 within a space, by accepting screws or cement. Cavities 116 can also be used to view and monitor the progress of bone growth into the interior of expandable device 100.

In various embodiments, each arm can comprise one or more fins 117 to increase the surface area of the top and bottom of expandable device 100. Fins 117 can be sized to interlock when expandable device 100 is closed to decrease the footprint of expandable device 100.

In some embodiments, an arm may further comprise features for engaging an insertion tool, described elsewhere herein. For example, arm 109a can comprise connector 118 having a threaded interior sized to fit a locking bit 120. Connector 118 comprises one or more attachment features 119 to mate with the insertion tool. Attachment features 119 may be indents as shown in FIG. 1C and FIG. 1D to fit the clamp of an insertion tool. Alternatively, attachment features 119 may be threads to threadably engage an insertion tool. Locking bit 120 can be actuated to lock into a bolt 112, thereby arresting movement in expandable device 100 (FIG. 3A, FIG. 3B). In another example, arm 109*b* can comprise socket 122 to fit the rod of an insertion tool, described elsewhere herein.

Figure 2A:
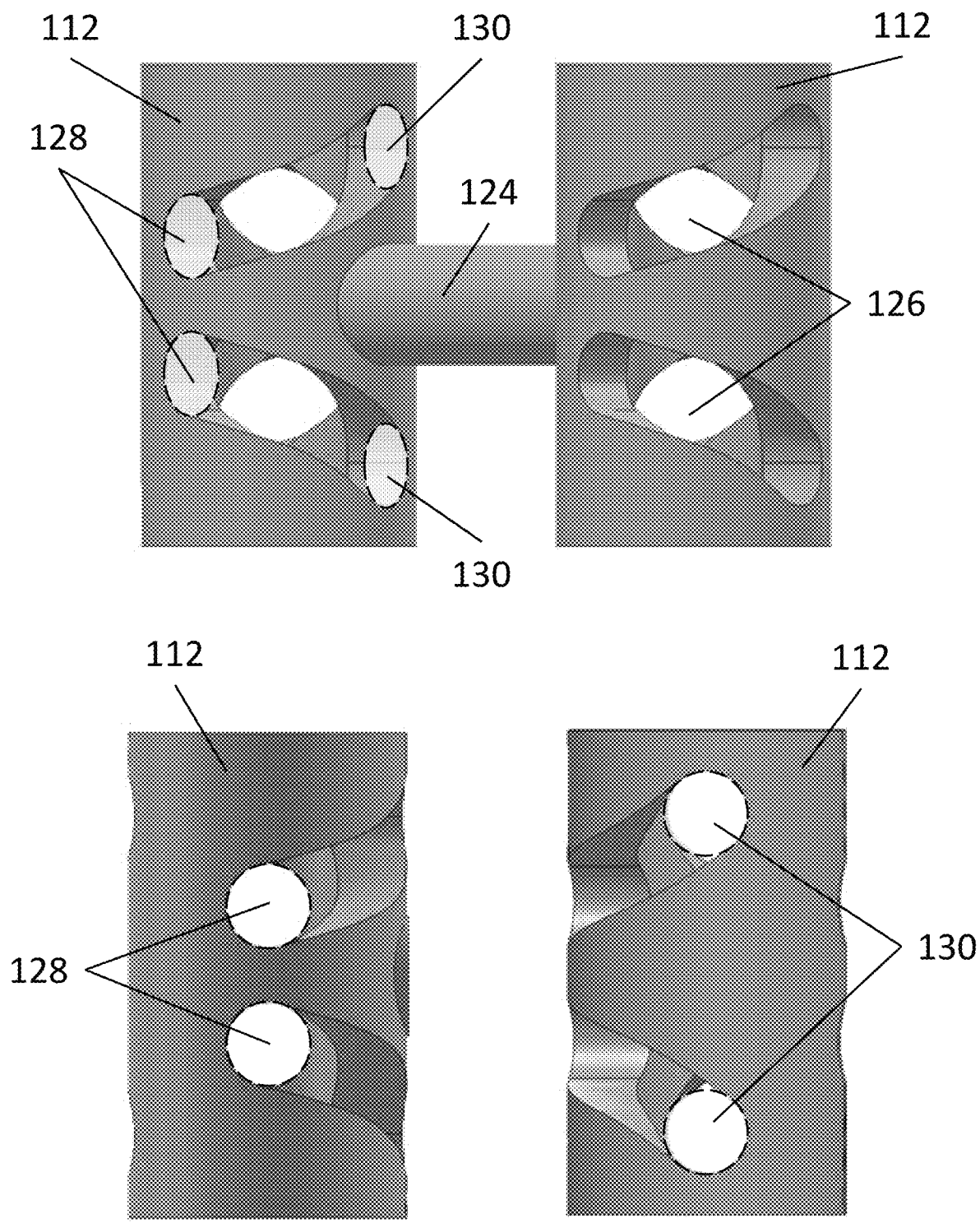
FIG. 2A through FIG. 2C depict views of the bolts of an exemplary expandable device and the pin guides within the bolts that are used to open and close the device.
Figure 2B:
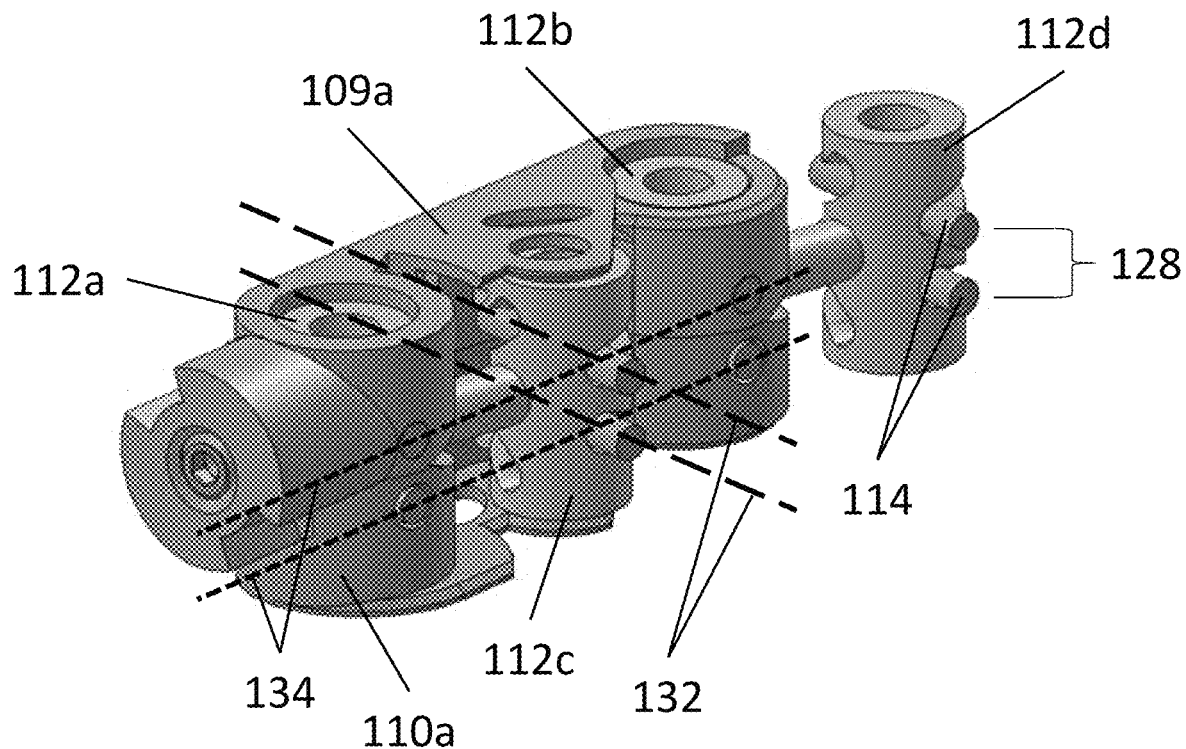
Figure 2C:
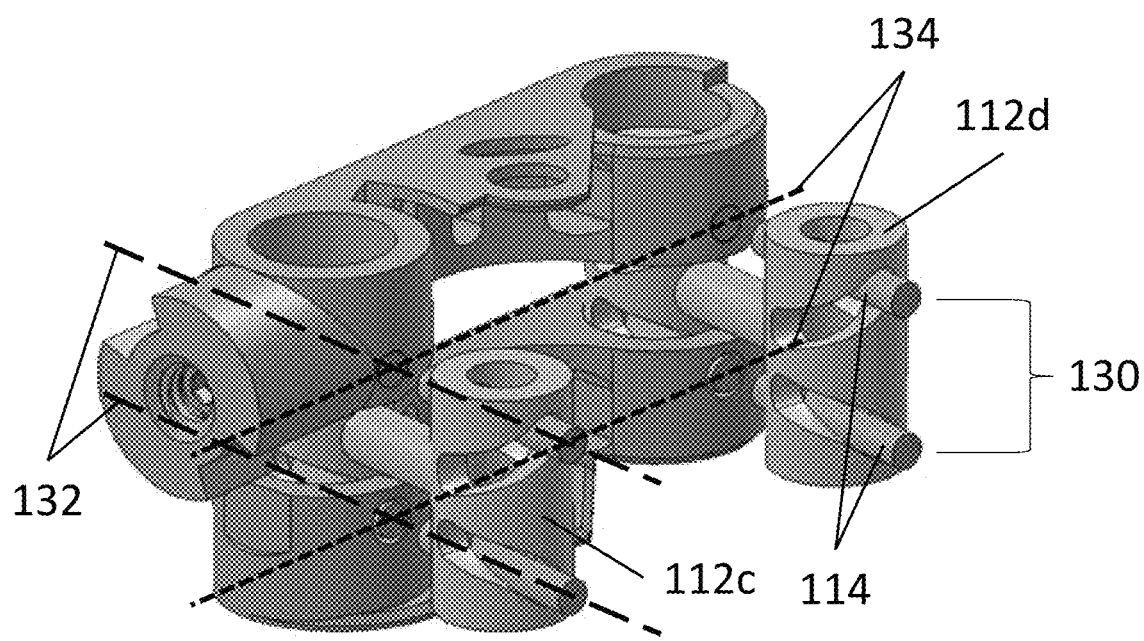

Referring now to FIG. 2A through FIG. 2C, bolts 112 are depicted. Bolts 112 are paired together by way of connecting rod 124. Each bolt 112 comprises a cylindrical shape having a top end, a bottom end, and an outer surface. Each bolt 112 comprises four pin guides 126 cut into the outer surface. Each pin guide 126 is a curved slot having a closed position 128 near the center of bolt 112 and an open position 130 near the top and bottom ends of bolt 112. Closed position 128 and open position 130 are placed about 90 degrees away from each other on the outer surface. Pin guides 126 are arranged on bolt 112 in opposing pairs on the top half and the bottom half of bolt 112, such that a pin 114 can extend through an opposing pair of pin guides 126.

In FIG. 2B and FIG. 2C, expandable device 100 is depicted without arms 109*b* and 110*b* to illustrate the arrangement of bolts 112*a*-112*d* and the mechanism by which bolts 112*a*-112*d*, pins 114, and the arms open and close in a synchronized manner. In this embodiment, each arm 109*a*, 109*b*, 110*a*, and 110*b* is aligned in parallel or substantially in parallel with each other (visualized by arm axes 134 running through the lengths of each arm), and each arm comprises a fixed pin 114 passing through an opposing pair of pin guides 126 to secure a bolt 112 into each of its two slots 111. Pins 114 are fixed relative to each of the arms, such that each pin 114 is arranged in parallel or substantially in parallel to each other (visualized by pin axes 132 running through the lengths of each pin 114). Rotating a bolt 112 slides pin 114 within pin guide 126 between a closed position 128 and an open position 130. The height difference between closed position 128 and open position 130 thereby increases the distance between pins 114, which also separates the superior arms 109*a* and 109*b* from the inferior arms 110*a* and 110*b*. FIG. 3A and FIG. 3B illustrate that shifting expandable device 100 between a closed configuration and an open configuration also maintains the parallel alignment between arm 109*a* (and arm 110*a* underneath) on one side and arm 109*b* (and arm 110*b* underneath) on the opposite side (visualized by the parallel arm axes 134) as well as between pins 114 (visualized by the parallel pin axes 132). FIG. 3A and FIG. 3B also illustrate that shifting expandable device 100 between a closed configuration and an open configuration induces a separation in distance between arms 109*a* and 110*a* on one side and arms 109*b* and 110*b* on the opposite side due to the length of the connecting rods 124.

Figure 1B:
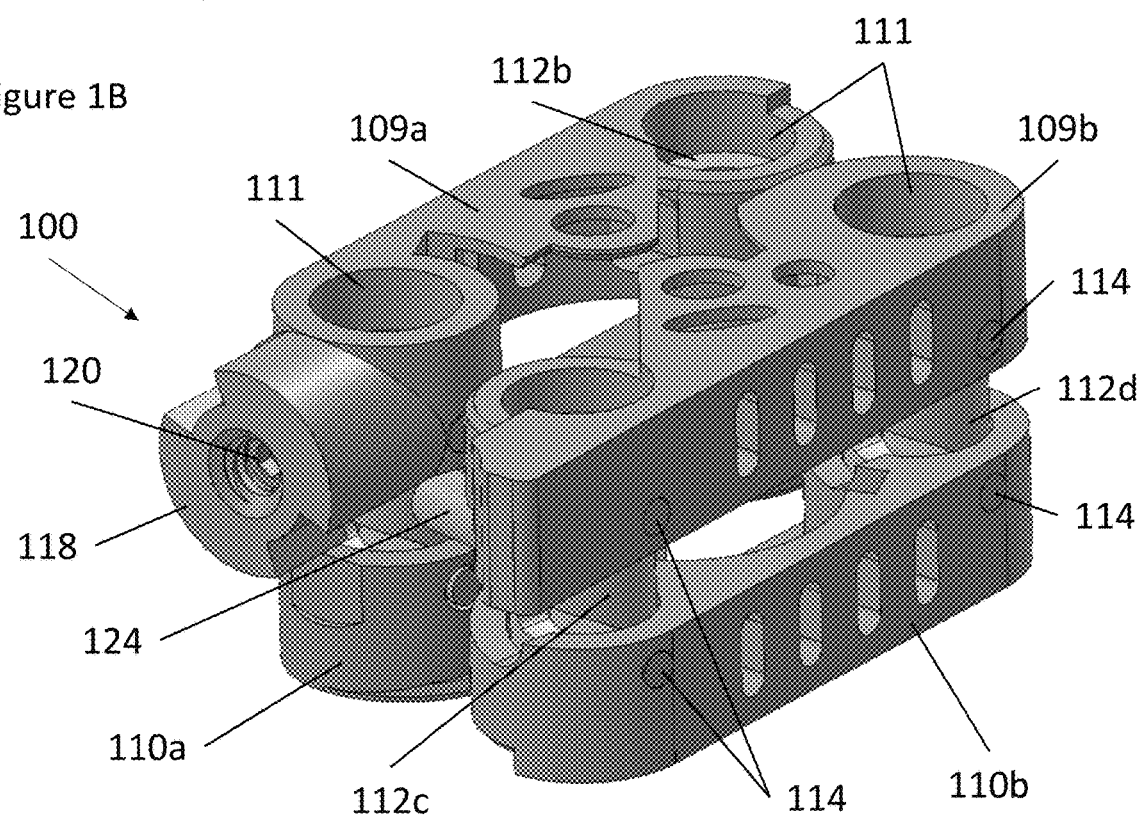
Figure 1C:
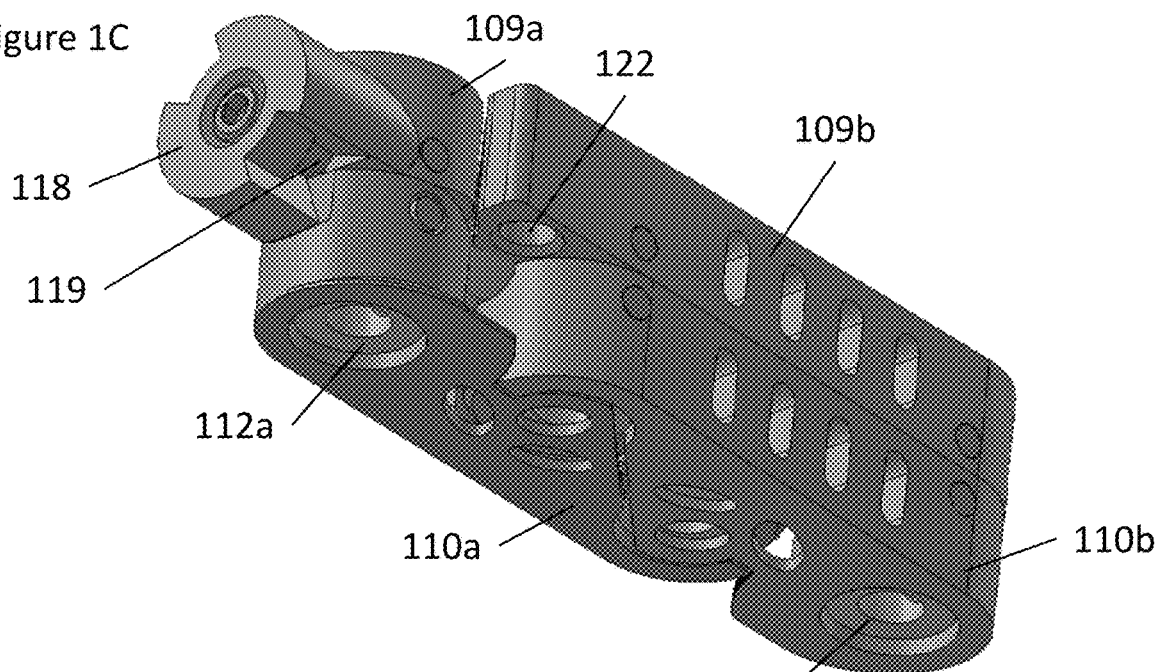
Figure 1D:
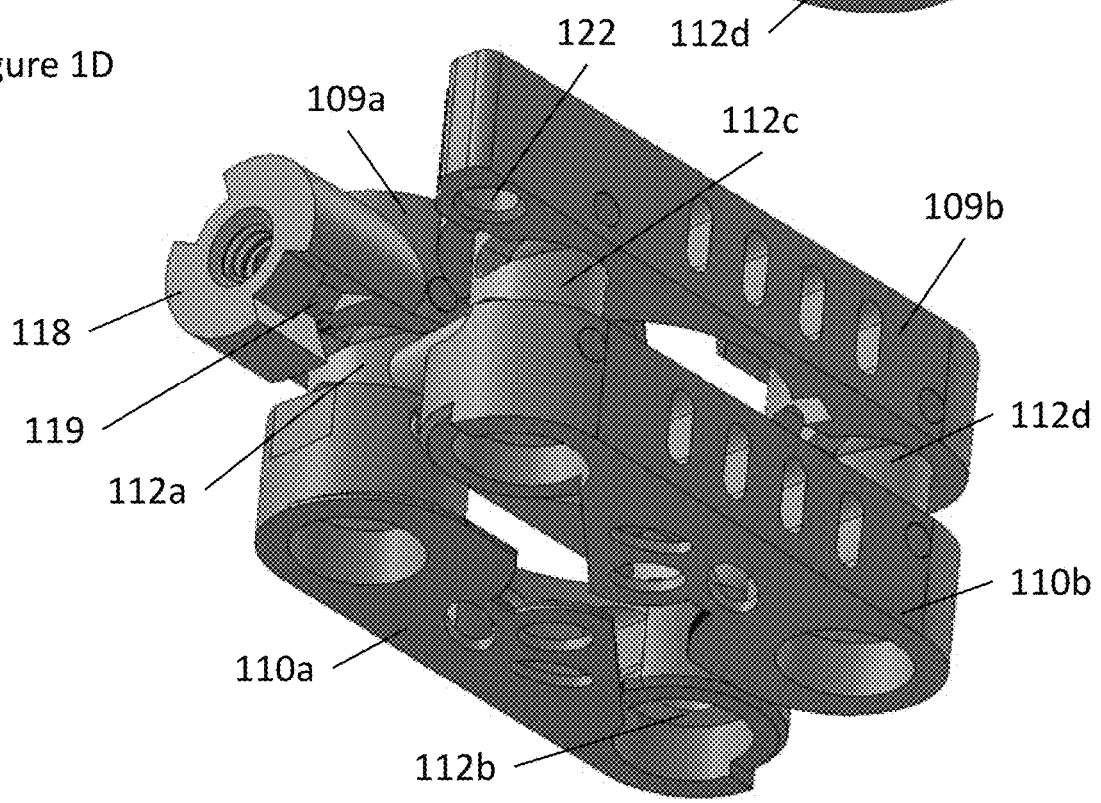

The exemplary expandable device 100 is depicted as having a polyhedron-like shape with four rectangular sides and a parallelogram-like top and bottom when closed (FIG. 1A), and a polyhedron-like shape with four rectangular sides and a rectangular top and bottom when open (FIG. 1B). However, it should be understood that expandable device 100 is not limited to the depicted shapes, and can have any suitable shape. For example, each of the arms can comprise a semicircular shape to give expandable device 100 an overall cylindrical shape having curved sides and a circular or oval top and bottom.

In some embodiments, one or more of the connecting rods 124 can have a different length (not pictured). For example, bolt 112*a* and bolt 112*c* can be joined by a connecting rod 124 having a first length, and bolt 112*c* and bolt 112*d* can be joined by a connecting rod 124 having a second length, such that arms 109*a* and 110*a* are separated from the opposing arms 109*b* and 110*b* by the first length at one end and by a second length at an opposing end. In this manner, expandable device 100 can thereby maintain a substantially rectangular top and bottom when closed, and has a substantially trapezoidal top and bottom when open.

In some embodiments, one or more of the bolts 112 can have pin guides 126 with different open positions 130 (not pictured). For example, bolt 112*a* and bolt 112*c* can each have pin guides 126 with an open position 130 at a first height, and bolt 112*b* and bolt 112*d* can each have pin guides 126 with an open position 130 at a second height, such that superior arms 109*a* and 109*b* are separated from inferior arms 110*a* and 110*b* by a first height at one end and by a second height at an opposing end. In this manner, expandable device 100 can thereby maintain substantially rectangular sides when closed, and has a lordotic angle with a substantially trapezoidal left and right side when open.

Expandable device 100 can have any suitable dimensions between its closed and open configurations. For example, in certain embodiments, expandable device 100 can have a closed length of between 30 mm to 30 cm, a closed width of between 7 mm to 7 cm, and a closed height of between 8 mm and 8 cm. In certain embodiments, expandable device 100 can have an open length of between 20 mm to 20 cm, an open width of between 10 mm to 10 cm, and an open height of between 10 mm and 10 cm. The surface area and footprint of expandable device 100 will depend on the length, width, and height, and will change accordingly between open and closed configurations. The surface area of expandable device 100 will further depend on modifications to expandable device 100, such as the number of cavities 116 and the size and overlapping of fins 117. In one embodiment, an exemplary expandable device 100 has a closed length, width, and height of 34.81 mm, 7.94 mm, and 8 mm; an open length, width and height of 27.36 mm, 17.27 mm, and 10.63 mm; a closed footprint and footprint surface area of 221.16 mm$^2$ and 165.84 mm$^2$; and an open footprint and footprint surface area of 361.68 mm$^2$ and 184.02 mm$^2$.

First Insertion Tool for the First Expandable Device

Figure 4:
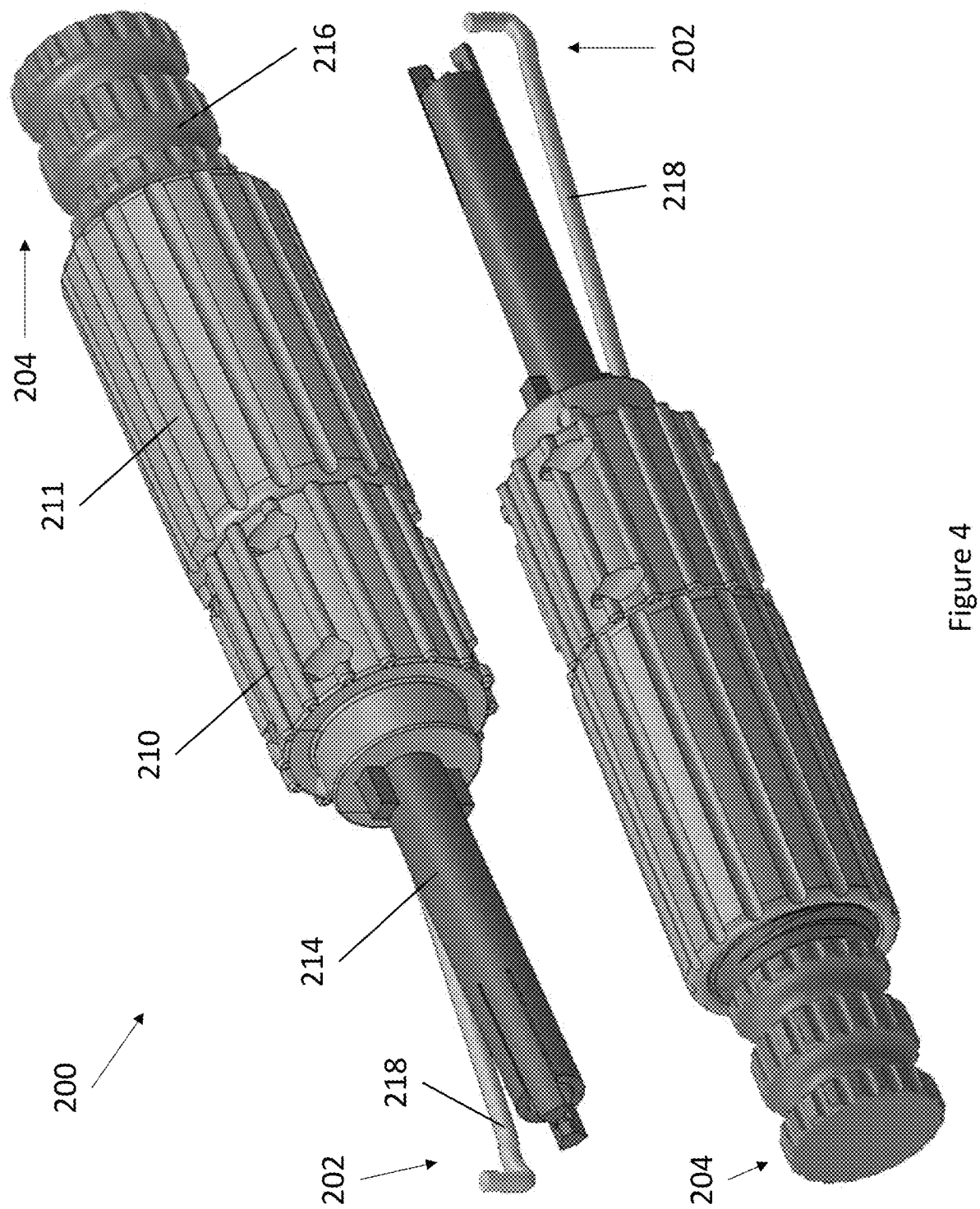
FIG. 4 depicts perspective views of an exemplary insertion tool for deploying an expandable device of the present invention.
Figures 5A, 5B:
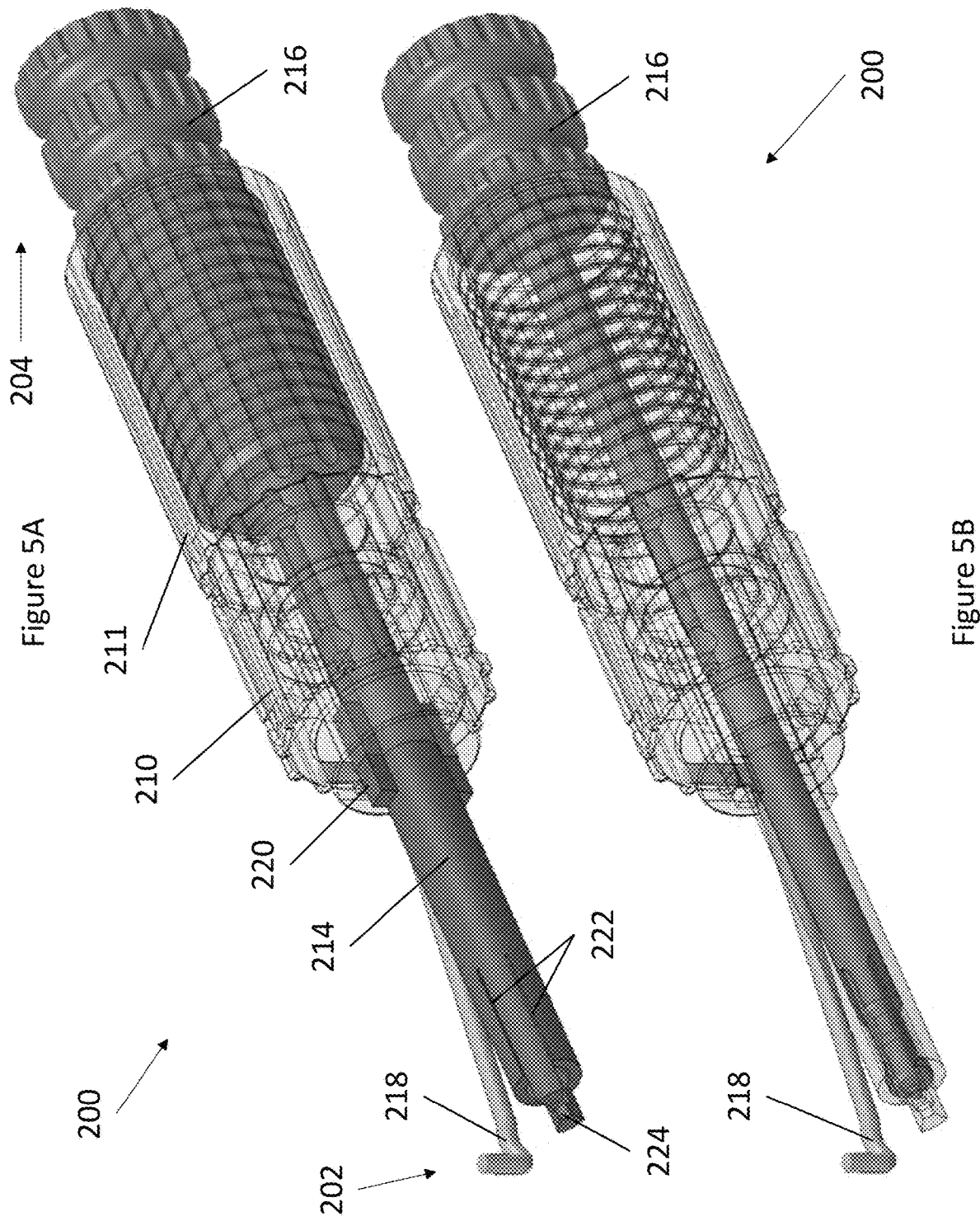
FIG. 5A through FIG. 5C depict partially wireframe views of an exemplary insertion tool to show the internal components.
Figure 5C:
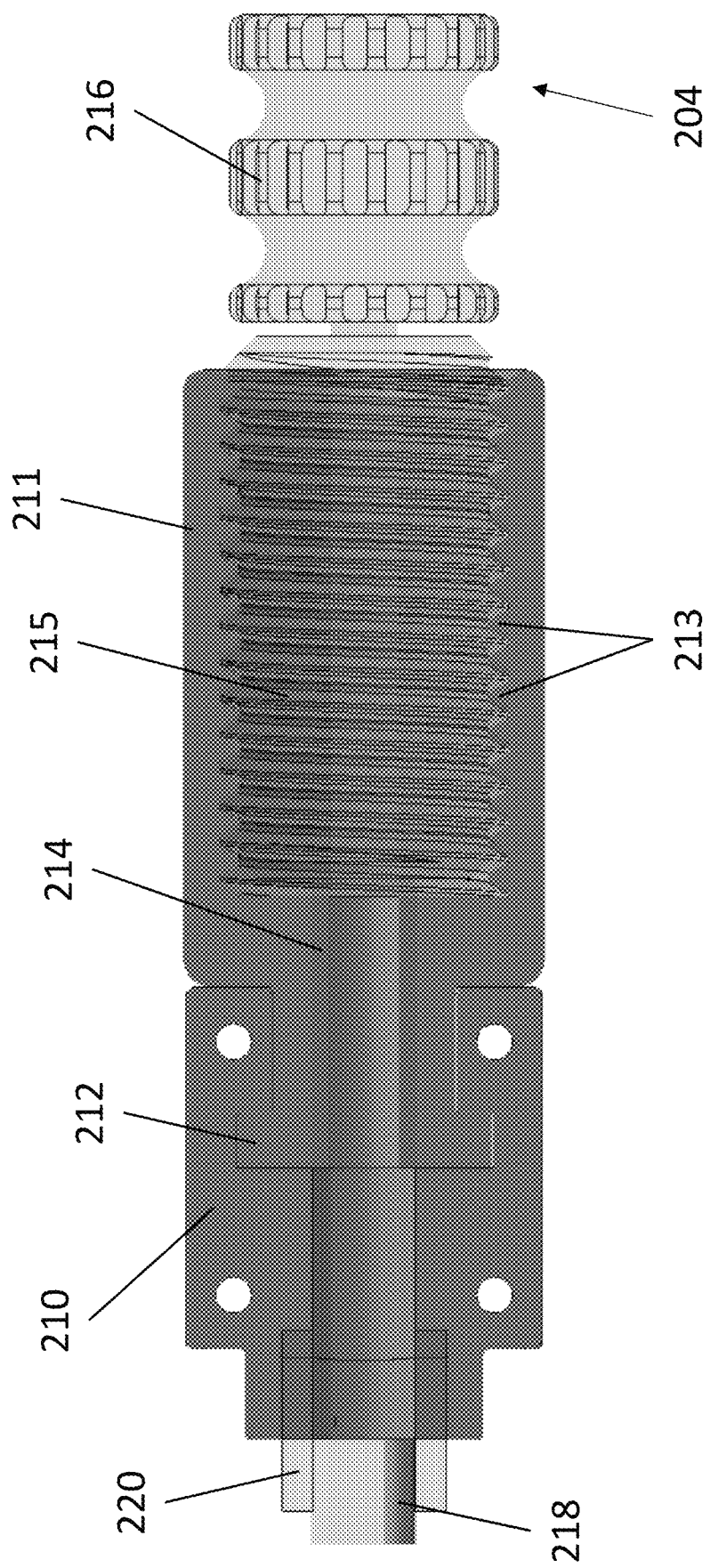

Referring now to FIG. 4, an exemplary insertion tool 200 is depicted. Insertion tool 200 comprises an anterior end 202, a posterior end 204, a nonrotating grip 210, a rotating grip 211, a clamp 214, a locking bit driver 216, and an anchor rod 218. The interior of insertion tool 200 is shown in greater detail in FIG. 5A through FIG. 5C.

Nonrotating grip 210 and rotating grip 211 are connected by a flange 212 around which rotating grip 211 twists freely. Rotating grip 211 has a hollow interior comprising thread 213 and a lumen connected to a lumen of nonrotating grip 210. Clamp 214 is positioned within the continuous lumen of nonrotating grip 210 and rotating grip 211. Clamp 214 comprises an elongate tubular shape having a lumen running throughout, and is tipped by hooks 224 at anterior end 202 and a threaded section 215 at posterior end 204. Threaded section 215 is mated with the thread 213 of the hollow interior of rotating grip 211, such that twisting rotating grip 211 twists threads 213 to advance clamp 214 in an anterior or a posterior direction. Clamp 214 can further include tabs 220 that fit within nonrotating grip 210 to prevent clamp 214 from rotating within insertion tool 200.

Locking bit driver 216 is positioned within the lumen of clamp 214 and is freely twistable and slidable within clamp 214. Locking bit driver 216 comprises an elongate rod shape and is tipped by a driver 226 at anterior end 202 (FIG. 6A, FIG. 6B). At posterior end 204, locking bit driver 216 can include any suitable grip or handle.

Referring now to FIG. 6A and FIG. 6B, the construction of the anterior end 202 of insertion tool 200 is depicted. Anchor rod 218 is a stiff member extending from nonrotating grip 210 in an anterior direction adjacent to clamp 214 and locking bit driver 216. Anchor od 218 is loosely connected to nonrotating grip 210 such that anchor rod 218 may freely pivot about on a horizontal plane. In certain embodiments, anchor rod 218 is restricted from deviating from the horizontal plane. Anchor rod 218 comprises an upturned anterior end connectable to an expandable device, as described elsewhere herein.

Slits 222 are cut into the anterior end of clamp 214 to form bendable portions that extend past the anterior end of clamp 214 and terminate in hooks 224. In FIG. 6B, a partially wireframe view of clamp 214 depicts ridges 230 positioned on the inner surface of the bendable portions. FIG. 6B also depicts the anterior end of locking bit driver 216, wherein an indent is positioned adjacent to head 228 of locking bit driver 216 to accommodate ridges 230. In this arrangement, sliding locking bit driver 216 in a posterior direction within clamp 214 brings head 228 into contact with ridges 230. Further posterior advancement wedges head 228 beneath ridges 230, causing the bendable portions of clamp 214 and hooks 224 to bend away from head 228.

Figure 7A:
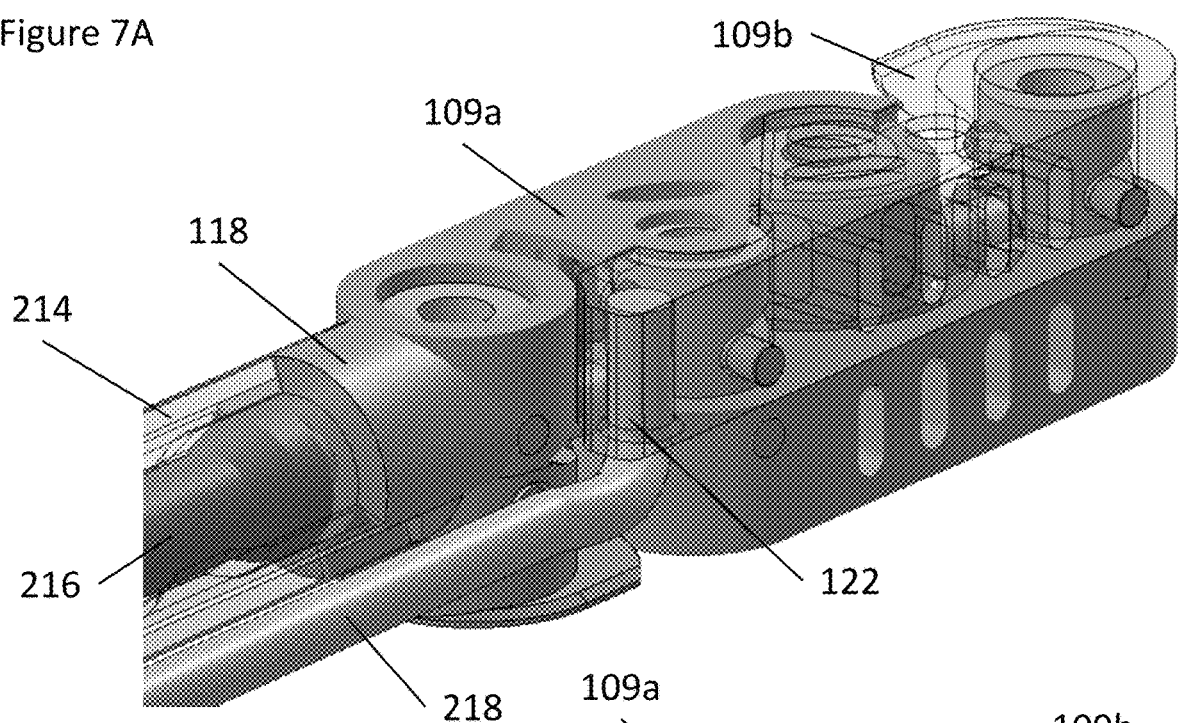
FIG. 7A and FIG. 7B depict an exemplary insertion tool secured to a closed expandable device (FIG. 7A) and actuated to open and lock the expandable device (FIG. 7B).
Figure 7B:
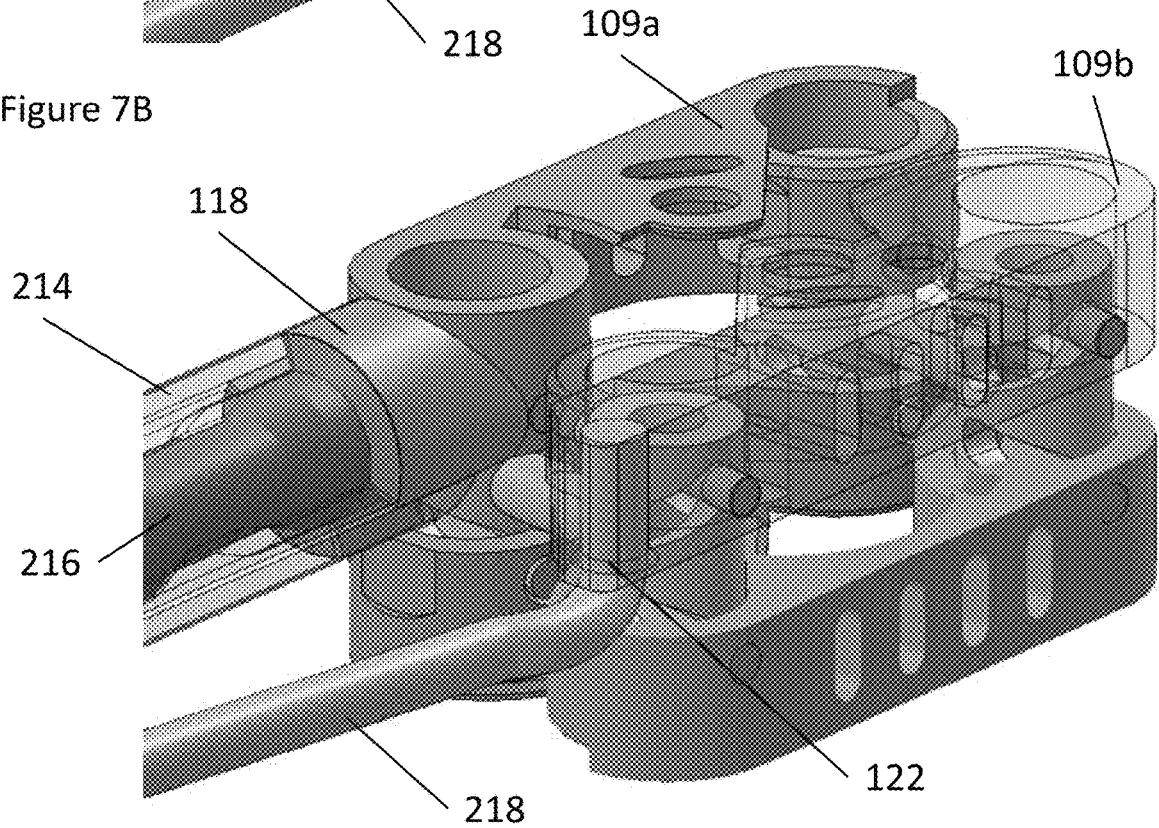

Referring now to FIG. 7A and FIG. 7B, insertion tool 200 is depicted engaged to and opening expandable device 100. In FIG. 7A, clamp 216 and anchor rod 218 of insertion tool 200 are engaged to arm 109a and arm 109b, respectively. Hooks 224 of clamp 216 are inserted into attachment feature 119 of arm 109a, and the upturned anterior end of anchor rod 218 is inserted into socket 122 of arm 109b. To open expandable device 100, rotating grip 211 is twisted while nonrotating grip 210 is held fast, such that clamp 216 is advanced in an anterior direction within rotating grip 211. The anterior advancement of clamp 216 pushes arm 109a in an anterior direction, while anterior movement of arm 109b is prevented due to the rigid anchor rod 218 holding arm 109b in place. The relocation of arm 109a relative to arm 109b leads to a synchronized series of movements where pins 114 in arm 109a moving through pin guides 126 rotates the associated bolts 112 as well as the opposing bolts 112 connected by connecting rods 124, positioning all pins 114 in their open positions 130 shown in FIG. 7B. Expandable device 100 can be closed by twisting rotating grip 211 in an opposite direction, which advances clamp 216 and arm 109a in a posterior direction and causes the aforementioned movements to perform in reverse.

Expandable device 100 can be locked into any position between its open configuration and its closed configuration by sliding locking bit driver 216 into its anterior-most position to seat driver 226 into locking bit 120. Locking bit driver 216 can be twisted to drive locking bit 120 into the adjacent bolt 112, locking its rotation as well as the movement of every other interconnected piece. Locking bit driver 216 can then be slid into its posterior-most position, whereby head 228 of locking bit driver 216 pushes ridges 230 apart to disengage hooks 224 from attachment feature 119, freeing insertion tool 200 from expandable device 100.

Second Expandable Device

Figure 8A:
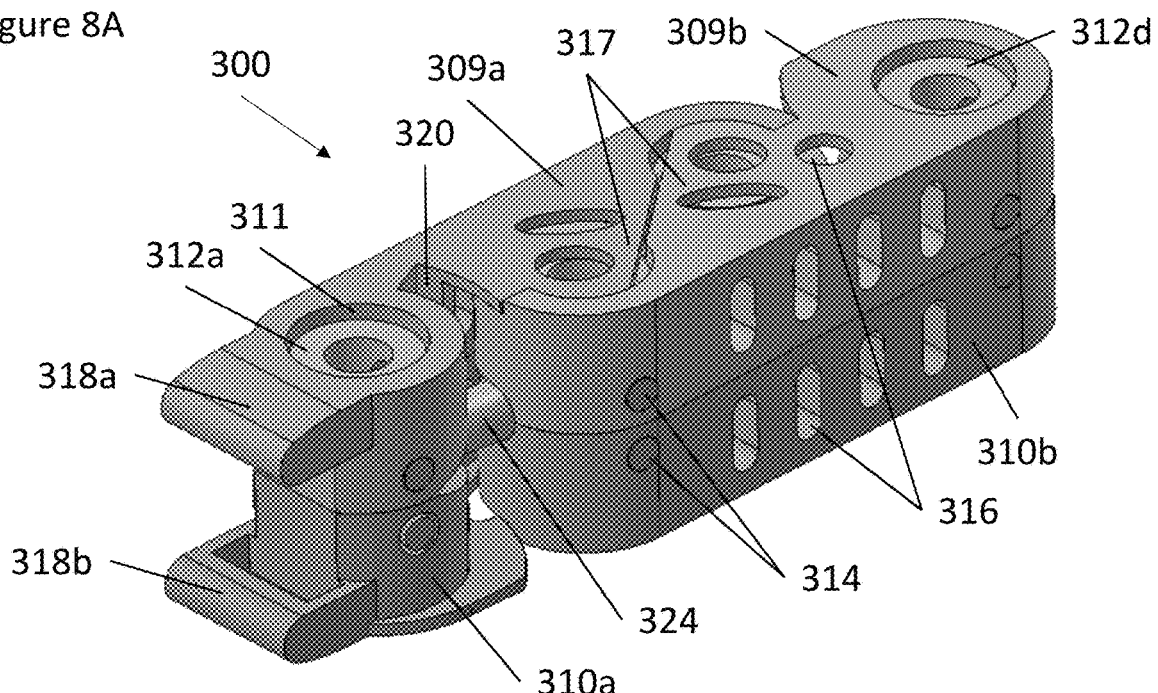
FIG. 8A and FIG. 8B depict perspective views of an exemplary expandable device in a closed configuration (FIG. 8A) and in an open configuration (FIG. 8B).
Figure 8B:
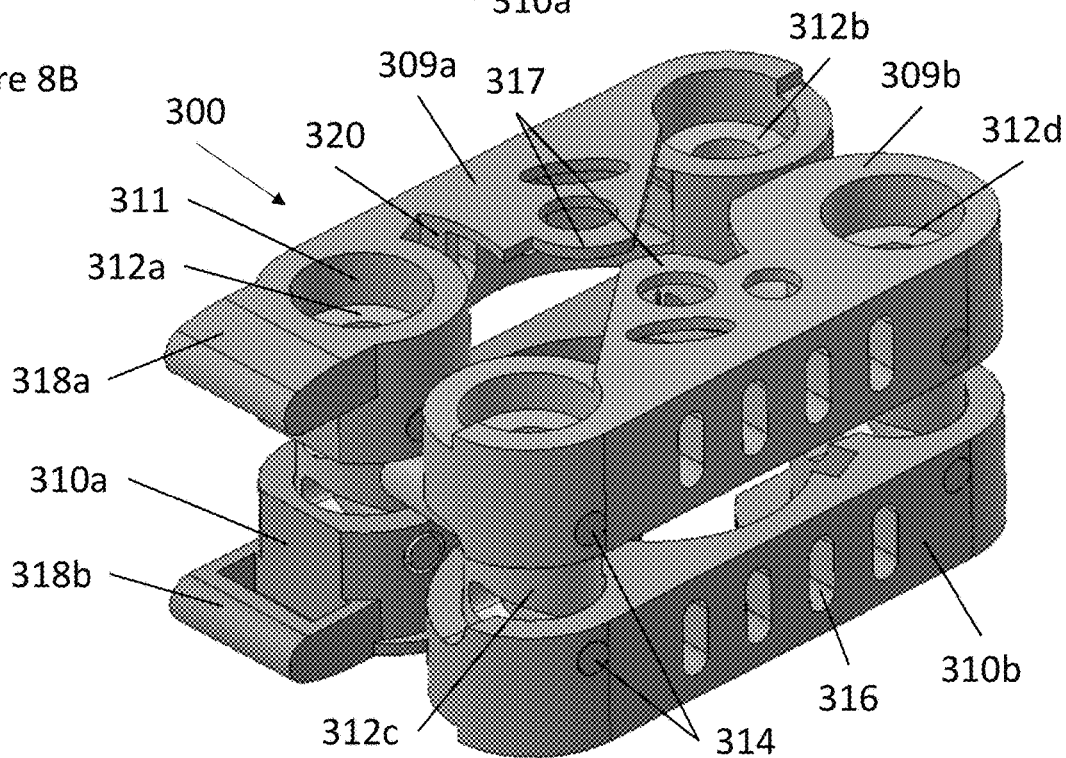

Referring now to FIG. 8A and FIG. 8B, an exemplary expandable device 300 is depicted. Expandable device 300 comprises four arms (superior first arm 309a, superior second arm 309b, inferior first arm 310a, and inferior second arm 310b) and four movable bolts 312 (referred to herein as posterior first bolt 312a, anterior second bolt 312b, posterior third bolt 312c, and anterior fourth bolt 312d). Each arm comprises two slots 311 sized to fit a movable bolt 312. Each bolt 312 is secured within a slot 311 by a pin 314 fixed to each arm, and bolts 312a-312d are secured in pairs by a connecting rod 324 (312a connected to 312c, 312b connected to 312d), visible in FIG. 9A and FIG. 9B.

Arms 309a, 309b, 310a, 310b, bolts 312a-312d, and pins 314 are preferably constructed from a rigid material, such as a metal or a hard polymer. In various embodiments, the rigid material is a biocompatible material. In certain embodiments, arms 310 can comprise a surface that is textured or at least partially covered with barbs or spikes to improve the attachment of expandable device 300 within a space.

In various embodiments, each arm can comprise a plurality of cavities 316. Cavities 316 may be placed throughout each arm 310 without compromising the rigidity of expandable device 300. Cavities 316 can be filled with any component that is synergistic with the function of expandable device 300. For example, in some embodiments, cavities 316 can be packed with a biological material to promote the ingrowth of tissue, such as bone. In some embodiments, cavities 316 can be packed with a therapeutic to treat surrounding tissue. In some embodiments, one or more sensors can be inserted into cavities 316 to monitor the device and its environs, such as a temperature sensor, pressure sensor, corrosion sensor, and the like. In some embodiments, cavities 316 can be used to secure expandable device 300 within a space, by accepting screws or cement. Cavities 316 can also be used to view and monitor the progress of bone growth into the interior of expandable device 300.

In various embodiments, each arm can comprise one or more fins 317 to increase the surface area of the top and bottom of expandable device 300. Fins 317 can be sized to interlock when expandable device 300 is closed to decrease the footprint of expandable device 300.

In some embodiments, an arm may further comprise features for engaging an insertion tool, described elsewhere herein. For example, arm 309a and arm 310a can comprise a connector 318a and a connector 318b, respectively, to engage the pry bars of an insertion tool, described elsewhere herein. In certain embodiments, arm 309a can further comprises gap 320 to facilitate the engagement of a chain-arm hook of an insertion tool, described elsewhere herein.

In FIG. 9A and FIG. 9B, expandable device 300 has been depicted without arms 309b and 310b to illustrate the arrangement of bolts 312a-312d and the mechanism by which bolts 312a-312d, pins 314, and the arms open and close in a synchronized manner. The structure of bolts 312 are similar to what is described for bolts 112 above and in FIG. 2A. In this embodiment, each arm 309a, 309b, 310a, and 310b is aligned in parallel or substantially in parallel with each other (visualized by arm axes 334 running through the lengths of each arm), and each arm comprises a fixed pin 314 passing through an opposing pair of pin guides 326 to secure a bolt 312 into each of its two slots 311. Pins 314 are fixed relative to each of the arms, such that each pin 314 is arranged in parallel or substantially in parallel to each other (visualized by pin axes 332 running through the lengths of each pin 314). Rotating bolt 312 slides pin 314 within pin guide 326 between a closed position 328 and an open position 330. The height difference between closed position 328 and open position 330 thereby increases the distance between pins 314, which also separates the superior arms 309a and 309b from the inferior arms 310a and 310b. Similar to expandable device 100 depicted in FIG. 3A and FIG. 3B, shifting expandable device 300 between a closed configuration and an open configuration maintains the parallel alignment between arm 309a (and arm 310a underneath) on one side and arm 309b (and arm 310b underneath) on the opposite side as well as between pins 314. Shifting expandable device 300 between a closed configuration and an open configuration also induces a separation in distance between arms 309a and 310a on one side and arms 309b and 310b on the opposite side due to the length of the connecting rods 324.

The exemplary expandable device 300 is depicted as having a polyhedron-like shape with four rectangular sides and a parallelogram-like top and bottom when closed (FIG. 8A), and a polyhedron-like shape with four rectangular sides and a rectangular top and bottom when open (FIG. 8B). However, it should be understood that expandable device 300 is not limited to the depicted shapes, and can have any suitable shape. For example, each of the arms can comprise a semicircular shape to give expandable device 300 an overall cylindrical shape having curved sides and a circular or oval top and bottom.

In some embodiments, one or more of the connecting rods 324 can have a different length (not pictured). For example, bolt 312a and bolt 312c can be joined by a connecting rod 324 having a first length, and bolt 312c and bolt 312d can be joined by a connecting rod 324 having a second length, such that arms 309a and 310a are separated from the opposing arms 309b and 310b by the first length at one end and by a second length at an opposing end. In this manner, expandable device 300 can thereby maintain a substantially rectangular top and bottom when closed, and has a substantially trapezoidal top and bottom when open.

In some embodiments, one or more of the bolts 312 can have pin guides 326 with different open positions 330 (not pictured). For example, bolt 312a and bolt 312c can each have pin guides 326 with an open position 330 at a first height, and bolt 312b and bolt 312d can each have pin guides 326 with an open position 330 at a second height, such that superior arms 309a and 309b are separated from inferior arms 310a and 310b by a first height at one end and by a second height at an opposing end. In this manner, expandable device 300 can thereby maintain substantially rectangular sides when closed, and has a lordotic angle with a substantially trapezoidal left and right side when open.

Expandable device 300 can have any suitable dimensions between its closed and open configurations. For example, in certain embodiments, expandable device 300 can have a closed length of between 30 mm to 30 cm, a closed width of between 7 mm to 7 cm, and a closed height of between 8 mm and 8 cm. In certain embodiments, expandable device 300 can have an open length of between 20 mm to 20 cm, an open width of between 10 mm to 10 cm, and an open height of between 10 mm and 10 cm. The surface area and footprint of expandable device 300 will depend on the length, width, and height, and will change accordingly between open and closed configurations. The surface area of expandable device 300 will further depend on modifications to expandable device 300, such as the number of cavities 316 and the size and overlapping of fins 317. In one embodiment, an exemplary expandable device 300 has a closed length, width, and height of 31.33 mm, 7.55 mm, and 8 mm; an open length, width and height of 25.03 mm, 13.83 mm, and 10.62 mm; a closed footprint and footprint surface area of 195.52 mm$^2$ and 141.15 mm$^2$; and an open footprint and footprint surface area of 299.07 mm$^2$ and 158.53 mm$^2$.

Second Insertion Tool for the Second Expandable Device

Figure 10:
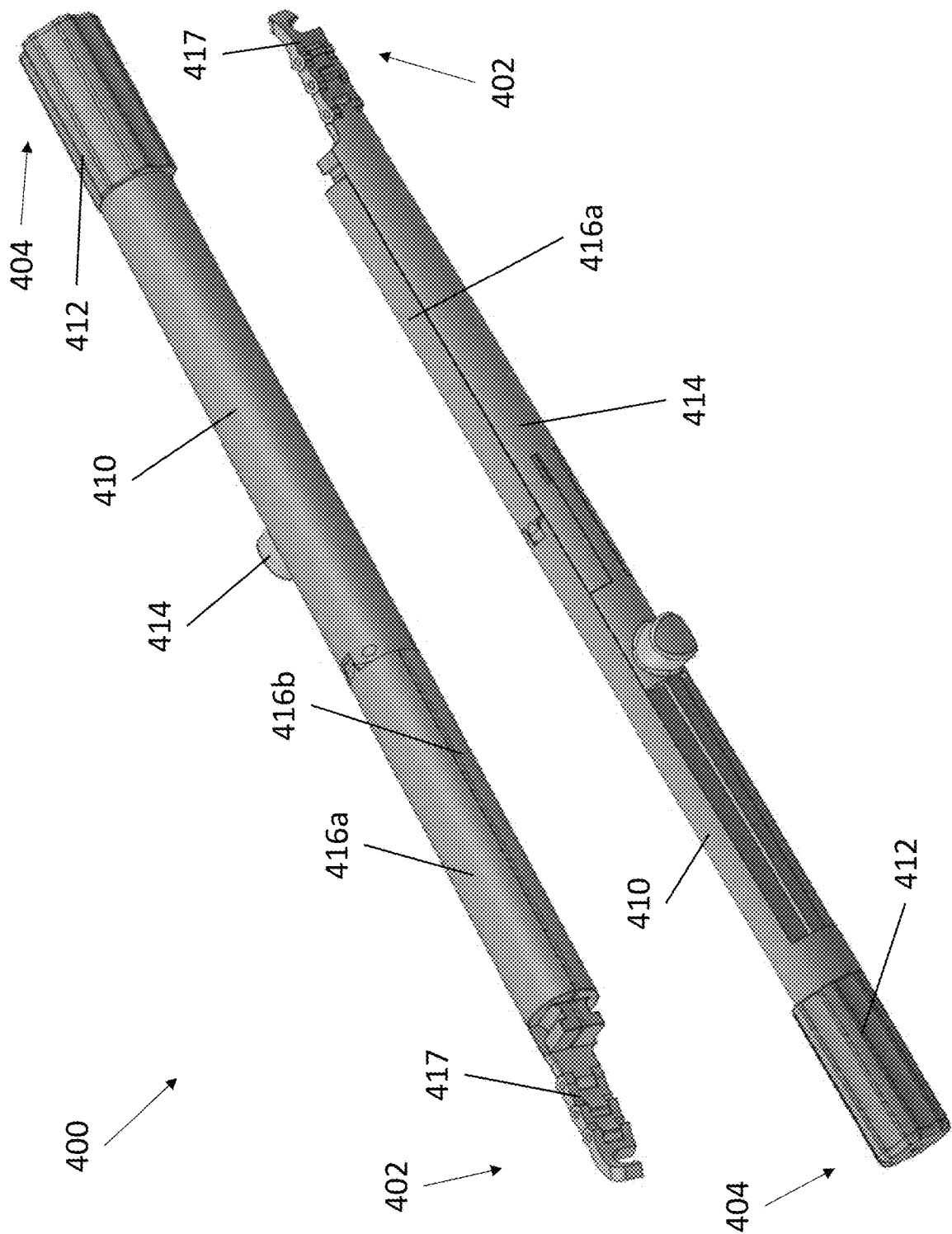
FIG. 10 depicts perspective views of an exemplary insertion tool for deploying an expandable device of the present invention.
Figure 11:
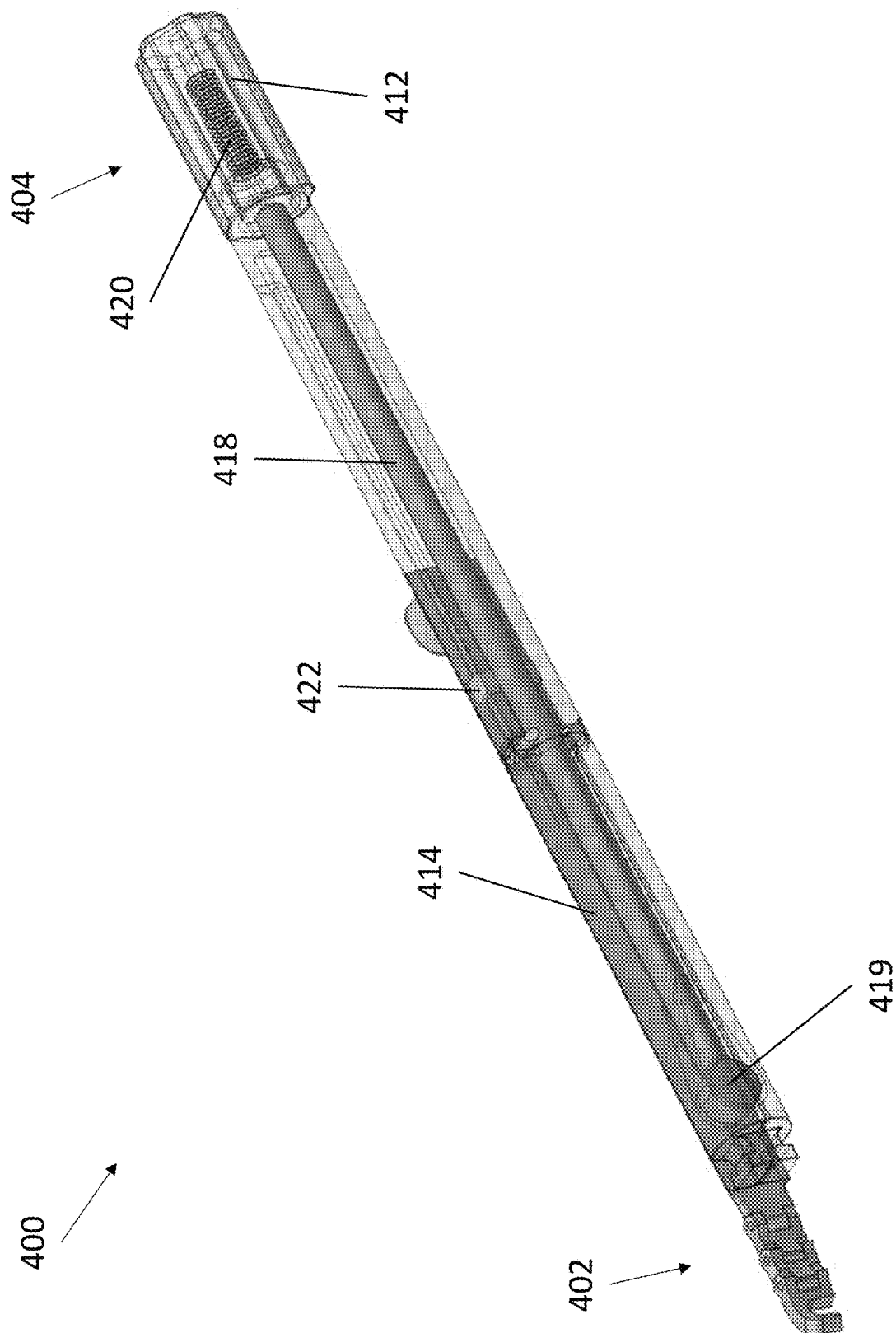
FIG. 11 depicts a partially wireframe view of an exemplary insertion tool to show the internal components.

Referring now to FIG. 10, an exemplary insertion tool 400 is depicted. Insertion tool 400 comprises an anterior end 402, a posterior end 404, a housing 410, a rotating grip 412, a slider 414, pry bars 416a and 416b, and chain-arm hook 417. The interior of insertion tool 400 is shown in greater detail in FIG. 11.

Figure 12A:
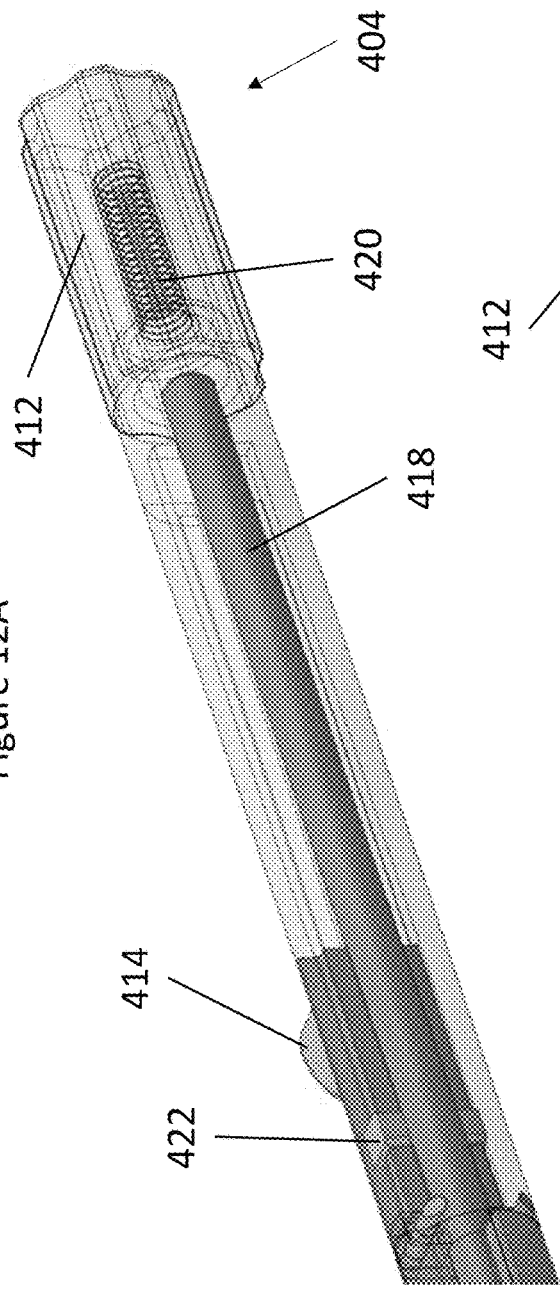
FIG. 12A and FIG. 12B depict magnified partially wireframe views of the posterior of an exemplary insertion tool.
Figure 12B:
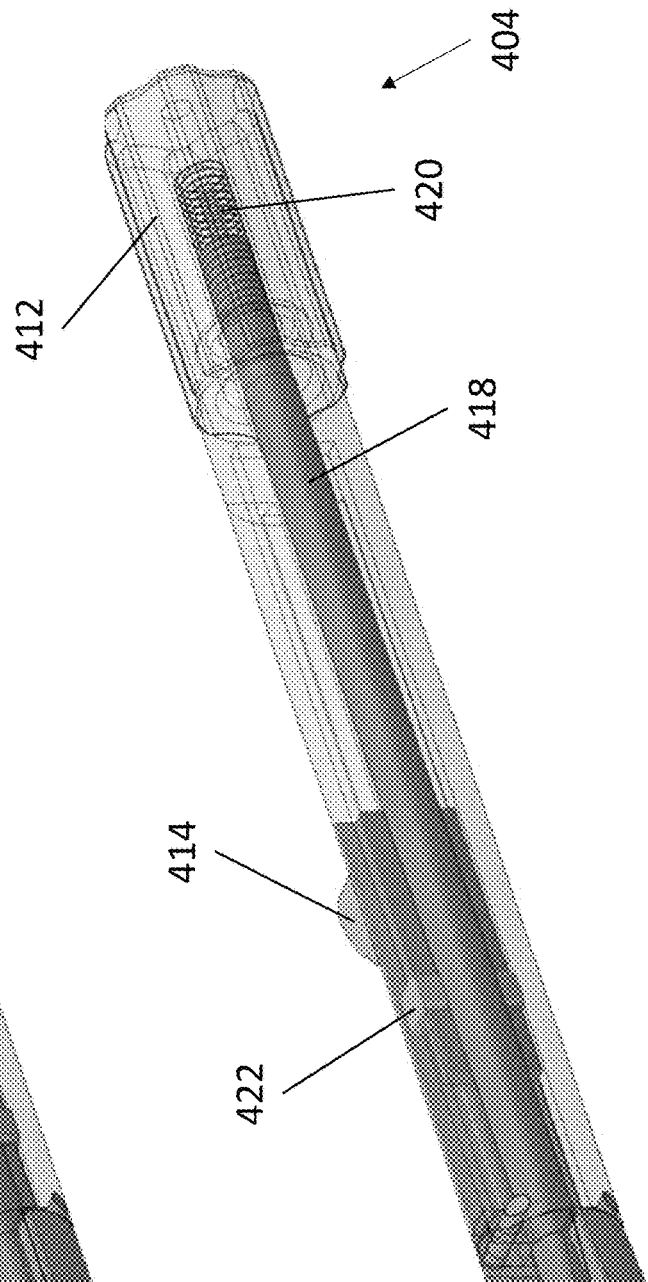

Housing 410 comprises a tubular shape having a lumen running throughout. Rotating grip 412 is connected to the posterior end of housing 410 and comprises a threaded lumen 420 connected to the lumen of housing 410. Pry bar 416a and pry bar 416b are each connected to the anterior end of housing 410 by a hinge. In some embodiments, insertion tool 400 comprises a means of maintaining an attraction between pry bar 416a and pry bar 416b, such as a magnet, a spring, or an elastic band. Slider 414 slides along the side of housing 410 and comprises chain-arm hook 417 positioned at its anterior end. Wedge rod 418 is positioned within the lumen of housing 410. Wedge rod 418 comprises a threaded region at its posterior end (not rendered) and terminates in wedge 419 at its anterior end. FIG. 12A and FIG. 12B depict the actuation of wedge rod 418 by rotating grip 412, wherein twisting rotating grip 412 mates threaded lumen 420 with the posterior threaded region of wedge rod 418 to advance wedge rod 418 in an anterior or posterior direction. In some embodiments, wedge rod 418 and slider 414 are attached by coupling 422, such that the movement of slider 414 is coupled with the movement of wedge rod 418.

Referring now to FIG. 13A and FIG. 13B, the function of wedge rod 418 is depicted. Pry bar 416a has been rendered in wireframe to reveal sloped indent 426, which is also present in pry bar 416b. Combining the two sloped indents 426 provides a space capable of accommodating wedge 419 when in an anterior-most position. As described above, wedge rod 418 can be advanced in an anterior or posterior direction using rotating grip 412. In FIG. 13B, the posterior advancement of wedge rod 418 slides wedge 419 against the sloped indents 426 to steadily spread pry bar 416a and pry bar 416b away from each other.

Figure 14:
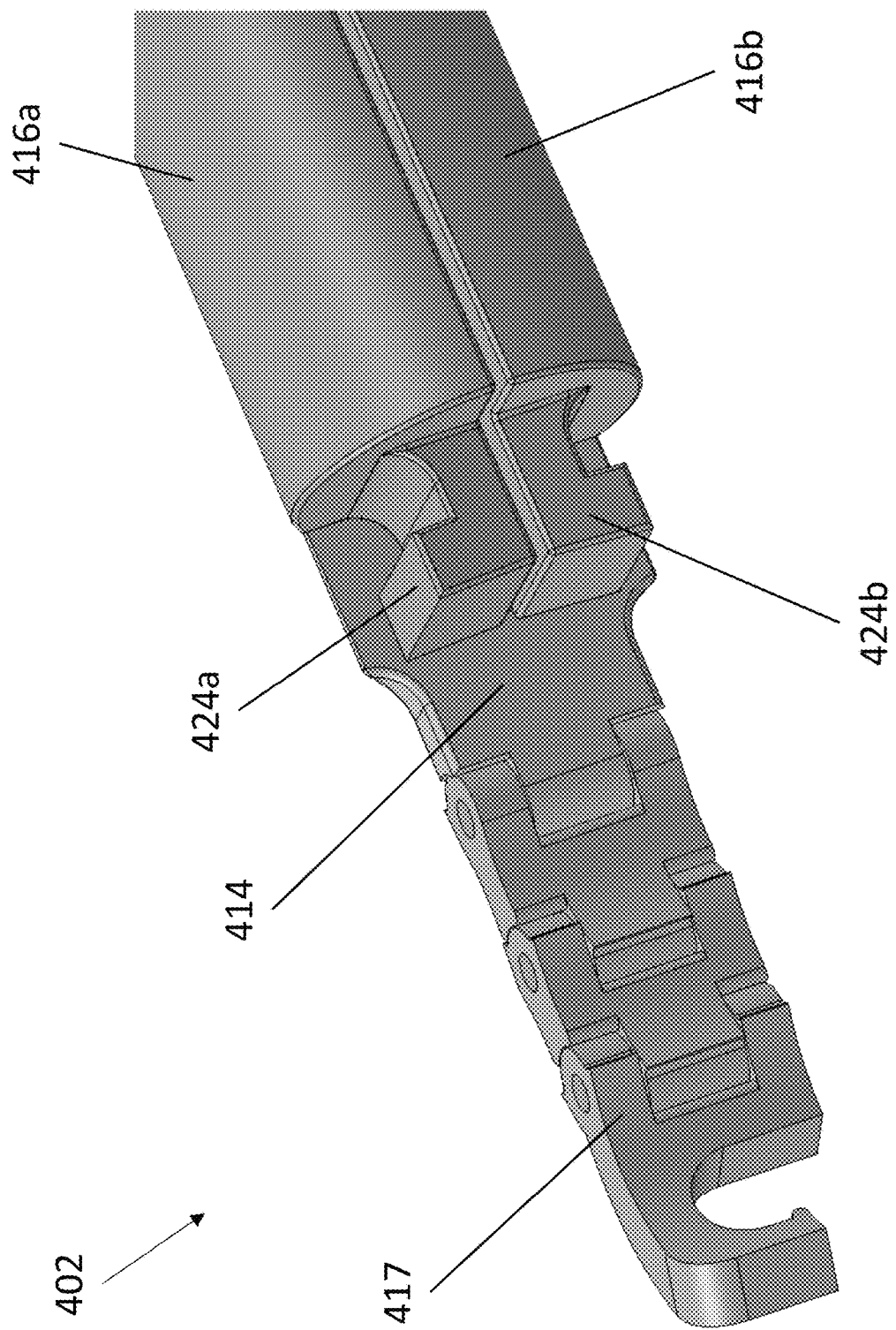
FIG. 14 depicts a perspective view of the anterior end of an exemplary insertion tool.
Figure 15:
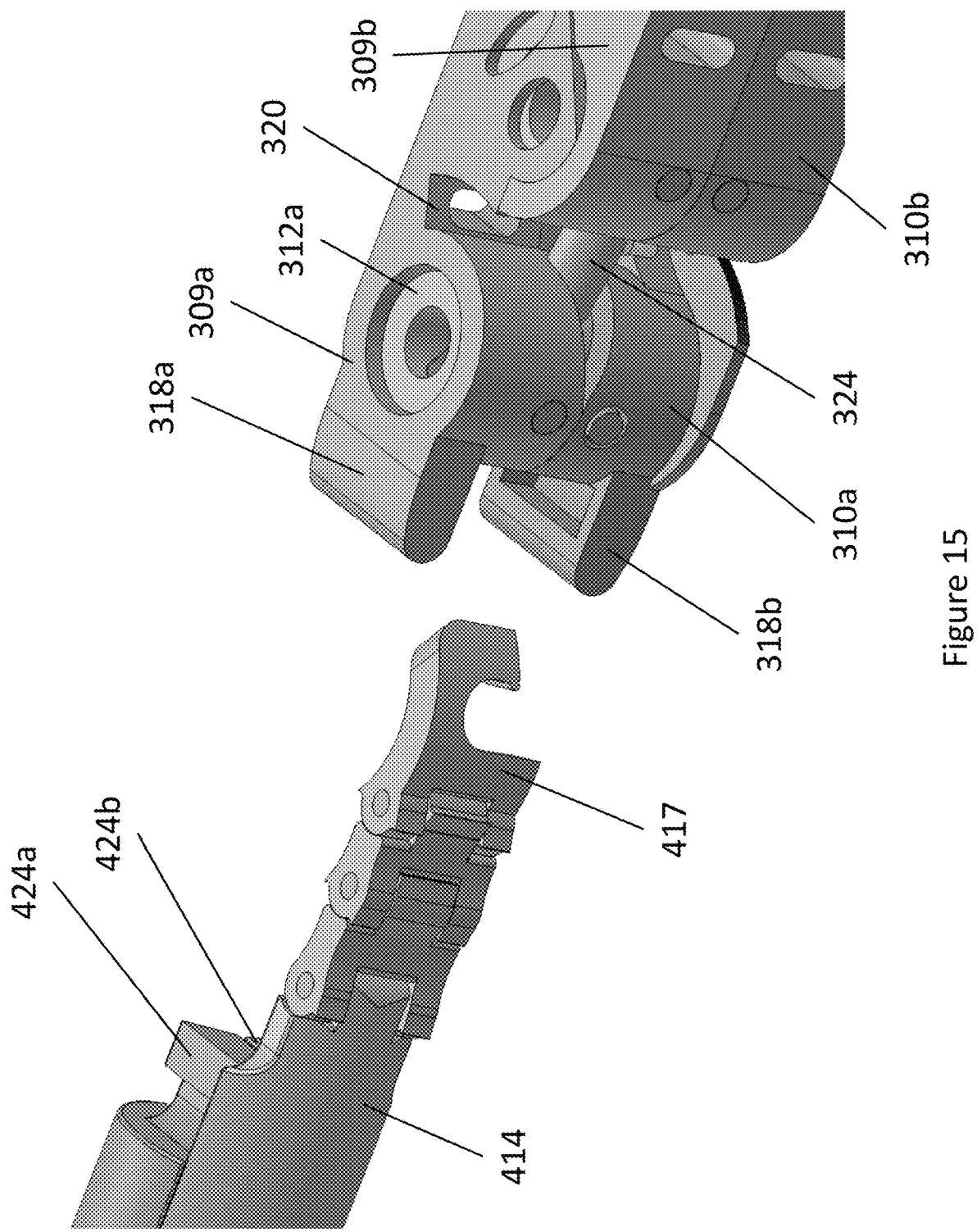
FIG. 15 depicts the anterior end of an exemplary insertion tool juxtaposed next to an exemplary expandable device.

Referring now to FIG. 14, the anterior end of insertion tool 400 is depicted in detail. The anterior end of pry bar 416a and pry bar 416b terminates in tab 424a and tab 424b, respectively. Chain-arm hook 417 is constructed from a series of armed chains extending from the anterior end of slider 414 and ends with a hook sized to loop around a connecting rod 324 of expandable device 300. FIG. 15 juxtaposes the anterior end of insertion tool 400 with expandable device 300 to illustrate the points of engagement. As described elsewhere herein, tab 424a and tab 424b fit within connector 318a and connector 318b to engage pry bar 424a to arm 309a and to engage pry bar 424b to arm 310a. Chain-arm hook 417 loops around connecting rod 324, with gap 320 provided on arm 309a to facilitate access to connecting rod 324.

Referring now to FIG. 16A and FIG. 16B, insertion tool 400 is depicted engaged to and opening expandable device 300. In FIG. 16A, pry bar 416a and pry bar 416b of insertion tool 400 are engaged to arm 309a and arm 310a, respectively, and chain-arm hook 417 is looped around connecting rod 324 (not visible). To open expandable device 300, rotating grip 412 is twisted while housing 410 is held fast, such that wedge rod 418 is advanced in a posterior direction within housing 410. The posterior advancement of wedge rod 418 pulls wedge 419 in a posterior direction, spreading pry bar 416a and pry bar 416b apart to push arm 309a and arm 310a away from each other. Slider 414 is also advanced in a posterior direction, either by direction pulling on slider 414 or by virtue of a coupling 422 coupling the movement of slider 414 with wedge 419. The posterior advancement of slider 414 pulls chain-arm hook 417 in a posterior direction, which pulls on connecting rod 324 to encourage the rotation of bolt 312a. The coordinated action of pushing apart arm 309a and arm 310b and pulling on connecting rod 324 leads to a synchronized series of movements where pins 314 are guided through pin guides 326, positioning all pins 314 in their open positions 330 shown in FIG. 7B. Insertion tool 400 can be removed by twisting rotating grip 412 in an opposite direction to advance wedge rod 418 in an anterior direction and to clear wedge 419 from the sloped indents 426, thereby enabling pry bar 416a and pry bar 416b to close together and disengage tab 424a and tab 424b from connector 318a and connector 318b. Chain-arm hook 417 can be unlooped from connecting rod 324, freeing insertion tool 400 from expandable device 300.

Third Expandable Device

Referring now to FIG. 17A through FIG. 17D, an exemplary expandable device 500 is depicted. Expandable device 500 comprises four arms (superior first arm 502a, superior second arm 502b, inferior third arm 504a, and inferior fourth arm 504b) and four movable bolts 508 (referred to herein as posterior first bolt 508a, anterior second bolt 508b, posterior third bolt 508c, and anterior fourth bolt 508d). Each arm comprises two slots 506 sized to fit a movable bolt 508. Each bolt 508 is secured within a slot 506 by a pin 512 fixed to each arm. Bolt 508a is secured to bolt 508c by crossbar 510a, and bolt 508b is secured to bolt 508d by crossbar 510b, described elsewhere herein.

Arms 502a, 502b, 504a, 504b, bolts 508a-508d, and pins 512 are preferably constructed from a rigid material, such as a metal or a hard polymer. In various embodiments, the rigid material is a biocompatible material. In certain embodiments, each arm can comprise a surface that is textured or at least partially covered with barbs or spikes to improve the attachment of expandable device 500 within a space, such as barbs 516. In certain embodiments, each arm can terminate in a taper 505 at an anterior end, wherein taper 505 facilitates entry of expandable device 500 into a space.

In various embodiments, each arm can comprise a plurality of windows 514. Windows 514 may be placed throughout each arm without compromising the rigidity of expandable device 500. Windows 514 can be filled with any component that is synergistic with the function of expandable device 500. For example, in some embodiments, windows 514 can be packed with a biological material to promote the ingrowth of tissue, such as bone. In some embodiments windows 514 can be packed with a therapeutic to treat surrounding tissue. In some embodiments, one or more sensors can be inserted into windows 514 to monitor the device and its environs, such as a temperature sensor, pressure sensor, corrosion sensor, and the like. In some embodiments, windows 514 can be used to secure expandable device 500 within a space, by accepting screws or cement. Windows 514 can also be used to view and monitor the progress of bone growth into the interior of expandable device 500.

Figure 17A:
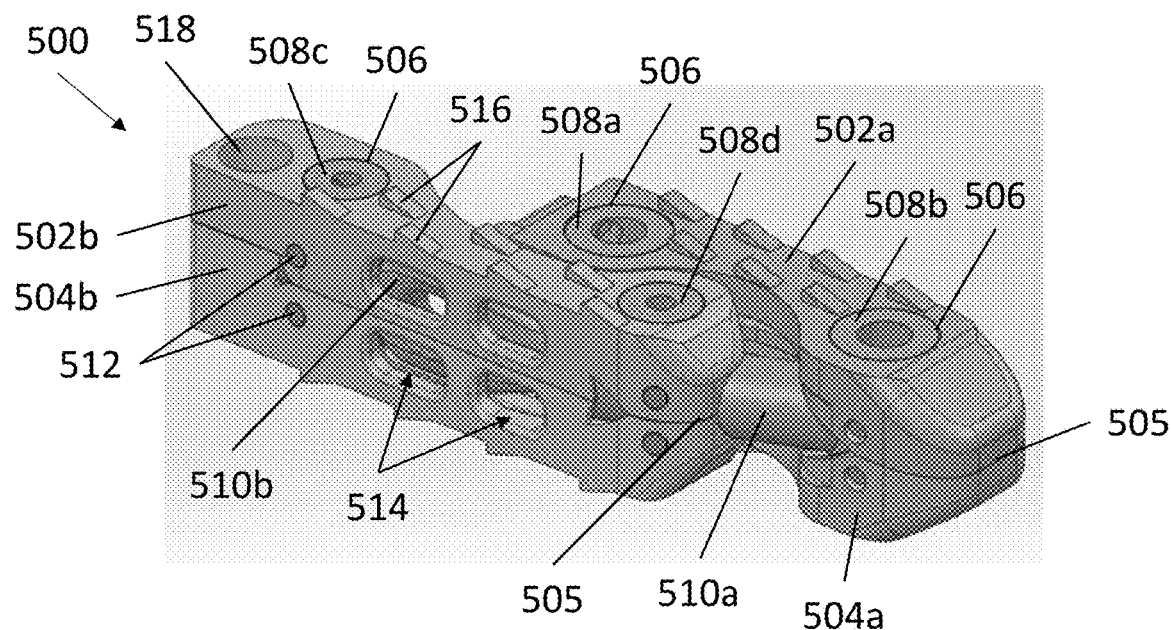
FIG. 17A through FIG. 17D depict perspective views of an exemplary expandable device in a closed configuration.
Figure 17B:
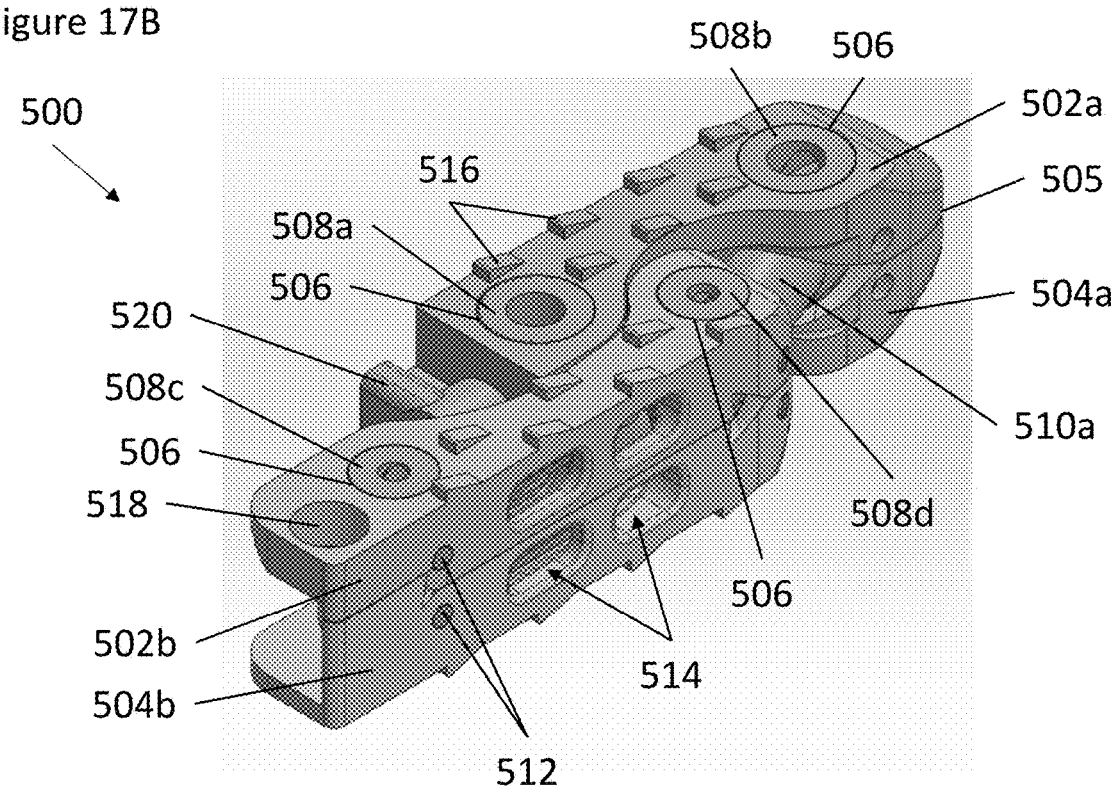
Figure 17C:
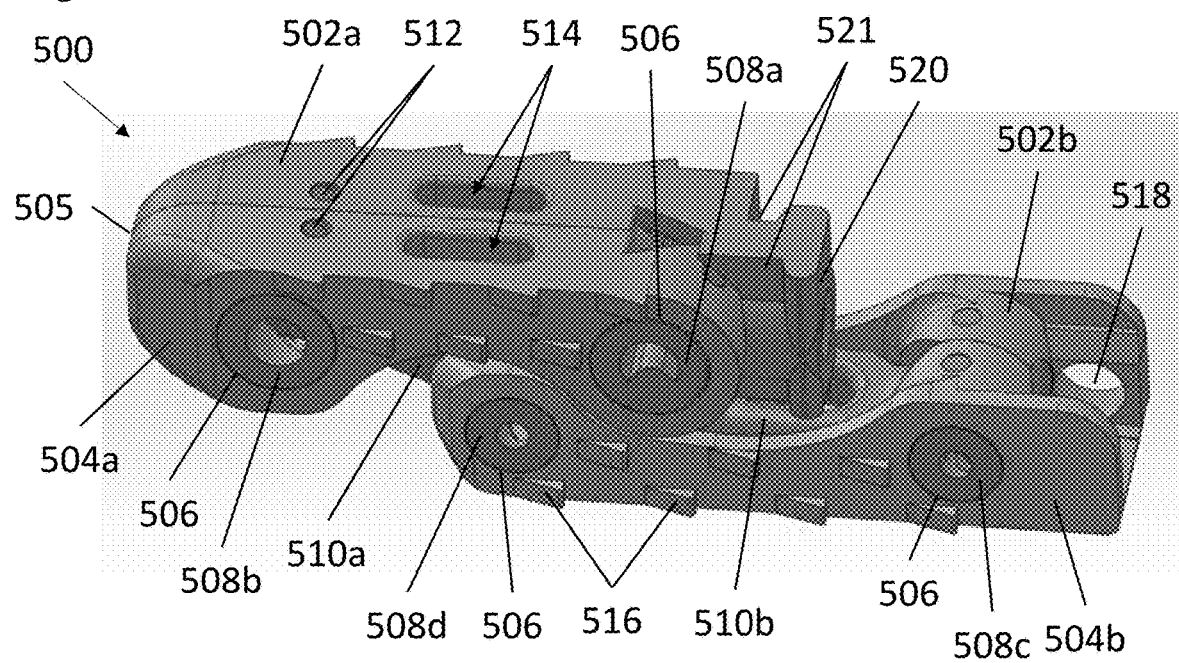
Figure 17D:
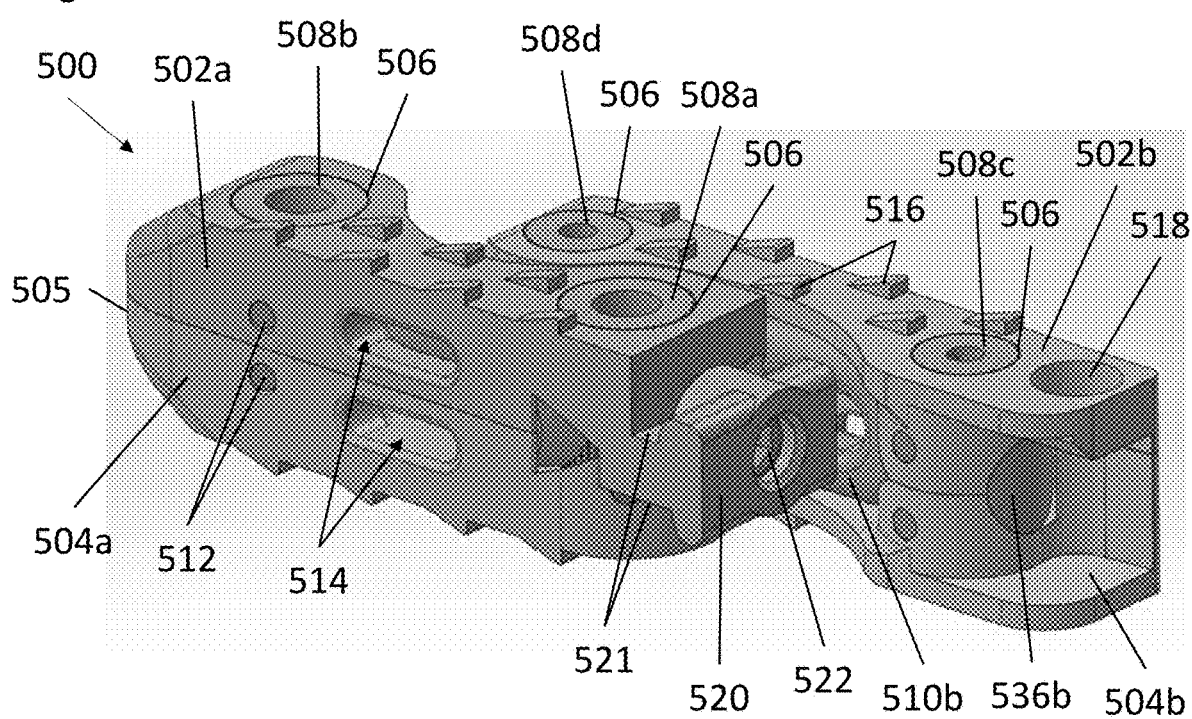
Figure 18A:
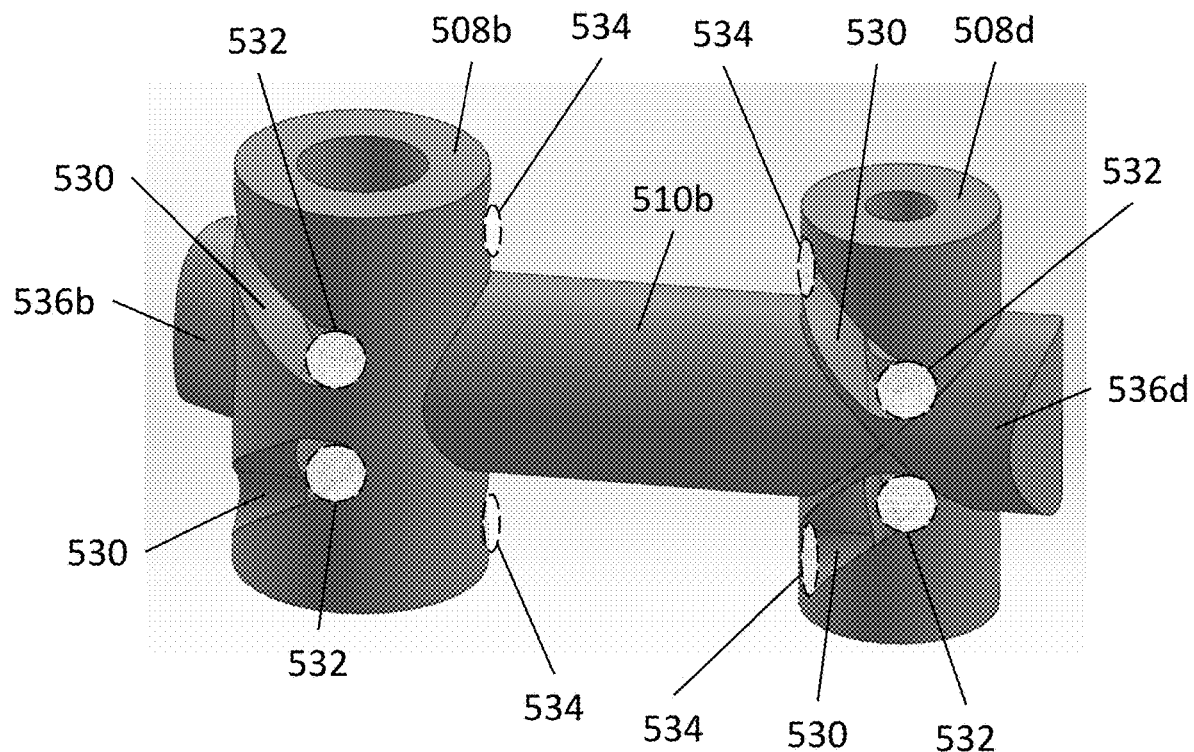
FIG. 18A and FIG. 18B depict a perspective view and a top view, respectively, of a first connecting rod connecting two bolts of an exemplary expandable device.
Figure 18B:
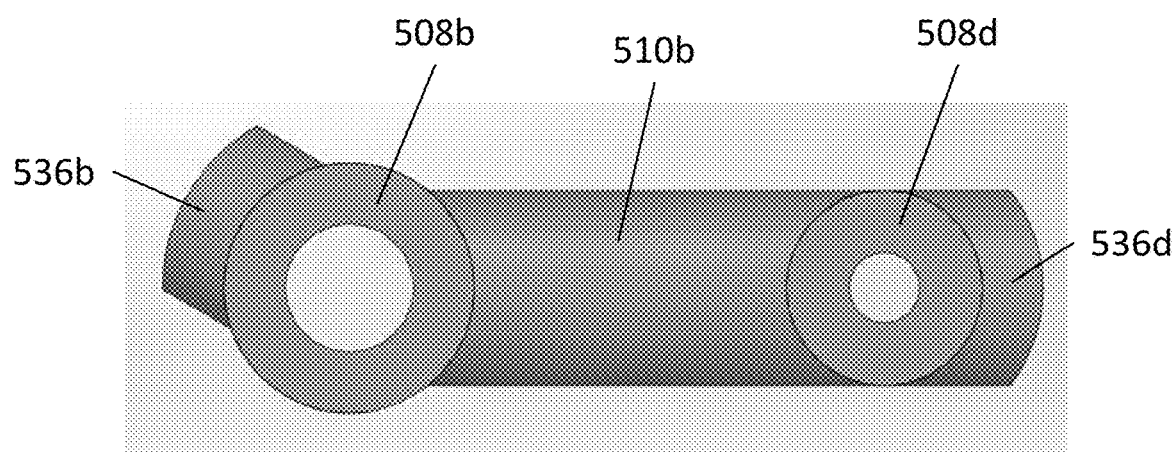
Figure 18C:
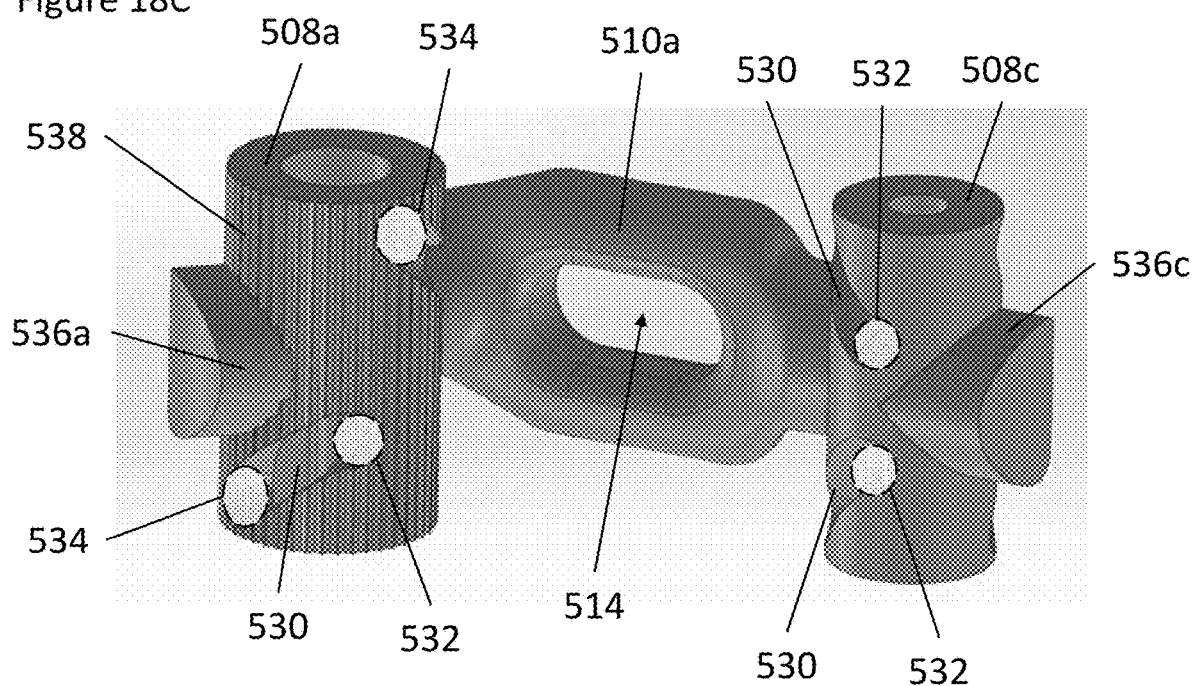
FIG. 18C and FIG. 18D depict a perspective view and a top view, respectively, of a second connecting rod connecting two bolts of an exemplary expandable device.
Figure 18D:
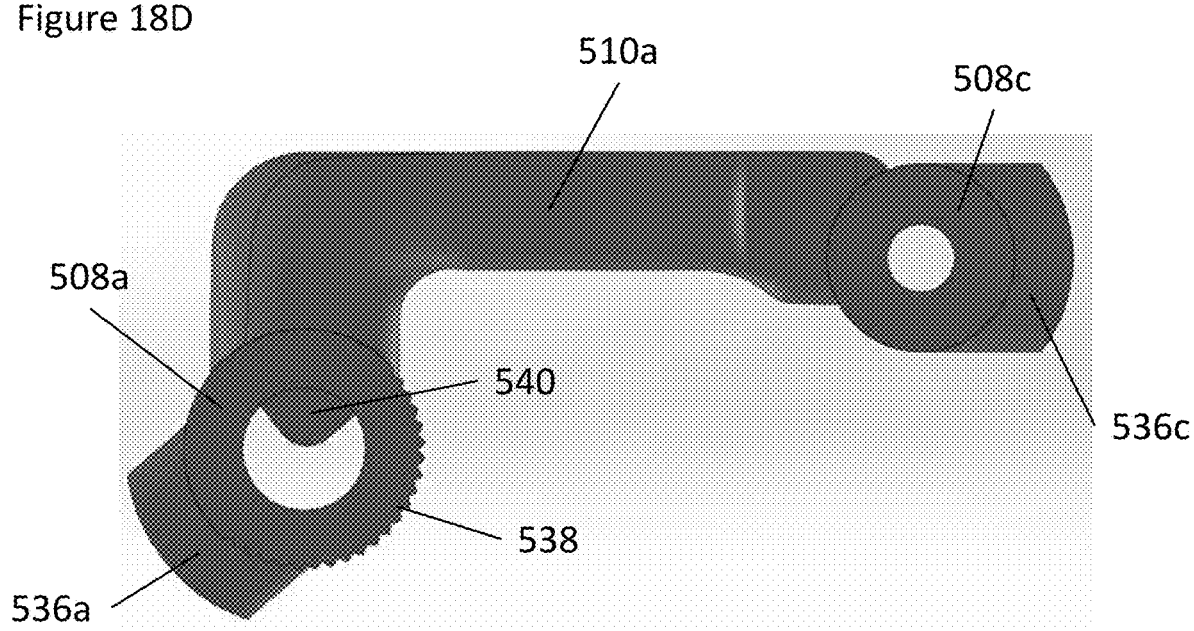

In some embodiments, an arm may further comprise features for engaging an insertion tool, described elsewhere herein. For example, arm 502a can comprise connector 520 having a threaded interior sized to fit a locking bit 522. Connector 520 comprises one or more attachment features 521 to mate with the insertion tool. Attachment features 521 may be indents as shown in FIG. 17C and FIG. 17D to fit the tongs of an insertion tool. Alternatively, attachment features 521 may be threads to threadably engage an insertion tool. Locking bit 522 can be actuated to lock into a bolt 508 (such as bolt 508a), thereby arresting movement in expandable device 500. In another example, arm 502b can comprise socket 518 to fit the driver horn of an insertion tool, described elsewhere herein.

Referring now to FIG. 18A through FIG. 18D, bolts 508a-508d are depicted with their respective crossbars 510a and 510b. Each bolt 508 comprises a cylindrical shape having a top end, a bottom end, and an outer surface. Each bolt 508 comprises four pin guides 530 cut into the outer surface. Each pin guide 530 is a curved slot having a closed position 532 near the center of bolt 508 and an open position 534 near the top and bottom ends of bolt 508. Closed position 532 and open position 534 are placed at an angle between about 60 and 130 degrees away from each other on the outer surface. Pin guides 530 are arranged on bolt 508 on the top half and the bottom half of bolt 508, such that a pin 512 can extend through each pin guide 530. Rotating each bolt 508 thereby slides a pin 512 through each pin guide 530 between a closed position 534 and an open position 534. Each bolt 508 further comprises a rounded cam 536 positioned on its outer surface, midway between the top end and bottom end of each bolt 508. For example, bolt 508a comprises cam 536a, bolt 508b comprises cam 536b, bolt 508c comprises cam 536c, and bolt 508d comprises cam 536d.

Bolts 508a-508d and crossbars 510a and 510b can have any suitable dimensions. In some embodiments, bolts 508a-508d each have the same dimensions. In some embodiments, bolts 508a-508d each have different dimensions or combinations of different dimensions. For example, bolts 508a and 508b are depicted as having a wider cylindrical shape than bolts 508c and 508d. Bolt 508a is also depicted having a plurality of ridges 538 on its outer surface, such as for engaging locking bit 522. In some embodiments, bolts 508 can have a boss 540 or other internal structure that limits the depth of pin 512 insertion. Crossbars 510a and 510b can also each have the same dimensions in some embodiments and different dimensions in some embodiments. For example, crossbar 510b is depicted as having a substantially cylindrical shape, while crossbar 510a is depicted as having an angled bend and a window 514.

Figure 19:
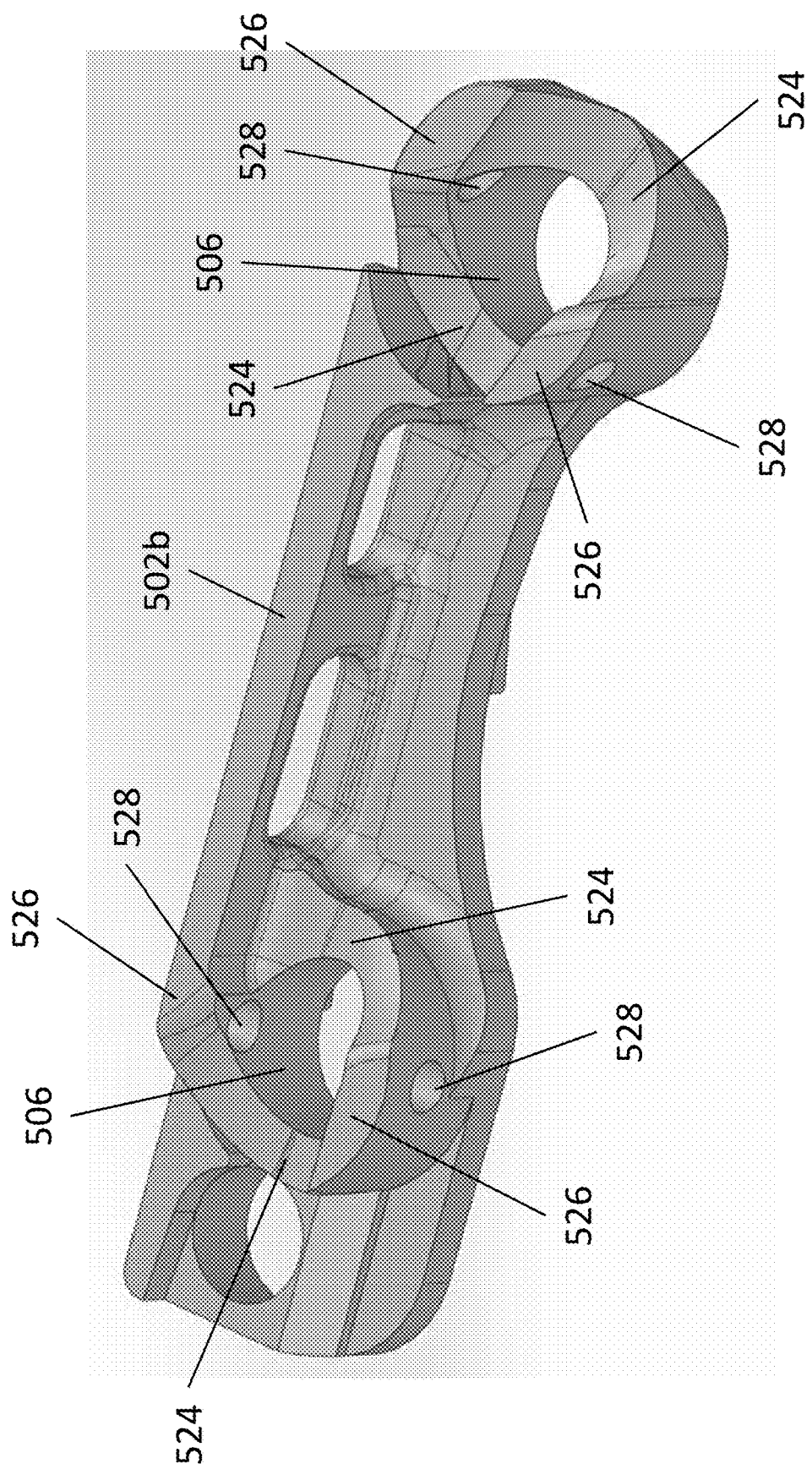
FIG. 19 depicts the interior of an arm of an exemplary expandable device in isolation.

Referring now to FIG. 19, the interior of arm 502b is depicted. The perimeter of each slot 506 comprises a variably sloping surface upon which cams 536 of each bolt 508 slides against as each bolt 508 rotates. For example, the variably sloping surface comprises opposing first cam faces 524 and opposing second cam faces 526. The opposing first cam faces 524 provide a space to hold a cam 536 and a crossbar 510 when expandable device 500 is in a closed configuration. The opposing second cam faces 526 have a different elevation than the opposing first cam faces 524, whereupon rotating each bolt 508 positions a cam 536 and a crossbar 510 to rest on the opposing second cam faces 526 when expandable device 500 is in an open configuration. Pin holes 528 are visible in each slot 506, which hold pins 512 stationary while bolts 508 are rotated. While arm 502b is depicted here, it should be understood that the description of the features of arm 502b are equally applicable to any of the arms of expandable device 500, including arm 502a, 504a, and 504b.

Figure 20A:
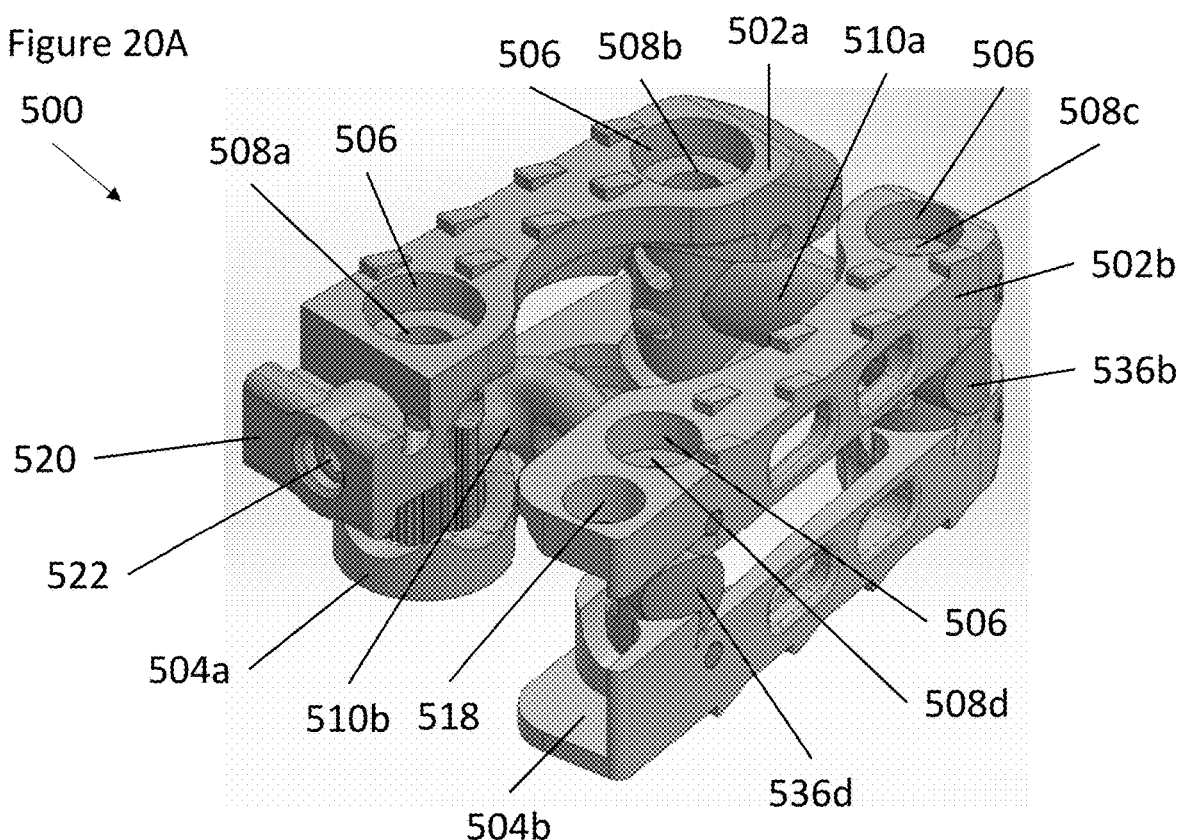
FIG. 20A through FIG. 20C depict a perspective view, a top view, and a rear view of an exemplary expandable device in an open configuration.
Figure 20B:
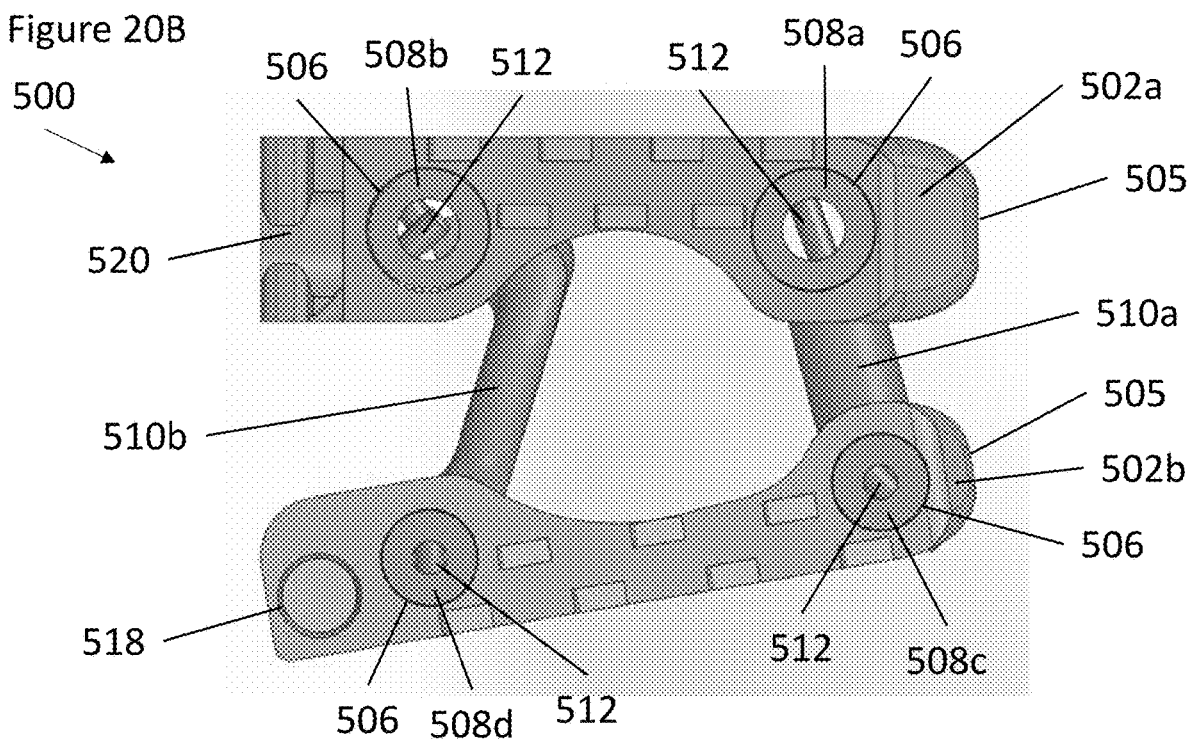
Figure 20C:
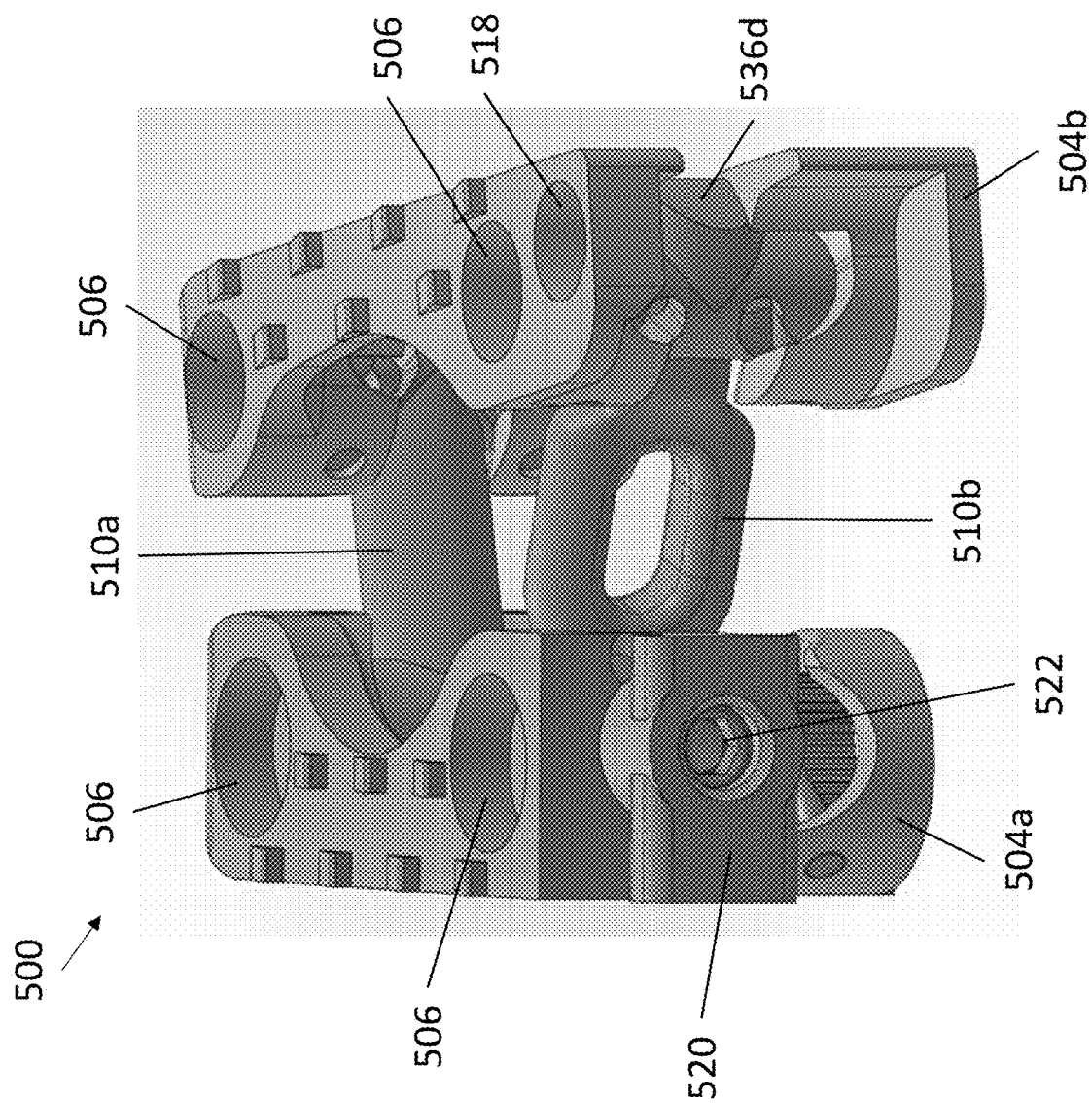

In FIG. 20A through FIG. 20C, expandable device 500 is depicted in an open configuration. As described above, rotating each of bolt 508a-508d shifts expandable device 500 between a fully closed position and a fully open position. The shift is achieved by two mechanisms: the first is the positioning of each pin 512 in each pin guide 530 between a closed position 532 and an open position 534; the second is the positioning of the cams 536 and crossbars 510 between the opposing first cam faces 524 and the opposing second cam faces 526 of each arm 502a, 502b, 504a, and 504b. Compressive forces acting on expandable device 500 in an open configuration are thereby supported by each pin 512 in a pin guide 530, as well as each cam face 524 and crossbar 510 pressing against the variably sloping surface on the periphery of each slot 506 at each cam face 524, each cam face 526, and positions therebetween.

The arrangement of bolts 508a-508d, pins 512, pin guides 530, cams 536, and opposing cam faces 524 and 526 synchronize the simultaneous movement between each arm 502a, 502b, 504a, and 504b. Shifting expandable device 500 from a closed configuration to an open configuration separates superior arms 502a and 502b from inferior arms 504a and 504b at the same rate and distance. Shifting expandable device 500 from a closed configuration to an open configuration also separates arms 502a and 504a from arms 502b and 504b. In some embodiments, arms 502a and 504a are separated from arms 502b and 504b in parallel at the same rate and distance. In some embodiments, wherein crossbar 510a and 510b have different dimensions, arms 502a and 504a are separated from arms 502b and 504b at an angle.

The exemplary expandable device 500 is depicted as having a polyhedron-like shape with four rectangular sides and a parallelogram-like top and bottom when closed (FIG. 17A through FIG. 17D), and an asymmetrical polyhedron-like shape with four rectangular sides and a substantially trapezoidal top and bottom when open (FIG. 20A through FIG. 20C). However, it should be understood that expandable device 500 is not limited to the depicted shapes, and can have any suitable shape. For example, each of the arms 502a, 502b, 504a, and 504b can comprise a semicircular shape to give expandable device 500 an overall cylindrical shape having curved sides and a circular or oval top and bottom.

In some embodiments, one or more of the bolts 508 can have pin guides 530 with different open positions 534 (not pictured). For example, bolt 508a and bolt 508c can each have pin guides 530 with an open position 534 at a first height, and bolt 508b and bolt 508d can each have pin guides 530 with an open position 534 at a second height, such that superior arms 502a and 502b are separated from inferior arms 504a and 504b by a first height at one end and by a second height at an opposing end. In this manner, expandable device 500 can thereby maintain substantially rectangular sides when closed, and has a lordotic angle with a substantially trapezoidal left and right side when open. A similar effect can be achieved by having second cam faces 526 with differing elevations in each arm 502a, 502b, 504a, and 504b.

Expandable device 500 can have any suitable dimensions between its closed and open configurations. For example, in certain embodiments, expandable device 500 can have a closed length of between 30 mm to 30 cm, a closed width of between 7 mm to 7 cm, and a closed height of between 8 mm and 8 cm. In certain embodiments, expandable device 500 can have an open length of between 20 mm to 20 cm, an open width of between 10 mm to 10 cm, and an open height of between 10 mm and 10 cm. The surface area and footprint of expandable device 500 will depend on the length, width, and height, and will change accordingly between open and closed configurations. The surface area of expandable device 500 will further depend on modifications to expandable device 500, such as the number of windows 514.

Third Insertion Tool for the Third Expandable Device

Figure 21:
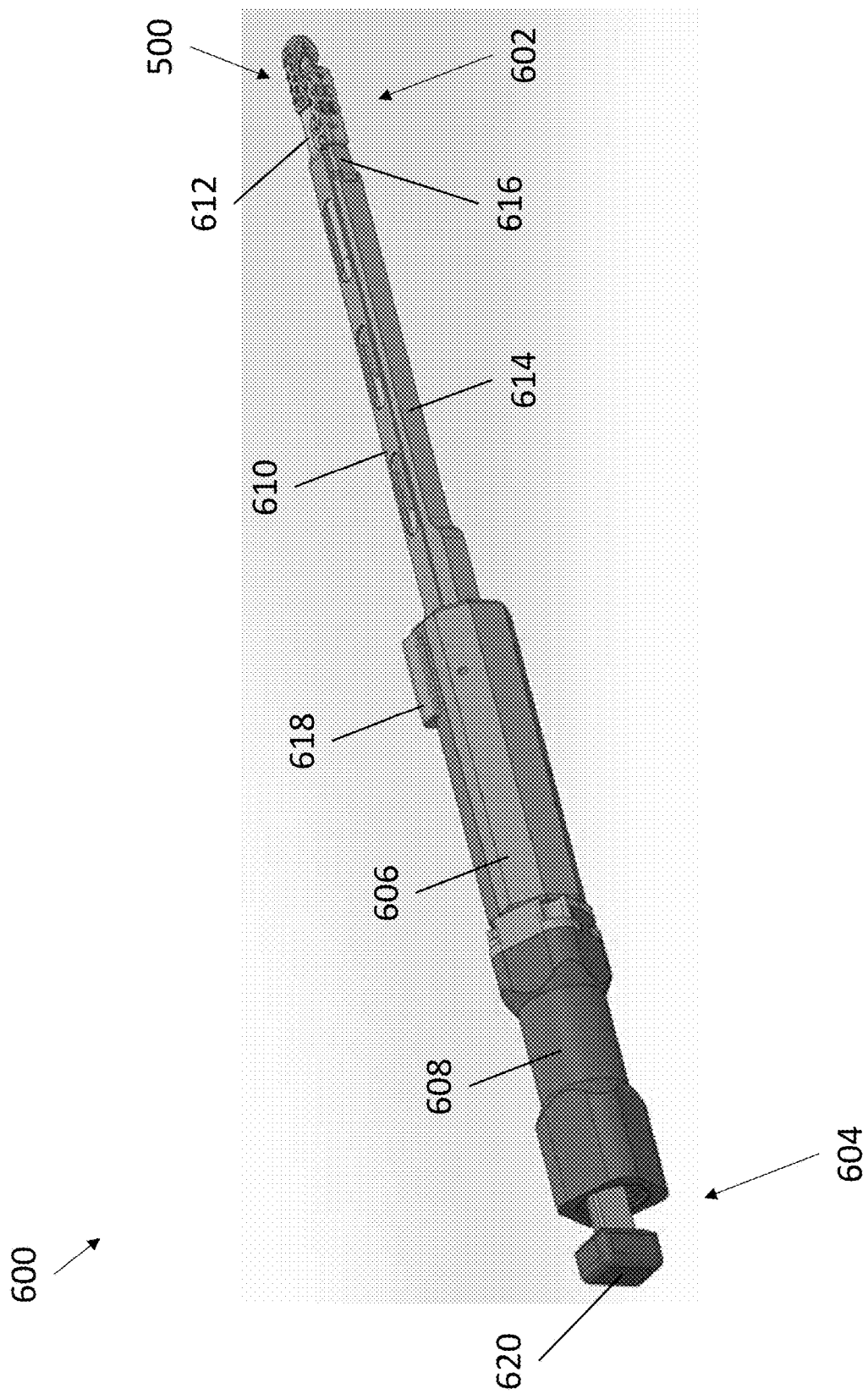
FIG. 21 depicts a perspective view of an exemplary insertion tool.

Referring now to FIG. 21, an exemplary insertion tool 600 is depicted. Insertion tool 600 comprises an anterior end 602, a posterior end 604, a nonrotating handle 606, a rotating handle 608, a locking sleeve 610, tongs 612, a deployment driver 614, a driver horn 616, and a backstop 618.

Figure 22A:
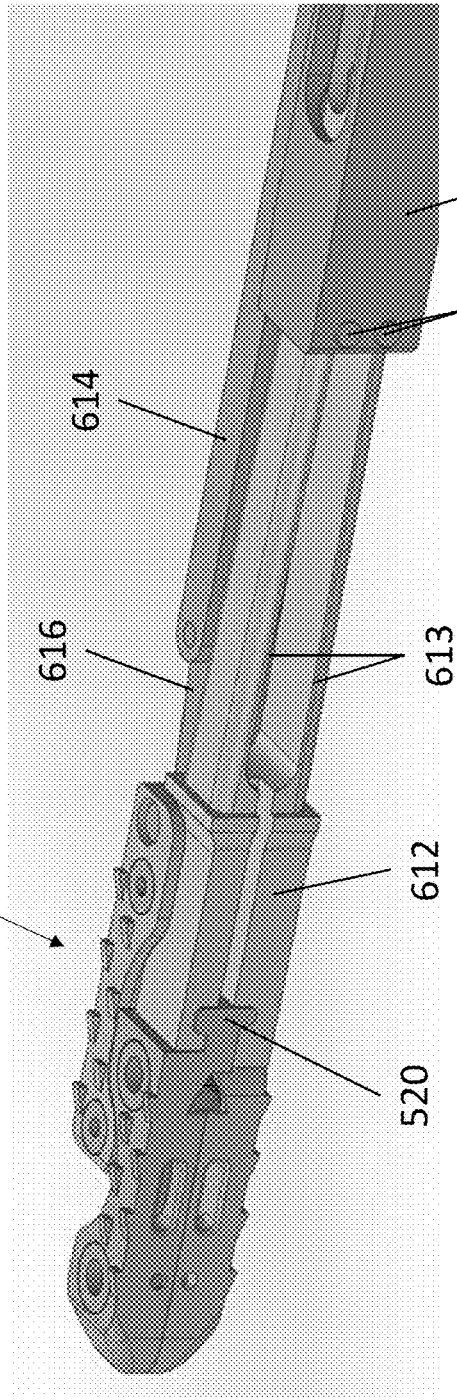
FIG. 22A through FIG. 22D depict perspective views of an exemplary insertion tool engaged to an exemplary expandable device.
Figure 22B:
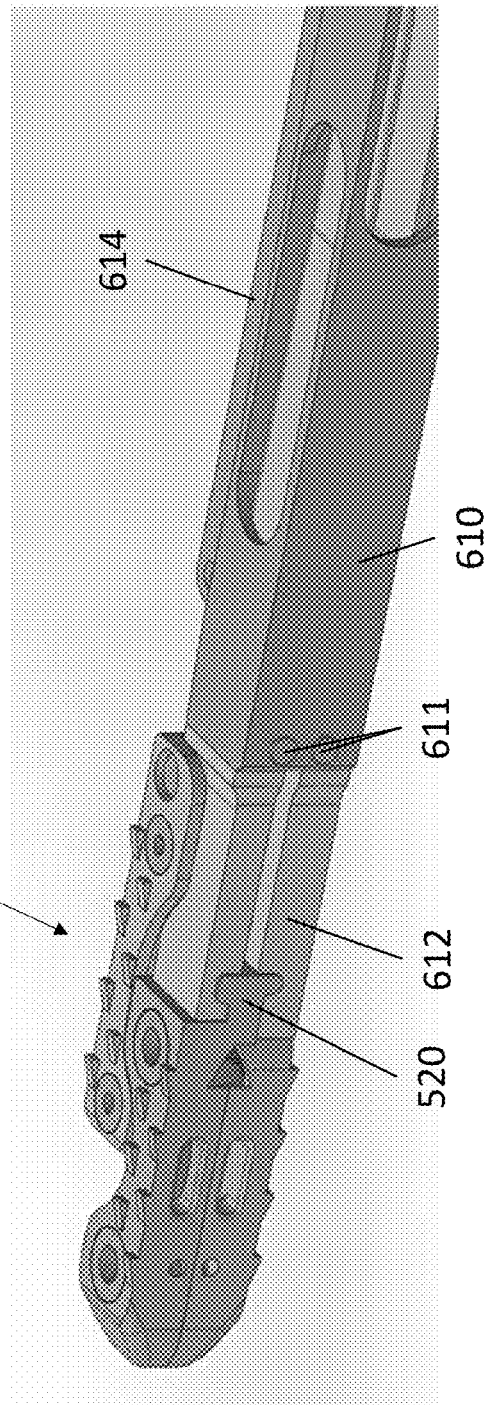
Figure 22C:
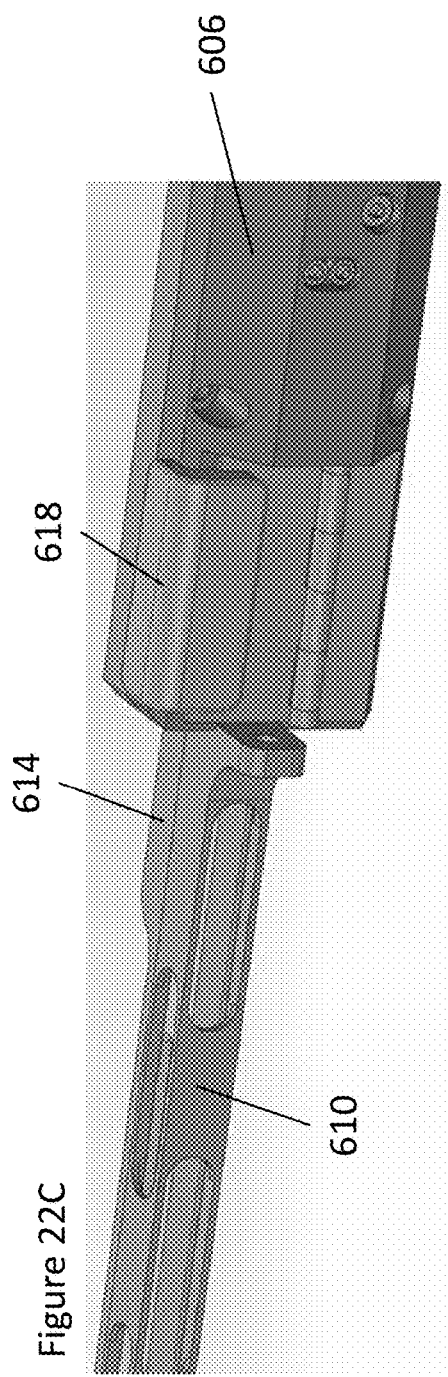
Figure 22D:
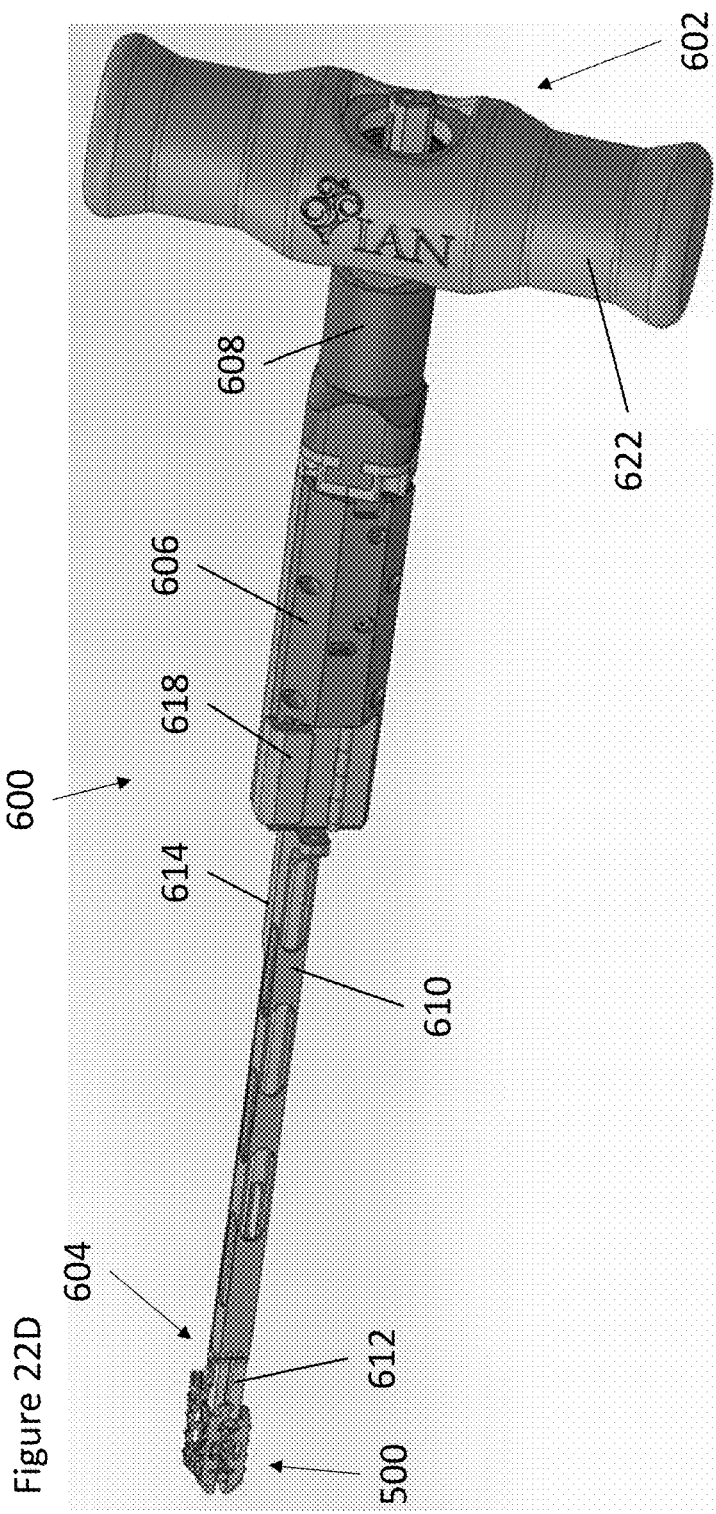

Nonrotating handle 606 has a lumen through which deployment driver 614 extends. Rotating handle 608 comprises a lumen and is rotatable about nonrotating handle 606 to advance deployment driver 614 in a posterior and anterior direction. In some embodiments, torque handle 622 can be attached to the posterior end of rotating handle 608 (FIG. 22D). Torque handle 622 can be constructed from a rigid material, and can provide increased leverage to facilitate the rotation of rotating handle 608.

Tongs 612 immovably extend from nonrotating handle 606 in an anterior direction. As shown in FIG. 22A and FIG. 22B, Tongs 612 are expandable at anterior end 604, enabling the anterior end of tongs 612 to engage to connector 520 of expandable device 500. Tongs 612 comprise a lumen extending from posterior end 602 to anterior end 604, wherein the lumen of tongs 612 is aligned with locking bit 522 when engaged to expandable device 500. Locking sleeve 610 is slidable along tongs 612 and restricts the expansion of tongs 612 when placed in an anterior-most position. In some embodiments, locking sleeve 610 comprises pins 611 slidable along upper and lower angled surfaces 613 of tongs 612, such that when locking sleeve 610 is in a posterior-most position, pins 611 are pressed against the upper and lower angled surfaces 613, forcing tongs 612 to expand open. In some embodiments, a stopper can be engaged to secure locking sleeve 610 in an anterior-most position. The stopper can include a screw or a clamp, such as backstop 618 (FIG. 22C).

In some embodiments, striker cap 620 can be attached to the posterior end of the lumen of tongs 612. Striker cap 620 can be constructed from a shock absorbing material such as rubber or plastic, and can receive hammer strikes to drive an engaged expandable device 500 into a subject while protecting the device features at posterior end 604 of insertion tool 600.

Figure 23A:
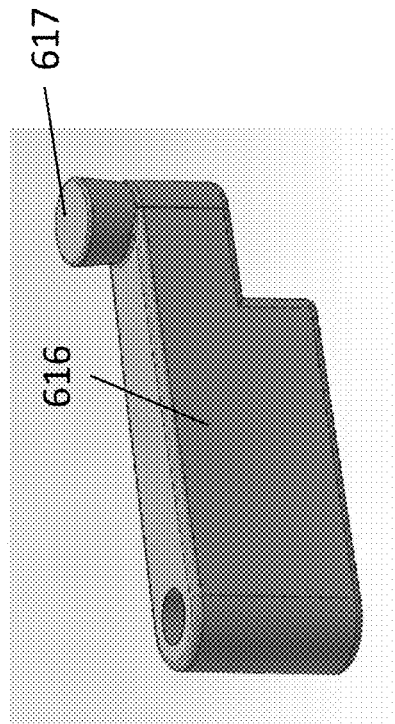
FIG. 23A and FIG. 23B depict a driver horn and deployment driver of an exemplary insertion tool and the driver horn engaged to an exemplary expandable device, respectively.
Figure 23B:
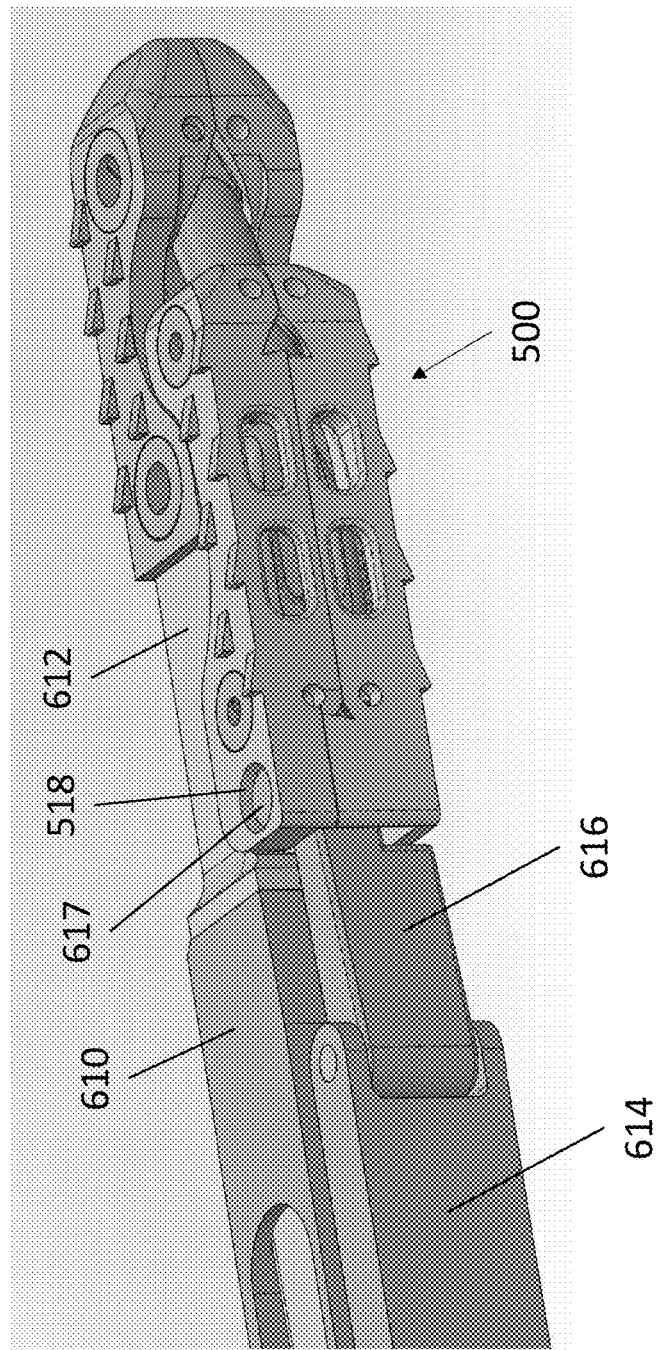

Referring now to FIG. 23A and FIG. 23B, deployment driver 614 is depicted in more detail. Deployment driver 614 comprises driver horn 616 hingedly connected at its anterior end. Driver horn 616 comprises peg 617 sized to fit within socket 518 of expandable device 500. The hinged connection permits driver horn 616 to adapt to an expanding device 500 while deployment driver 614 remains flush against tongs 612 and locking sleeve 610.

Figure 24:
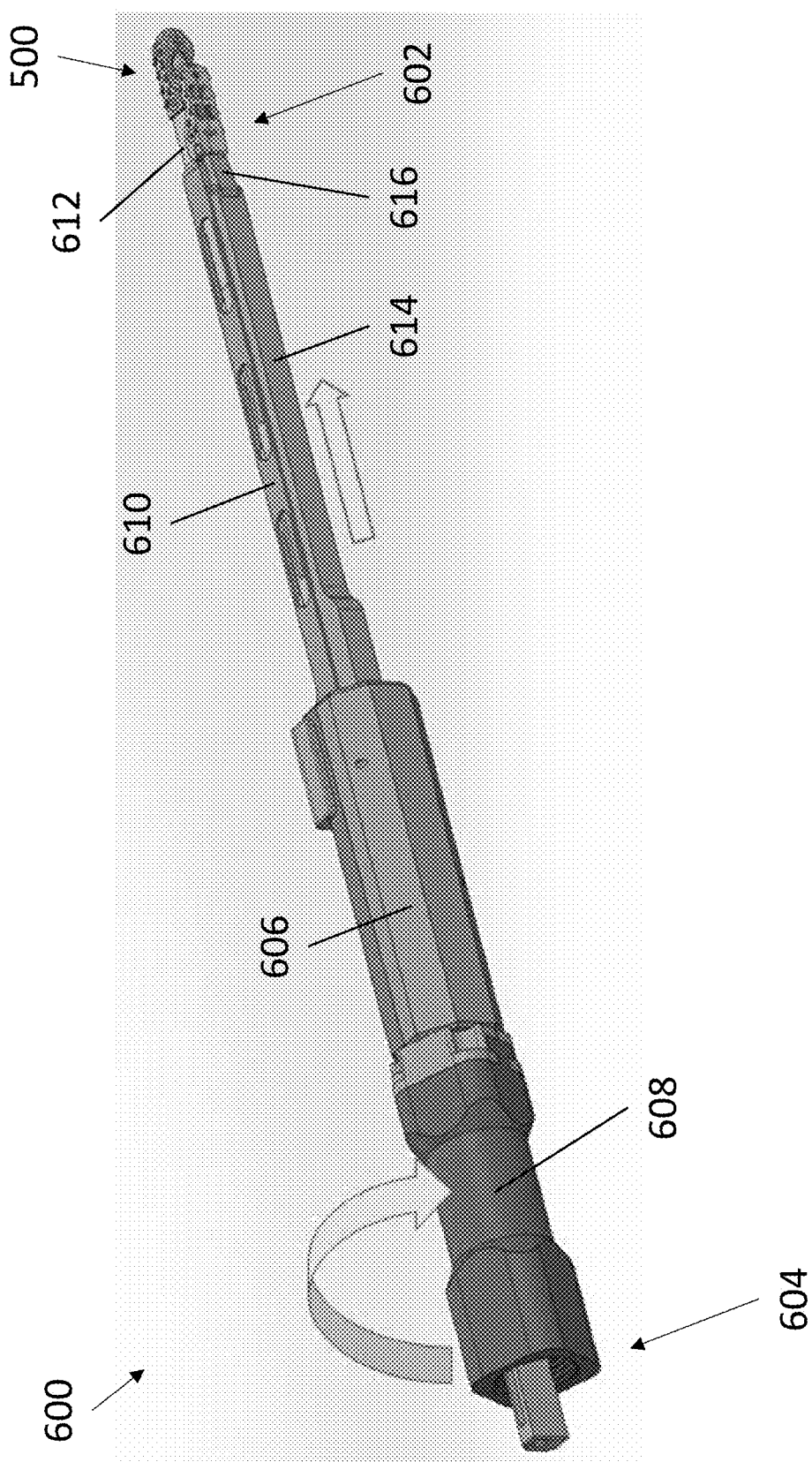
FIG. 24 depicts a perspective view of an exemplary insertion tool indicating the operation of driving the deployment driver.

As described above, an expandable device 500 can be engaged to the anterior end 604 of an insertion tool 600 by clamping the anterior end of tongs 612 around connector 520. Tongs 612 are secured around connector 520 by advancing locking sleeve 610 into an anterior-most position, and locking sleeve 610 is locked in place by engaging backstop 618. Deployment driver 614 can be engaged to expandable device 500 by inserting peg 617 of driver horn 616 into socket 518. Referring now to FIG. 24, rotating handle 608 is rotated about nonrotating handle 606 to push deployment driver 614 in an anterior direction, whereupon arm 502b is pushed in an anterior direction while arm 502a is held stationary by tongs 612. The expansion of an expandable device 500 using insertion tool 600 is shown in sequence in FIG. 25A through FIG. 25D. The relocation of arm 502b relative to arm 502a leads to the synchronized series of movements described elsewhere herein, shifting expandable device 500 from a closed configuration to an open configuration. As will be understood by those having skill in the art, expandable device 500 can be shifted from an open configuration to a closed configuration by reversing the rotation of rotating handle 608, which pulls deployment driver 614 and arm 502b in a posterior direction.

Referring now to FIG. 26A and FIG. 26B, expandable device 500 can be locked into any position between its open configuration and its closed configuration by sliding locking bit driver 624 into the lumen of tongs 612 to seat locking bit driver 624 into locking bit 522. Locking bit driver 624 can be twisted to drive locking bit 522 into bolt 508a, locking its rotation as well as the movement of every other interconnected piece. As described elsewhere herein, bolt 508a can include ridges 538 on its outer surface, enhancing the locking grip of locking bit 522.

Figure 27A:
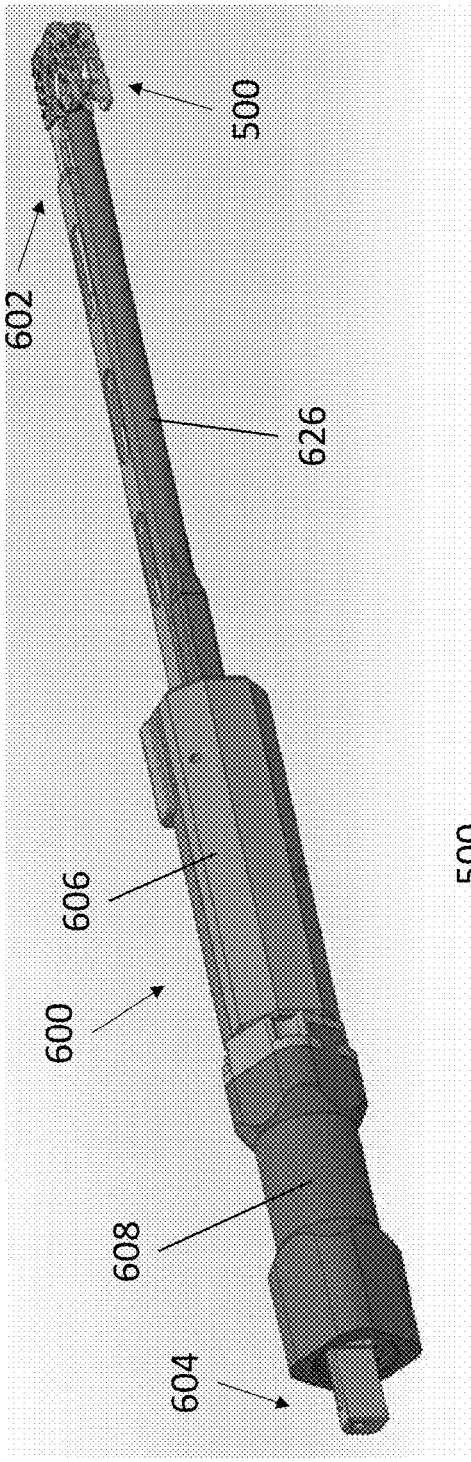
FIG. 27A through FIG. 27C depict the use of a funnel with an exemplary insertion tool to introduce material to an exemplary opened expandable device.
Figure 27C:
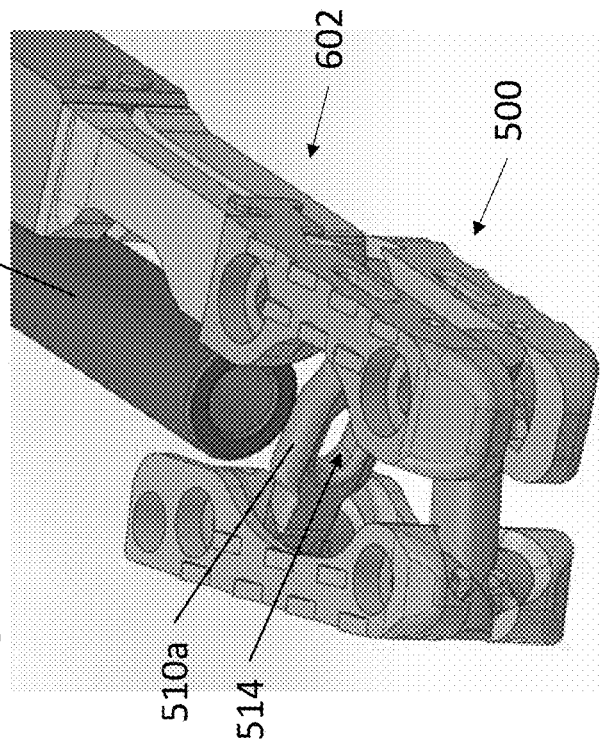
Figure 27B:
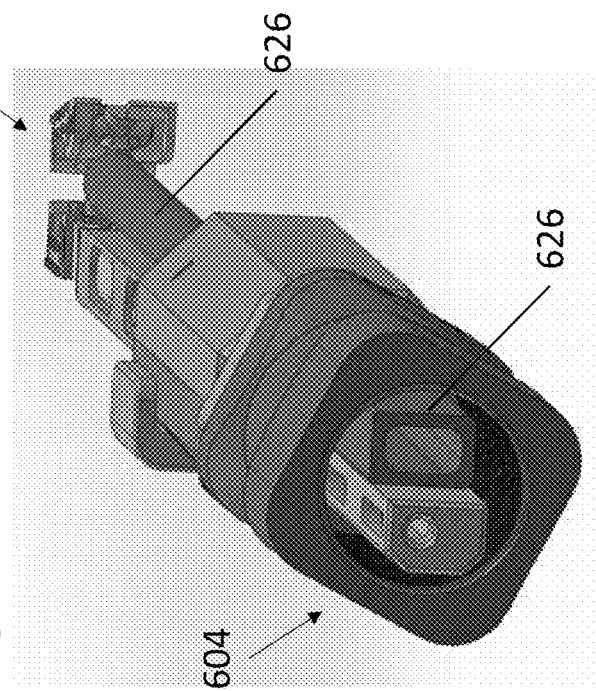

In some embodiments, deployment driver 614 can be removed from insertion tool 600 and replaced with funnel 626. As shown in FIG. 27A through FIG. 27C, funnel 626 can be inserted through the lumens of rotating handle 608 and nonrotating handle 606 to position the anterior end of funnel 626 adjacent to expandable device 500. Funnel 626 comprises a lumen running from its posterior end to its anterior end, wherein the lumen is aligned with the open space of the separation between the arms of an expanded device 500. Funnel 626 can thereby be used to deposit a material, such as bone graft or tissue. Funnel 626 can also be used to accurately guide instruments to an expanded device 500. As described elsewhere herein, expandable device 500 can include a crossbar 510a having a window 514 to facilitate access to an expanded device 500.

Fourth Expandable Device

Figure 28A:
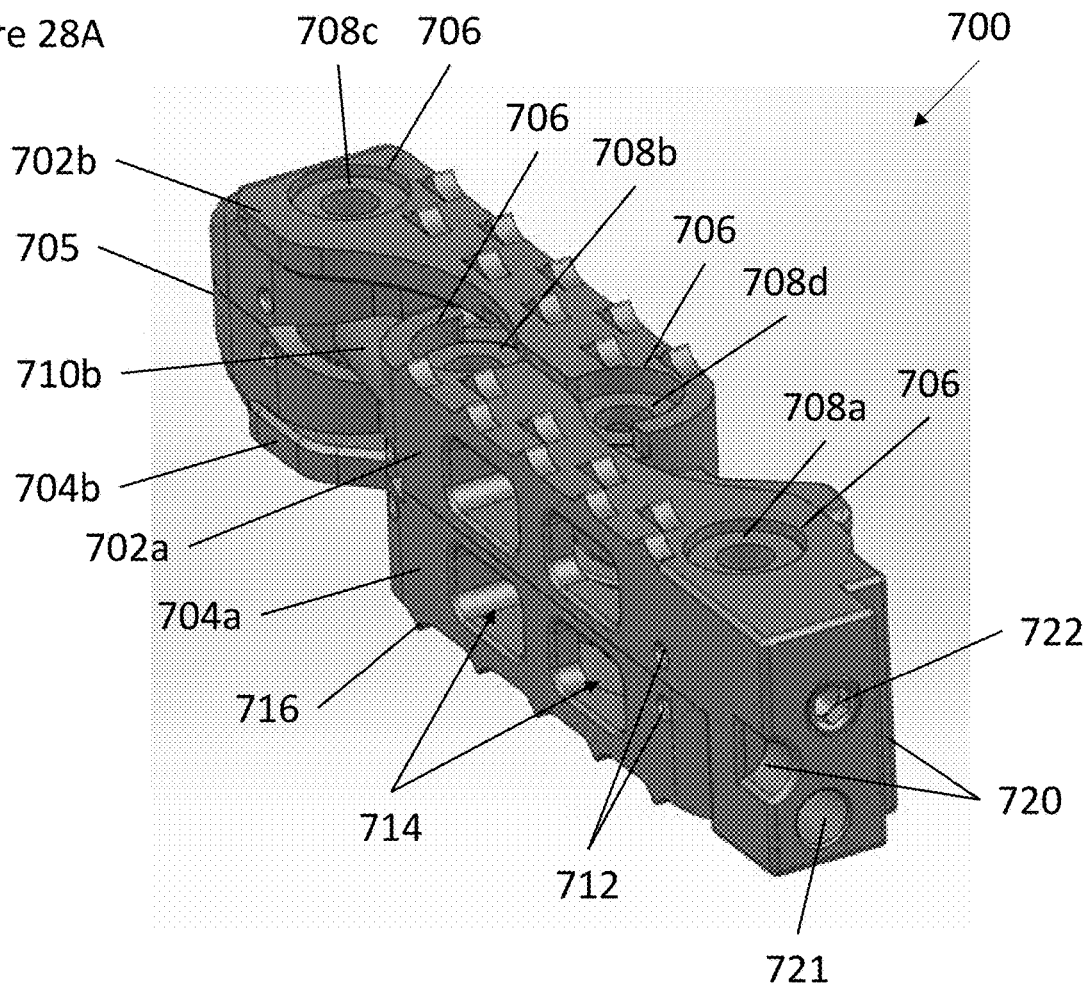
FIG. 28A and FIG. 28B depict perspective views of an exemplary expandable device in a closed configuration and the anterior end of an exemplary insertion device, respectively.

Referring now to FIG. 28A, an exemplary expandable device 700 is depicted. Expandable device 700 comprises four arms (superior first arm 702a, superior second arm 702b, inferior third arm 704a, and inferior fourth arm 704b) and four movable bolts 708 (referred to herein as posterior first bolt 708a, anterior second bolt 708b, posterior third bolt 708c, and anterior fourth bolt 708d). Each arm comprises two slots 706 sized to fit a movable bolt 708. Each bolt 708 is secured within a slot 706 by a pin 712 fixed to each arm. Bolt 708a is secured to bolt 708c by crossbar 710a, and bolt 708b is secured to bolt 708d by crossbar 710b, described elsewhere herein.

Arms 702a, 702b, 704a, 704b, bolts 708a-708d, and pins 712 are preferably constructed from a rigid material, such as a metal or a hard polymer. In various embodiments, the rigid material is a biocompatible material. In certain embodiments, each arm can comprise a surface that is textured or at least partially covered with barbs or spikes to improve the attachment of expandable device 700 within a space, such as barbs 716. In certain embodiments, each arm can terminate in a taper 705 at an anterior end, wherein taper 705 facilitates entry of expandable device 700 into a space.

In various embodiments, each arm can comprise a plurality of windows 714. Windows 714 may be placed throughout each arm without compromising the rigidity of expandable device 700. Windows 714 can be filled with any component that is synergistic with the function of expandable device 700. For example, in some embodiments, windows 714 can be packed with a biological material to promote the ingrowth of tissue, such as bone. In some embodiments windows 714 can be packed with a therapeutic to treat surrounding tissue. In some embodiments, one or more sensors can be inserted into windows 714 to monitor the device and its environs, such as a temperature sensor, pressure sensor, corrosion sensor, and the like. In some embodiments, windows 714 can be used to secure expandable device 700 within a space, by accepting screws or cement. Windows 714 can also be used to view and monitor the progress of bone growth into the interior of expandable device 700.

In some embodiments, an arm may further comprise features for engaging an insertion tool, described elsewhere herein. For example, arm 702a can comprise connector 720 having a threaded screw hole 721 and a locking bit 722. Locking bit 722 can be actuated to lock into a bolt 708 (such as bolt 708a), thereby arresting movement in expandable device 700. Visible in FIG. 30B, crossbar 710b can comprise rung 711 that can be pulled or pushed.

While not shown in detail, the mechanism by which expandable device 700 transitions between a closed configuration and an open configuration uses a system of bolts, crossbars, pins, cams, and cam faces similar to those described elsewhere herein. Briefly, bolts 708a-708d are connected by their respective crossbars 710a and 710b. Each bolt 708 comprises a cylindrical shape having a top end, a bottom end, and an outer surface. Each bolt 708 comprises four pin guides cut into the outer surface. Each pin guide is a curved slot having a closed position near the center of bolt 708 and an open position near the top and bottom ends of bolt 708. The closed positions and open positions are placed at an angle between about 60 and 130 degrees away from each other on the outer surface. The pin guides are arranged on bolt 708 on the top half and the bottom half of bolt 708, such that a pin can extend through each pin guide. Rotating each bolt 708 thereby slides a pin through each pin guide between a closed position and an open position. Each bolt 708 further comprises a rounded cam positioned on its outer surface, midway between the top end and bottom end of each bolt 708.

On the interior of each arm 702a, 702b, 704a, and 704b the perimeter of each slot 706 comprises a variably sloping surface upon which the cams of each bolt 708 slides against as each bolt 708 rotates. For example, the variably sloping surface comprises opposing first cam faces and opposing second cam faces. The opposing first cam faces provide a space to hold a cam and a crossbar when expandable device 700 is in a closed configuration. The opposing second cam faces have a different elevation than the opposing first cam faces, whereupon rotating each bolt 708 positions a cam and a crossbar to rest on the opposing second cam faces when expandable device 700 is in an open configuration.

Rotating each of bolt 708a-708d shifts expandable device 700 between a fully closed position and a fully open position. The shift is achieved by two mechanisms: the first is the positioning of each pin in each pin guide between a closed position and an open position; the second is the positioning of the cams and crossbars between the opposing first cam faces and the opposing second cam faces of each arm 702a, 702b, 704a, and 704b. Compressive forces acting on expandable device 700 in an open configuration are thereby supported by each pin in a pin guide, as well as each cam face and crossbar pressing against the variably sloping surface on the periphery of each slot 706.

The arrangement of bolts 708a-708d, pins, pin guides, cams, and opposing cam faces synchronize the simultaneous movement between each arm 702a, 702b, 704a, and 704b. Shifting expandable device 700 from a closed configuration to an open configuration separates superior arms 702a and 702b from inferior arms 704a and 704b at the same rate and distance. Shifting expandable device 700 from a closed configuration to an open configuration also separates arms 702a and 704a from arms 702b and 704b. In some embodiments, arms 702a and 704a are separated from arms 702b and 704b in parallel at the same rate and distance. In some embodiments, wherein crossbar 710*a* and 710*b* have different dimensions, arms 702*a* and 704*a* are separated from arms 702*b* and 704*b* at an angle.

The exemplary expandable device 700 is depicted as having a polyhedron-like shape with four rectangular sides and a parallelogram-like top and bottom when closed (FIG. 28A), and a polyhedron-like shape with four rectangular sides and a rectangular top and bottom when open (FIG. 31E). However, it should be understood that expandable device 700 is not limited to the depicted shapes, and can have any suitable shape. For example, each of the arms 702*a*, 702*b*, 704*a*, and 704*b* can comprise a semicircular shape to give expandable device 700 an overall cylindrical shape having curved sides and a circular or oval top and bottom.

In some embodiments, one or more of the bolts 708 can have pin guides with different open positions (not pictured). For example, bolt 708*a* and bolt 708*c* can each have pin guides with an open position at a first height, and bolt 708*b* and bolt 708*d* can each have pin guides with an open position at a second height, such that superior arms 702*a* and 702*b* are separated from inferior arms 704*a* and 704*b* by a first height at one end and by a second height at an opposing end. In this manner, expandable device 700 can thereby maintain substantially rectangular sides when closed, and has a lordotic angle with a substantially trapezoidal left and right side when open. A similar effect can be achieved by having second cam faces with differing elevations in each arm 702*a*, 702*b*, 704*a*, and 704*b*.

Expandable device 700 can have any suitable dimensions between its closed and open configurations. For example, in certain embodiments, expandable device 700 can have a closed length of between 30 mm to 30 cm, a closed width of between 7 mm to 7 cm, and a closed height of between 8 mm and 8 cm. In certain embodiments, expandable device 700 can have an open length of between 20 mm to 20 cm, an open width of between 10 mm to 10 cm, and an open height of between 10 mm and 10 cm. The surface area and footprint of expandable device 700 will depend on the length, width, and height, and will change accordingly between open and closed configurations. The surface area of expandable device 700 will further depend on modifications to expandable device 700, such as the number of windows 714.

Fourth Insertion Tool for the Fourth Expandable Device

Figure 28B:
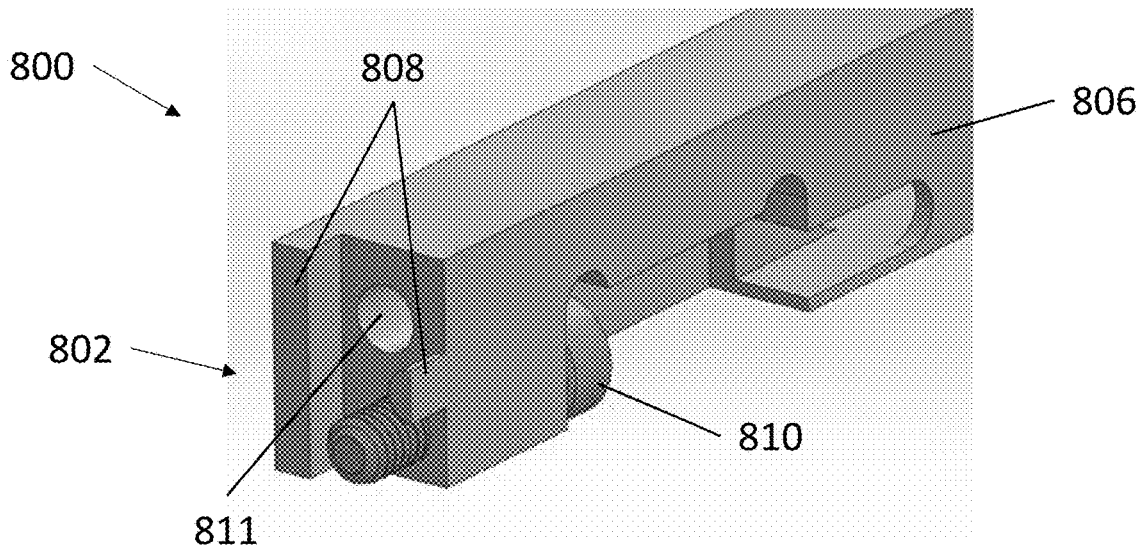

Referring now to FIG. 28B, the anterior end 802 of an exemplary insertion tool 800 is depicted. Insertion tool 800 comprises at least a shaft 806, tabs 808, screw 810, and aperture 811 connected to a lumen.

Figure 29A:
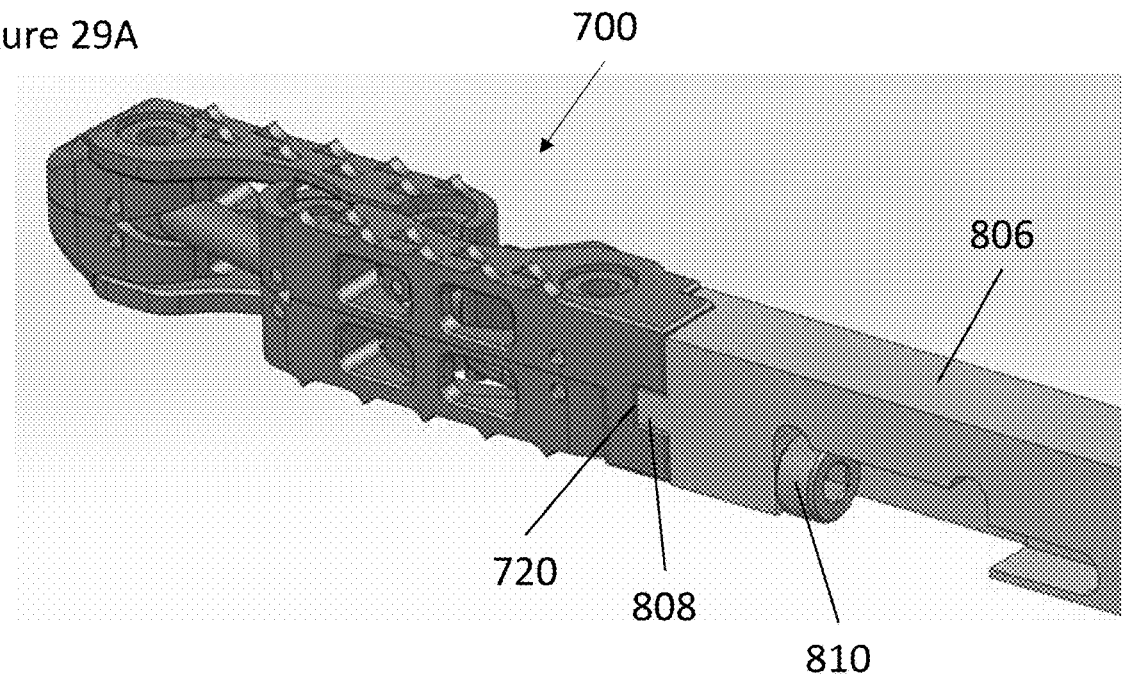
FIG. 29A and FIG. 29B depict perspective views of an exemplary expandable device engaged to an exemplary insertion device.
Figure 29B:
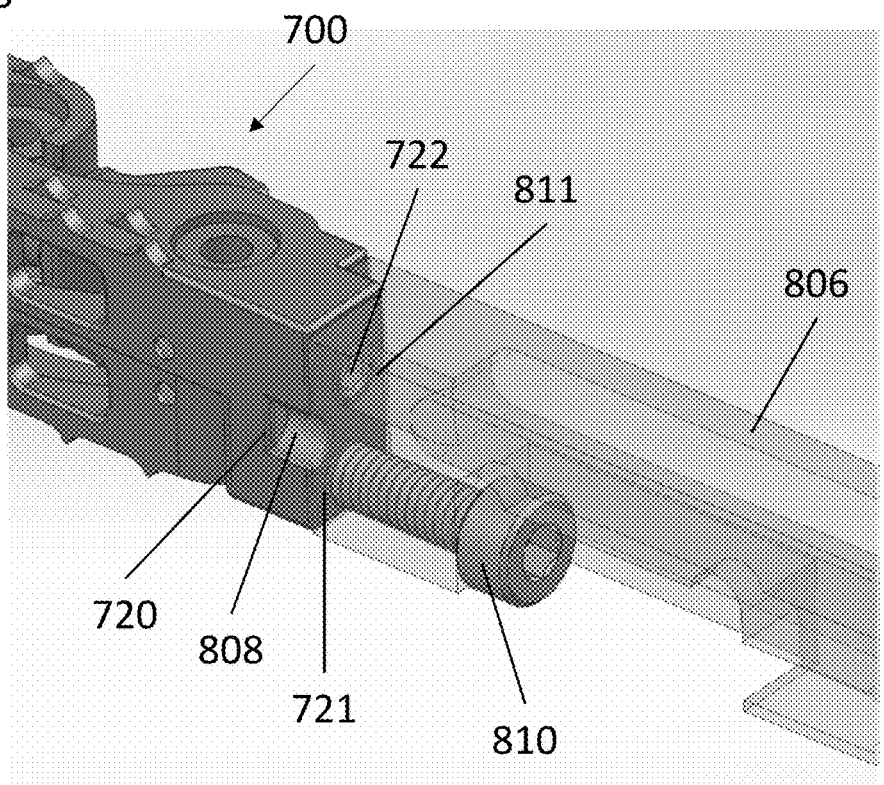

As shown in FIG. 29A and FIG. 29B, insertion tool 800 engages to expandable device 700 by mating tabs 808 with connector 720. The engagement aligns screw 810 with screw hole 721, enabling screw 810 to be screwed into screw hole 721. In some embodiments, shaft 806 comprises a lumen running throughout, the lumen being aligned with screw 810, permitting the driving of screw 810 by an extended screwdriver. The engagement also aligns aperture 811 with locking bit 722, permitting the driving of locking bit 722 by an extended locking bit driver.

Figure 30A:
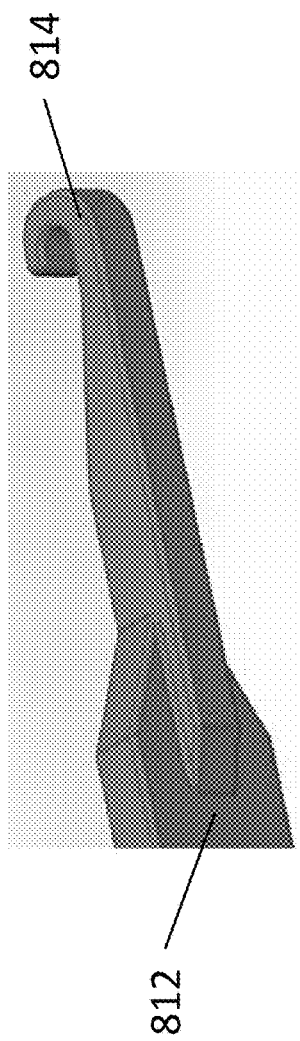
FIG. 30A and FIG. 30B depict a pull rod of an exemplary insertion tool and the pull rod engaged to an exemplary expandable device, respectively.
Figure 30B:
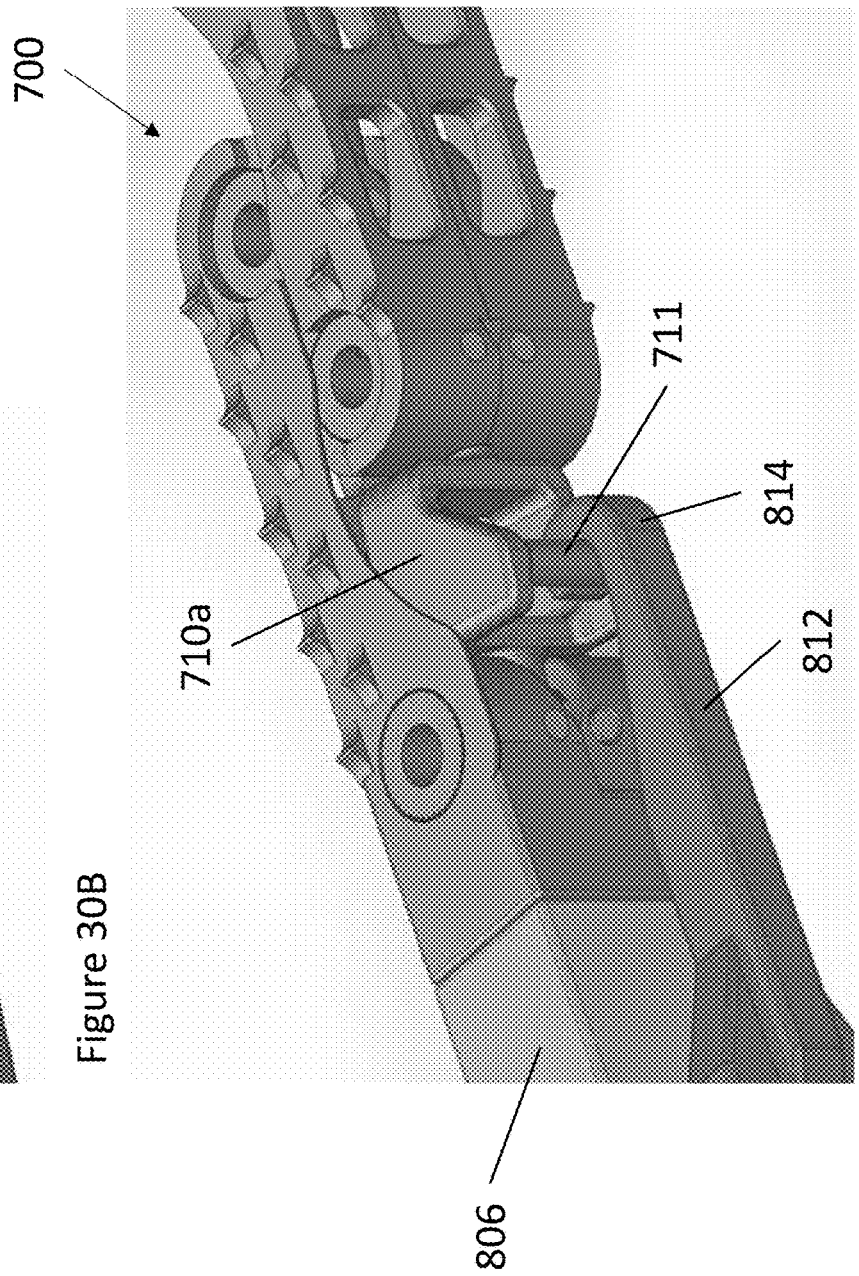

Referring now to FIG. 30A and FIG. 30B, a deployment pull rod 812 is depicted. Deployment pull rod 812 comprises hook 814 at its anterior end. Hook 814 is sized to fit over rung 711 of expandable device 700. Referring now to FIG. 31A through FIG. 31E, the expansion of an expandable device 700 using insertion tool 800 is shown in sequence. As described above, an expandable device 700 can be engaged to the anterior end 804 of an insertion tool 800 by mating tabs 808 with connector 720 and screwing in screw 810 into screw hole 721. Deployment pull rod 812 can be engaged to expandable device 700 by fitting hook 814 onto rung 711. Deployment pull rod 812 is advanced in a posterior direction, whereupon crossbar 710*b* pulls arm 702*b* in a posterior direction while arm 702*a* is held stationary by shaft 806. The relocation of arm 702*b* relative to arm 702*a* leads to the synchronized series of movements described elsewhere herein, shifting expandable device 700 from a closed configuration to an open configuration.

Figure 32A:
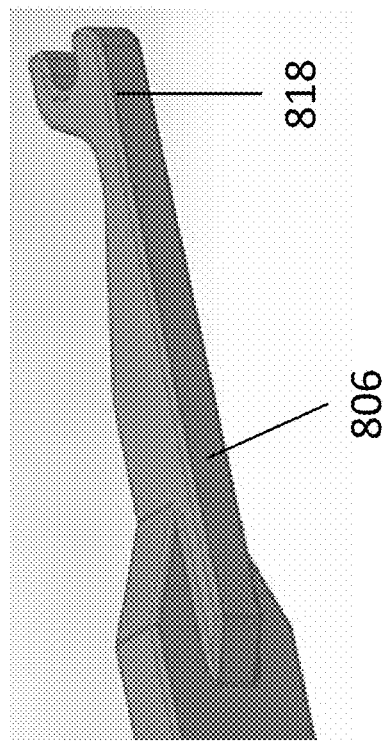
FIG. 32A and FIG. 32B depict a push rod of an exemplary insertion tool and the push rod engaged to an exemplary expandable device, respectively.
Figure 32B:
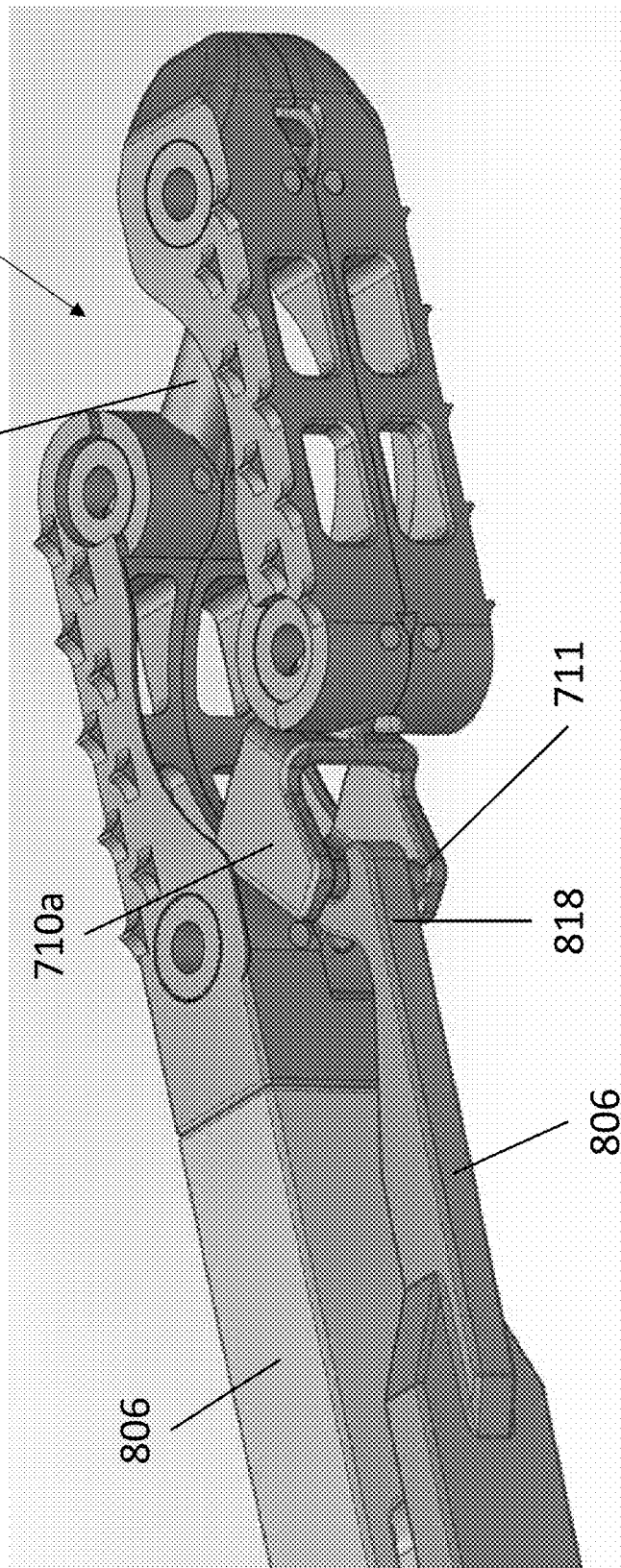

Referring now to FIG. 32A and FIG. 32B, a push rod 816 is depicted. Push rod 816 comprises stirrup 818 at its anterior end. Stirrup 818 is sized to fit rung 71 of expandable device 700. Expandable device 700 can be shifted from an open configuration to a closed configuration by pushing push rod 816 in an anterior direction, which pushes crossbar 710*a* and arm 702*b* in an anterior direction.

Methods of Making

The devices of the present invention can be made using any suitable method known in the art. The method of making may vary depending on the materials used. For example, devices substantially comprising a metal may be milled from a larger block of metal or may be cast from molten metal. Likewise, components substantially comprising a plastic or polymer may be milled from a larger block, cast, or injection molded. In some embodiments, the devices may be made using 3D printing or other additive manufacturing techniques commonly used in the art.

Methods of Use

The present invention also includes methods of using expandable devices. As described elsewhere herein, the expandable devices of the present invention are switchable between a compact closed configuration and an expanded open configuration and are capable of withstanding compressive forces in the expanded open configuration. The expandable devices are useful in any application requiring the maintenance of a space under load.

In one embodiment, the expandable devices of the present invention are useful as interbody devices. For example, in the case of intervertebral disc removal in a patient, the expandable devices of the present invention are useful as an interbody device to complete the spinal fusion procedure. The rigidity of the expandable devices enables stable, long term maintenance of the disc space void in an open configuration. The expandable devices can also be inserted in a less invasive manner due to their compact closed configuration. In a typical spinal fusion procedure, a skin incision is made adjacent to an intervertebral disc that requires removal. The disc space is identified, and the annulus of the disc is opened. Any suitable tools and techniques may be used to evacuate the intervertebral disc from the disc space and to prepare the adjoining bony endplates for good bony ingrowth.

Figure 33:
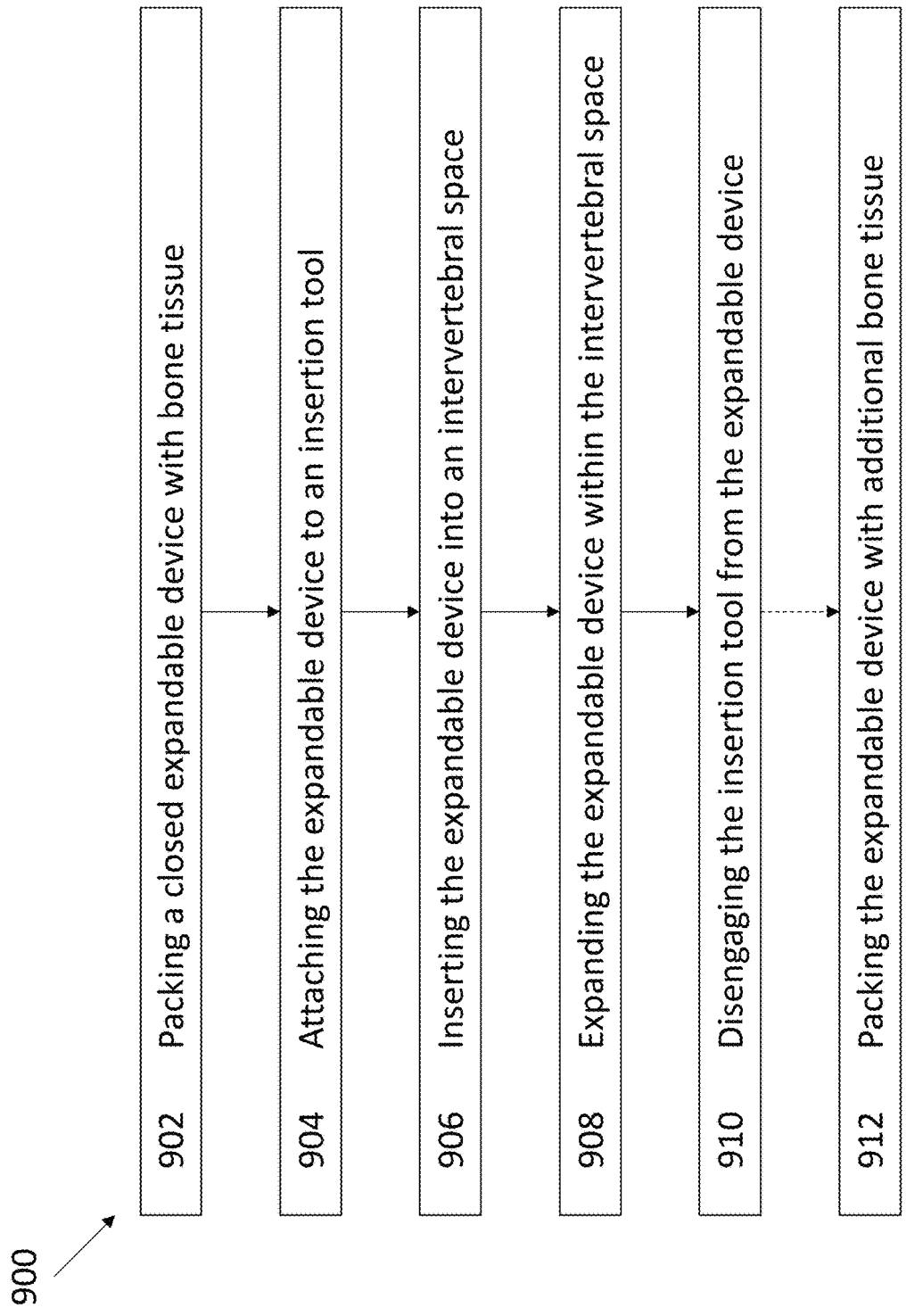
FIG. 33 is a flowchart of an exemplary method of using an expandable body device in a spinal fusion procedure.

Once the disc space has been prepared, an expandable device of the present invention may be used to fuse the spine. Referring now to FIG. 33, an exemplary method 900 of inserting an expandable device into a disc space is depicted. In step 902, a closed expandable device is packed with bone tissue. In various embodiments, the expandable device can further include one or more components to encourage healing, including stem cells, anti-inflammatories, antibiotics, antivirals, and the like. In step 904, the expandable device is attached to an insertion tool. In step 906, the expandable device is inserted into an intervertebral space. In step 908, the expandable device is expanded with the insertion tool within the intervertebral space. In step 910, the insertion tool is disengaged from the expandable device. In an optional step 912, the expandable device is further packed with additional bone tissue. Any suitable imaging technique, such as ultrasound or x-ray, may be used during any step to confirm proper placement of the expandable device within the intervertebral space.

In other embodiments, the expandable devices of the present invention are useful as mechanical spacers. For example, in any various mechanical applications, there may be a need to temporarily or permanently provide a support within a space. As described elsewhere herein, the expandable devices of the present invention can further include one or more sensors for monitoring performance, including temperature sensors, gyroscopes, pressure sensors, corrosion sensors, and the like.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An expandable device, comprising:
   a first and a second superior arm and a first and a second inferior arm, each arm having an anterior and a posterior end and a top and a bottom surface, and each arm having an anterior and posterior slot through the top and bottom surface, wherein the first superior arm is positioned over the first inferior arm with anterior and posterior slots in alignment, and the second superior arm is positioned over the second inferior arm with anterior and posterior slots in alignment;
   four cylindrical bolts positioned within each of the slots of the arms, each bolt having a top end, a bottom end, an outer surface, and within the outer surface a pin guide near each of top and bottom ends of each bolt, each pin guide comprising an open position near an end of the bolt and a closed position between the top and bottom ends of the bolt;
   a first rod connecting each of the bolts positioned within the anterior slots of the arms, and a second rod connecting each of the bolts positioned within the posterior slots of the arms; and
   a plurality of pins, each pin connected to an inner surface of each of the slots of the arms and slidably engaged to a pin guide of the bolt positioned within the respective slot.

2. The device of claim 1, wherein each of the four arms are substantially parallel to each other in a closed configuration.

3. The device of claim 2, wherein the four arms are movable about the four bolts while maintaining substantially parallel alignment to each other.

4. The device of claim 1, wherein each pin guide extends in a curve from about 60 to about 130 degrees around the outer surface of the bolt.

5. The device of claim 1, wherein the device comprises a closed configuration that positions the four arms adjacent to each other and positions the plurality of pins near the middle of each bolt.

6. The device of claim 1, wherein the device comprises an open configuration that positions the four arms away from each other and positions the plurality of pins near the top and bottom ends of each bolt.

7. The device of claim 1, wherein at least one arm comprises a locking bit drivable into a bolt.

8. The device of claim 1, wherein each arm comprises one or more cavities.

9. The device of claim 8, wherein the cavities are prefilled with bone tissue.

10. The device of claim 8, wherein the cavities are prefilled with a therapeutic selected from the group consisting of: a population of stem cells, an anti-inflammatory, an antibiotic, and an antiviral.

11. The device of claim 8, wherein the cavities are sized to fit a sensor selected from the list consisting of: a temperature sensor, a pressure sensor, a corrosion sensor, and a gyroscope.

12. The device of claim 1, sized to fit within an intervertebral disc space.

13. The device of claim 1, wherein each of the first and second superior arms comprises a connector or a socket extending from its posterior end.

14. The device of claim 1, wherein the first superior arm and the first inferior arm each comprises a connector or a socket extending from its posterior end.

15. The device of claim 1, wherein the first superior arm comprises a connector or a socket extending from its posterior end, and the second rod comprises a rung.

16. The device of claim 1, wherein each cylindrical bolt comprises a first, a second, a third, and a fourth pin guide, the first and second pin guides positioned opposite from each other, each extending from between the top and bottom ends of the bolt and towards the top end of the bolt, and the third and fourth pin guides positioned opposite from each other, each extending from between the top and bottom ends of the bolt and towards the bottom end of the bolt.

17. An expandable device, comprising:
    a first and a second superior arm and a first and a second inferior arm, each arm having an anterior and a posterior end and a top and a bottom surface, and each arm having an anterior and posterior slot, wherein the first superior arm is positioned over the first inferior arm with anterior and posterior slots in alignment, and the second superior arm is positioned over the second inferior arm with anterior and posterior slots in alignment;
    four bolts secured in pairs by a connecting rod and positioned within aligned anterior and posterior slots in each arm, each bolt secured within each slot by a pin, and each bolt having pin guides within an outer surface of the bolt near each of top and bottom ends of the bolt, each pin guide having a closed position between top and bottom ends of the bolt and an open position near one of the top and the bottom ends of the bolt, wherein each pin that secures a bolt to an arm is slidably engaged with a pin guide of the bolt.

18. The expandable device of claim 17, wherein each bolt includes a first, a second, a third, and a fourth pin guide, the first and second pin guides positioned opposite from each other, each extending from between the top and bottom ends of the bolt and towards the top end of the bolt, and the third and fourth pin guides positioned opposite from each other, each extending from between the top and bottom ends of the bolt and towards the bottom end of the bolt.

19. The expandable device of claim 18, and wherein each pin that secures a bolt to an arm is slidably engaged with the opposing pin guides of the bolt.

20. An expandable device, comprising:
    a first and a second superior arm and a first and a second inferior arm, each arm having an anterior and a posterior end and a top and a bottom surface, and each arm having an anterior and posterior slot, wherein the first superior arm is positioned over the first inferior arm with anterior and posterior slots in alignment, and the second superior arm is positioned over the second inferior arm with anterior and posterior slots in alignment, one of the first and second superior arms including a connector or a socket extending from its posterior end;

four bolts secured in pairs by a connecting rod and positioned within aligned anterior and posterior slots in each arm, each bolt secured within each slot by a pin fixed to each arm, each bolt having pin guides within an outer surface of the bolt near each of top and bottom ends of the bolt, each pin guide having a closed position between top and bottom ends of the bolt and an open position near one of the top and the bottom ends of the bolt, each pin guide extending in a curve from about 60 to about 130 degrees around the outer surface of the bolt, wherein each pin that secures a bolt to an arm is slidably engaged with a pin guide of the bolt.

* * * * *